United States Patent [19]

Terashima et al.

[11] Patent Number: 5,629,430

[45] Date of Patent: May 13, 1997

[54] TRIFLUOROMETHYLPYRROLOINDOLE-CARBOXYLIC ACID ESTER AND PROCESS FOR PRODUCTION THEREOF

[75] Inventors: Shiro Terashima, Tokyo; Yasumichi Fukuda; Yasuo Oomori, both of Tochigi-ken, all of Japan

[73] Assignees: Kyorin Pharmaceutical Co., Ltd.; Sagami Chemical Research Center, both of Tokyo, Japan

[21] Appl. No.: 381,981

[22] PCT Filed: Aug. 19, 1993

[86] PCT No.: PCT/JP93/01159

§ 371 Date: Jun. 14, 1995

§ 102(e) Date: Jun. 14, 1995

[87] PCT Pub. No.: WO94/04535

PCT Pub. Date: Mar. 3, 1994

[30] Foreign Application Priority Data

Aug. 21, 1992 [JP] Japan .................................. 4-222862
Aug. 18, 1993 [JP] Japan .................................. 5-204255

[51] Int. Cl.[6] ............................................ C07D 487/04
[52] U.S. Cl. .......................... 548/421; 548/425; 548/433; 544/363; 546/85; 546/87; 546/135; 546/140; 546/146; 546/148; 546/174; 546/187
[58] Field of Search .............................. 548/421, 433, 548/425; 544/363; 546/85, 140, 174

[56] References Cited

U.S. PATENT DOCUMENTS 4,978,757 12/1990 Kelly et al. ............................ 548/421
5,101,038 3/1992 Nakano et al. ........................ 548/421

FOREIGN PATENT DOCUMENTS 3-128379 5/1991 Japan .
4-99774 3/1992 Japan .
4-117383 4/1992 Japan .

*Primary Examiner*—Jacqueline Haley
*Attorney, Agent, or Firm*—McAulay Fisher Nissen Goldberg & Kiel, LLP

[57] ABSTRACT

Trifluoromethylpyrroloindolecarboxylic acid ester derivatives, and optical isomers and pharmaceutically acceptable salts thereof are provided which are represented by the general formula (1):

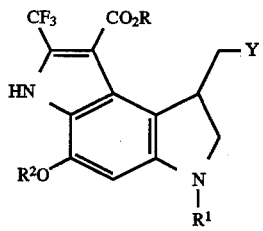

or the general formula (2):

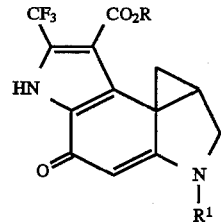

The compounds are antineoplastic agents which are selective to cancer cells, effective also to solid cancer, and less toxic.

7 Claims, No Drawings

TRIFLUOROMETHYLPYRROLOINDOLE-CARBOXYLIC ACID ESTER AND PROCESS FOR PRODUCTION THEREOF

This is a National Stage Application of PCT/JP93/01159 filed Aug. 19, 1993 and published as WO 94/04535 on Mar. 3, 1994.

TECHNICAL FIELDS

The present invention relates to novel antibacterial and antineoplastic 7-trifluoromethyl-1,2,3,6-tetrahydropyrrolo[3,2-e]indole-8-carboxylic acid ester derivatives, 6-trifluoromethyl-1,2,8,8a-tetrahydrocyclopropa[c]pyrrolo[3,2-e]indol-4 (5H)-one-7-carboxylic acid ester derivatives, optically active isomers thereof, and pharmaceutically acceptable salts thereof.

BACKGROUND TECHNIQUE

CC-1065 is disclosed as an antibacterial and antineoplastic antibiotic in J. Antibiotics, 31 1211 (1978) and ibid, 34 1119 (1981); and USP 4169888. Further, duocarmycin A having a similar structure thereto and analogues thereof are disclosed in WO87/06265, EP0318056, J. Antibiotics 42 1229 (1989), and JP-A-4-99774.

Further derivatives of CC-1065 are disclosed in JP-A-60-193989, and Japan Patent Kohyo 2-502005. Derivatives of duocarmycins are disclosed in JP-A-3-7287, JP-A-3-128379, EP0354583, and EP0406749. All of these compounds are derived by utilizing the base skeleton of an unmodified natural substance or by modifying chemically a natural substance.

The clinical therapy of cancer includes surgical excision, X-ray radiotherapy, pharmacotherapy using a chemotherapeutic agent(chemotherapy), and so forth. Of these therapies, chemotherapy is the one and only therapy for cancer having wide-spread metastasis in several body regions and for cancer at the terminal stage. Originally, chemotherapy is expected to be the least to burden a patient, while in facts, chemotherapeutic agents hitherto known impose severe suffer on patients due to strong adverse reactions. Further, there are several effective chemotherapeutic agents against leukemia which grows rapidly, but most of them are less effective for solid tumor which grows slowly. From these reasons, chemotherapy so far is not always primarily adopted for cancer.

In view of the present status of the chemotherapeutic agents, the inventors of the present invention have conducted comprehensively the investigation on compounds which exhibit high selectivity to cancer cells and exhibit high efficacy also on solid tumor with less toxicity.

DISCLOSURE OF INVENTION

It was found by the inventors of the present invention that the trifluoromethylpyrroloindolecarboxylic acid ester derivatives represented by the general formula (1) and (2) below, optical isomers thereof, and pharmaceutically acceptable salts thereof exhibit excellent antibacterial effects and antineoplastic effects, and further has high selectivity to cancer cells with low toxicity:

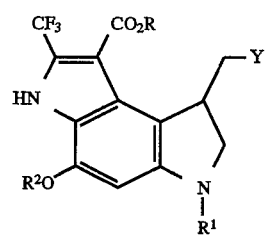

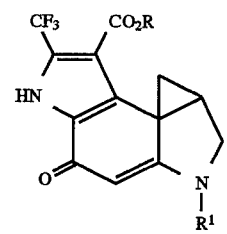

[In the formulas,

R is a lower alkyl group of $C_1$–$C_4$, $R^1$ is selected from the groups of α-amino acid residue,

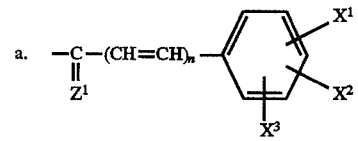

($X^1$, $X^2$, and $X^3$ are independently a hydrogen atom, OH, $OR^3$ ($R^3$ is a substituted or unsubstituted linear or branched lower alkyl group of $C_1$–$C_6$, or a substituted or unsubstituted aryl group), $OCOR^3$ ($R^3$ is the same as above), CHO, $NO_2$,

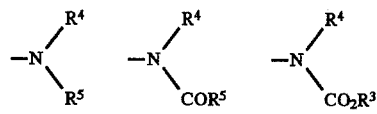

($R^4$ and $R^5$ are independently a hydrogen atom, a substituted or unsubstituted linear or branched lower alkyl group of $C_1$–$C_6$, or a substituted or unsubstituted aryl group ($R^3$ is the same as above)),

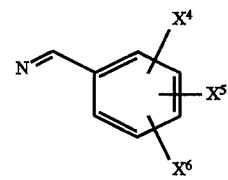

($X^4$, $X^5$ and $X^6$ are independently a hydrogen atom, or $OR^3$, or

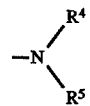

($R^3$, $R^4$, and $R^5$ are the same as above)),

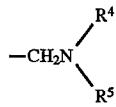

($R^4$, and $R^5$ are the same as above),

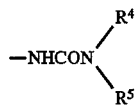

($R^4$, and $R^5$ are the same as above), $Z^1$ is O, S, or $NR^4$ ($R^4$ is the same as above), n is 0~2),

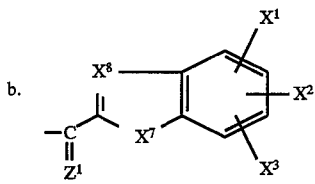

b.

($X^7$ is O, S, or NH, $X^8$ is CH or N ($X^1$, $X^2$, $X^3$, and $Z^1$ are the same as above)),

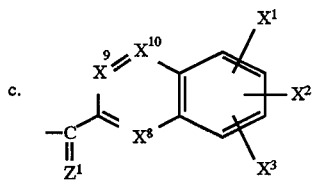

c.

($X^9$, and $X^{10}$ are independently CH or N ($X^1$, $X^2$, $X^3$, $X^8$, and $Z^1$ are the same as above)),

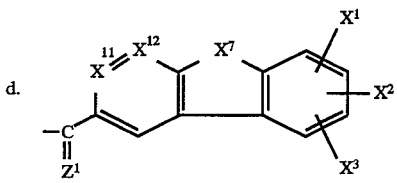

d.

($X^{11}$, and $X^{12}$ are independently CH or N ($X^1$, $X^2$, $X^3$, $X^7$ and $Z^1$ are the same as above)),

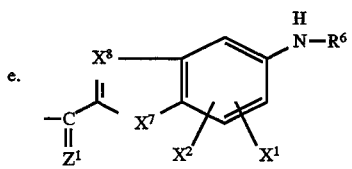

e.

($R^6$ is represented by the above formula a, b, c, or d ($X^1$, $X^2$, $X^7$, $X^8$, and $Z^1$ are the same as above))

f.
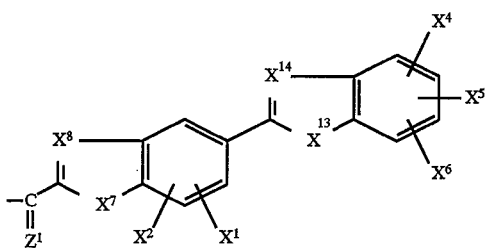

($X^{13}$ is O, S, or NH; $X^{14}$ is CH or N ($X^1$, $X^2$, $X^4$, $X^5$, $X^6$, $X^7$, $X^9$, and $Z^1$ are the same as above)), and g. 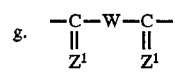

(W is $-(CH_2)_m-$, $-(CH_2)_m-Z^2-(CH_2)_n-$, or

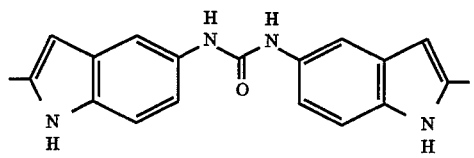

($Z^1$ is the same as above), $Z^2$ is S, O, or NH, and m and n are independently 0~16);

$R^2$ is a hydrogen atom, a protecting group for the hydroxyl group, or a biologically decomposable substituent; and Y is a halogen atom, an arylsulfonyloxy group, a lower alkylsulfonyloxy group, a haloalkylsulfonyloxy group, or an azide].

The protective group for an amino group herein includes linear or branched lower alkoxycarbonyl groups of 2~7 carbons such as methoxycarbonyl, ethoxycarbonyl, isopropoxycarbonyl, and t-butoxycarbonyl; haloalkoxycarbonyl groups such as 2,2,2-trichloroethoxycarbonyloxy, and 2,2,2-trichloro-1,1-dimethylethoxycarbonyl; and substituted or unsubstituted aralkyloxycarbonyl groups such as benzyloxycarbonyl, and 4-methoxybenzyloxycarbonyl. The protective group for the hydroxyl group includes lower alkyl groups of $C_1$~$C_4$ such as methyl and ethyl; and substituted or unsubstituted aralkyl groups such as benzyl, 4-methoxybenzyl, 2,4-dimethoxybenzyl, benzhydryl, and trityl. A biologically decomposable substituent includes lower alkanoyl groups, aryloyl groups, lower alkoxycarbonyl groups, substituted or unsubstituted aryloxycarbonyl groups, α-amino acid acyl radicals; substituted or unsubstituted carbamoyl groups such as N-(lower alkyl)carbamoyl, N, N-di(lower alkyl)carbamoyl, and N-arylcarbamoyl; substituted or unsubstituted pyrrolidinocarbonyl groups such as pyrrolidinocarbonyl, and 3-(dimethylamino) pyrrolidinocarbonyl; substituted or unsubstituted piperidinocarbonyl groups such as 4-(dimethylamino) piperidinocarbonyl, and (4-piperidinopiperidino)carbonyl; substituted or unsubstituted 1-piperazinylcarbonyl groups such as (4-methyl-1-piperazinyl)carbonyl, [4-[2-(dimethylamino)ethyl]-1-piperazinyl]carbonyl, [4-(2-(hydroxyethyl)-1-piperazinyl]carbonyl, and [4-[2-[2-(dimethylamino)ethoxy]ethyl]-1-piperazinyl]carbonyl; substituted or unsubstituted 1-morpholinocarbonyl groups; aryl- or alkyl-substituted silyl groups, which is capable of giving a hydroxyl group by decomposition in an organism.

The compound represented by the general formula (1) or (2) can be produced through the process described below according to the present invention.

The compound represented by the general formula (3a):

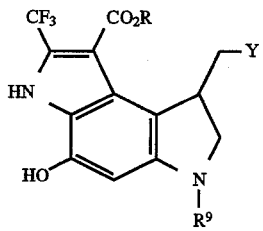
(3a)

(where $R^9$ is a protecting group for an amino group (R and Y are the same as shown above)) is converted by deprotection to the compound represented by the general formula (3b) below:

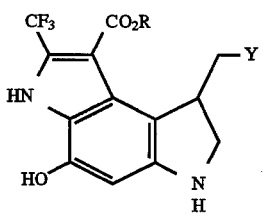
(3b)

(where R and Y are the same as above), or a salt thereof. This deprotection reaction may be carried out by a known method such as the method described in "Protective Groups in Organic: Synthesis" 2nd Ed., pp. 315–348 (1990).

For example, in the case where $R^9$ is a t-butoxycarbonyl group, the reaction is conducted in an ethyl acetate solution containing 3N hydrogen chloride at a temperature of from 0° C. to 50° C., preferably at room temperature for 10 minutes to 2 hours, and the solvent is removed by distillation to obtain the compound of the general formula (3b) in a form of hydrochloride salt with a high purity.

Subsequently, the compound represented by the general formula (3b) or its salt is reacted with a compound represented by the general formula (5a):

$$R^1-V \quad (5a)$$

(Where V is a reactive group such as a halogen atom, a 1-imidazolyl group, a 4-nitrophenoxy group, and a succinimidoyloxy group or $OR^1$ ($R^1$ is the same as above): the compound (5a) being a halide of a carboxylic acid or thiocarboxylic acid, an imidazolide of a carboxylic acid or thiocarboxylic acid, an active ester of a carboxylic acid or thiocarboxylic acid, a mixed or symmetric acid anhydride of a carboxylic acid or a thiocarboxylic acid or an imidoyl derivative, e.g., imidoyl chloride, or the compound is condensed with a carboxylic acid represented by the general formula (5b):

$$R^1-OH \quad (5a)$$

(where $R^1$ is the same as above) in the presence of a condensing agent such as dicyclohexylcarbodiimide (DCC) and 3-ethyl-1-(3-dimethylaminopropyl)carbodiimide hydrochloride (EDCI). Thereby, a compound is prepared which is represented by the general formula (3c):

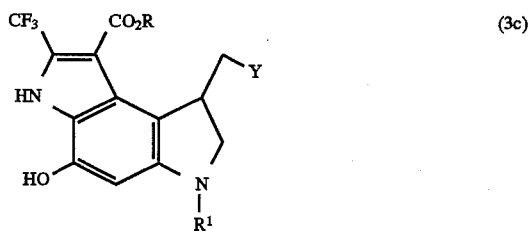
(3c)

(where R, $R^1$, and Y are the same as above). This condensation reaction is readily allowed to proceed in the presence or the absence of an organic base, e.g., triethylamine, diisopropylethylamine, pyridine, dimethylaminopyridine, etc., or an inorganic base, e.g., sodium hydrogencarbonate, and potassium carbonate in a solvent, e.g., methylene chloride, toluene, acetonitrile, N, N-dimethylformamide, dimethyl sulfoxide, tetrahydrofuran, etc., or a mixture thereof at a temperature of –20°~50° C. for 30 minutes to 48 hours.

The compound represented by the general formula (3c) can be converted to a prodrug represented by the general formula (3d):

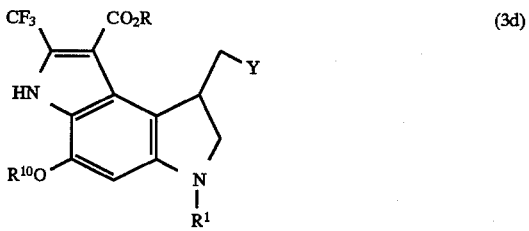
(3d)

(where $R^{10}$ is a biologically decomposable substituent (R, $R^1$, and Y are the same as above)) by treatment with a lower alkanoyl chloride, an aryloyl chloride, a lower alkoxycarbonyl chloride, an aryloxycarbonyl chloride, an acid chloride of α-amino acid, a substituted or unsubstituted carbamoyl chloride, or an active ester thereof. This reaction is conducted in the presence or the absence of an organic base, e.g., triethylamine, diisopropylethylamine, pyridine, dimethylaminopyridine, etc., or an inorganic base, e.g., sodium hydrogencarbonate, potassium carbonate, etc. in an inert solvent at a temperature of –20°~100° C., preferably 0° to 50° C.

Further, the aforementioned compound represented by the general formula (3c):

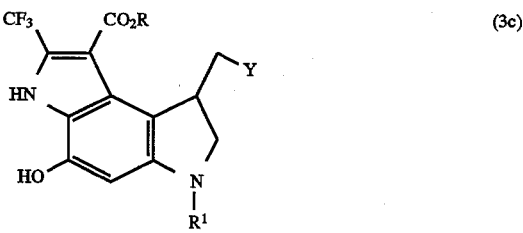
(3c)

(where R, $R^1$ and Y are the same as above) can be converted by ring closure in the presence of a base to a compound represented by the general formula (4a):

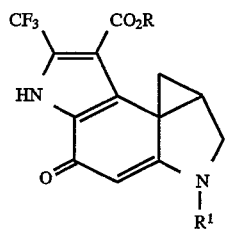

(where R, and $R_1$ are the same as above).

This reaction can be conducted by reacting the above compound (3c) with 1~10 equivalent moles, preferably 1~5 equivalent moles of an organic base, e.g., diazabicyclic base, triethylamine, etc. or an inorganic base, e.g., sodium hydroxide, sodium hydride, potassium carbonate, etc. in an inert solvent e.g., dimethylformamide, acetonitrile, tetrahydrofuran, methylene chloride, etc. or a mixture thereof at −78°~100° C., preferably 0°~50° C. for 10 minutes to 24 hours, preferably 20 minutes to 5 hours. Furthermore, the above compound represented by the general formula (4a) can be converted to the compound represented by the above general formula (3c) by treatment thereof in the presence of an acid, e.g., hydrogen chloride, hydrogen bromide, hydrochloric acid, hydrobromic acid, 20 minutes acid, benzenesulfonic acid, methanesulfonic acid, trifluoromethanesulfonic acid, hydrazoic acid, etc. in an inert solvent, e.g., ethyl acetate, methylene chloride, alcohol, acetonitrile, dimethylformamide, etc. at a temperature of from −20° C. to the boiling point of the solvent, preferably 0°~50° C. For this reaction, an excessive amount of the acid is preferably used to shorten the reaction time.

The compounds which are the starting substances of the present invention represented by the general formulas (3) and (4) are important intermediates:

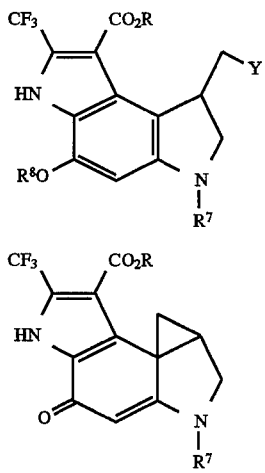

(where $R^7$ is a hydrogen atom, or a protective group for amino group, and $R^8$ is a hydrogen atom or a protective group for hydroxyl group (R and Y are the same as above)), and can be produced by the processes below.

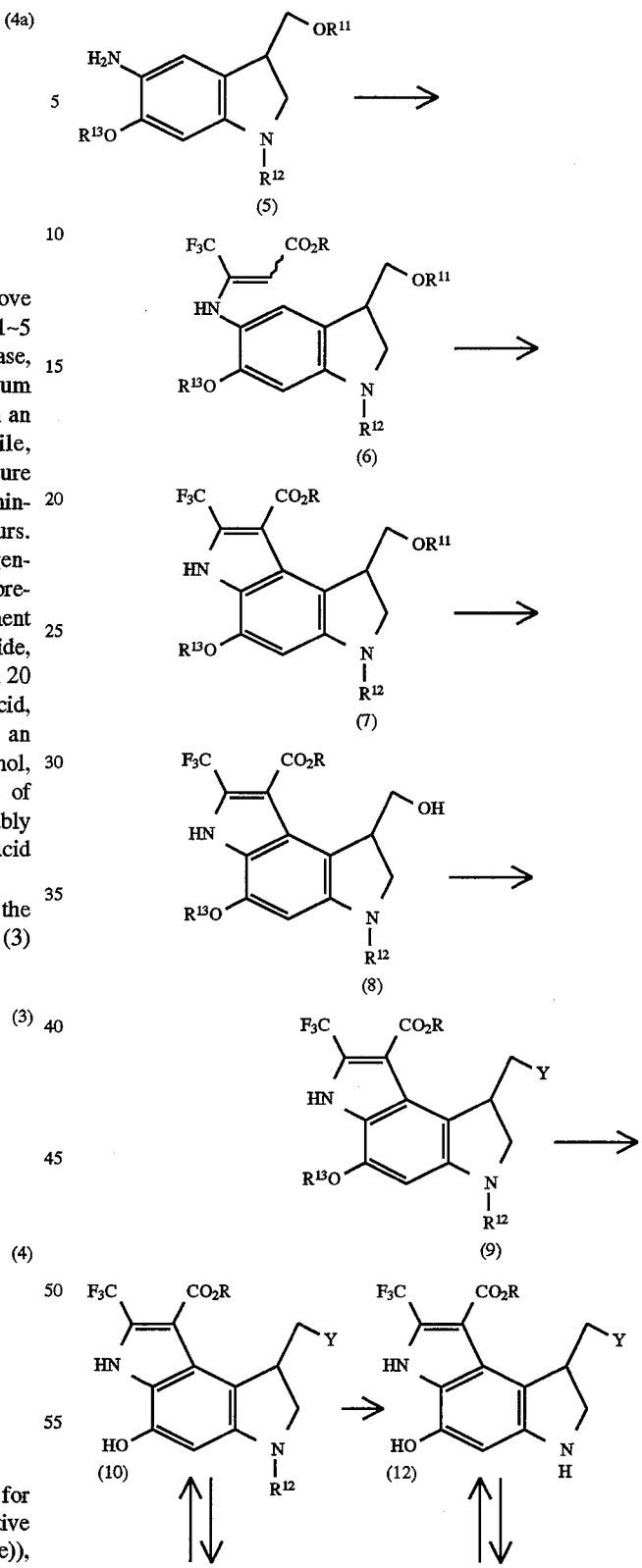

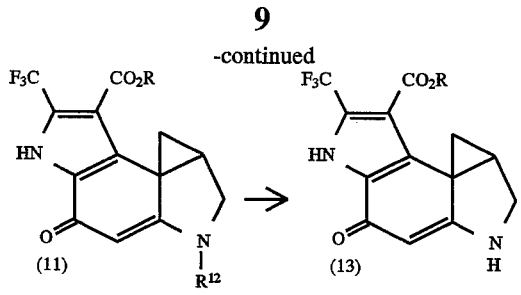

(where $R^{11}$ is a protective group for the hydroxyl group, $R^{12}$ is a protective group for the amino group, and $R^{13}$ is a protective group for the hydroxyl group (R, and Y are the same as above)

Optically active isomers of the compounds of the general formula (1) or (2) can be produced by use of an optically active isomers of the compound represented by the general formula (5). The optically active isomers of the compound of the general formula (5) can be obtained by optical resolution after conversion to diastereomers according to the method described, for example, in Journal of American Chemical Society, Vol. 112, p. 5230 (1990). In another method, the alcohol derivative represented by the general formula (8) is converted to diastereomeric esters of an optically active carboxylic acid, and is subjected to optical resolution to obtain an optically active intermediate. The compound represented by the general formula (1) or (2) are useful singly or in combination with a pharmaceutically acceptable additive for antibacterial and antineoplastic agent.

For example, the compound represented by the general formula (1) or (2) is dissolved in physiological saline or an aqueous solution of glucose, mannitol, lactose, or the like to provide a medicinal composition suitable for injection.

In another example, a salt of the compound of the general formula (1) or (2) is freeze-dried by a conventional manner and is mixed with sodium chloride or the like to prepare a readily soluble powder for obtaining injectable solution. This medicinal composition may contain, if necessary, an additive known in the medicine field, for example, a pharmaceutically acceptable salt.

The oral medicine includes tablets, capsules, powers, granules, ampules, and the like, which may contain a medicinal additive known in the medical preparation field. If desired, these medicine may be used for intraarterial medication, intraperitoneal medication, intrapleural medication, and so forth.

The amount of the doses differs depending on the age of the patient, the symptom, etc., and usually 0.00001 to 100 mg/kg/day for mammals including humans. The doses is given, for example, once or several times a day, or intermittently 1 to 4 times a week, or once for 2 to 4 weeks.

BEST MODE FOR PRACTICING INVENTION

The present invention is described below in detail by reference to examples without limiting the invention in any way.

EXAMPLE 1

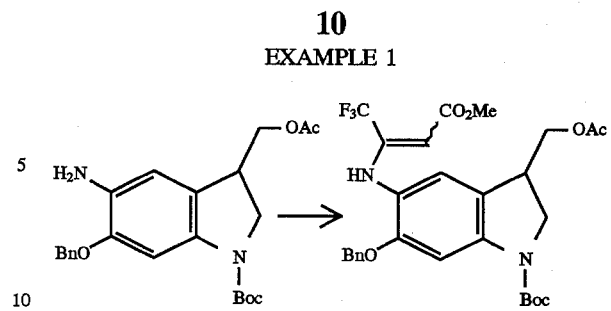

Into 0.2 ml of methanol, was dissolved 41.2 mg (0.1 mmol) of 3-acetoxymethyl-5-amino-6-benzyloxy-1-t-butoxycarbonyl-2,3-dihydro-1H-indole. Thereto, 16.7 mg (0.11 mmol) of methyl 3-trifluoromethylacetylenecarboxylate was added dropwise under ice cooling. After 15 minutes, the reaction mixture was brought to room temperature. After one hour, the solvent was distilled off. The obtained residue was purified by silica gel column chromatography (hexane: ethyl acetate=2:1). Thereby, methyl 3-(3-acetoxymethyl-6-benzyloxy-1-t-butoxycarbonyl-2,3-dihydro-1H-indol-5-yl) amino-3-trifluoromethylacrylate was prepared in a crystal form in pale cream color in a yield of 54.7 mg (97%).

m.p. 114°~115° C.

Analysis: $C_{28}H_{31}F_3N_2O_7$

|  | C | H | N |
| --- | --- | --- | --- |
| Calculated | 59.57 | 5.53 | 4.96 |
| Found | 59.48 | 5.45 | 4.88 |

NMR (CDCl$_3$) δ: 1.56(9H,s), 2.08(3H,s), 3.57(1H,m), 3.72(3H,s), 3.78(1H,br), 4.06–4.18(3H,m), 5.09(2H,s), 5.32 (1H,s), 7.08(1H,s), 7.29–7.39(5H,m), 7.70(1H,br,s), 9.51 (1H,s)

EXAMPLE 2

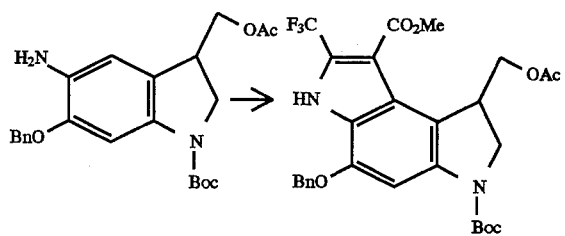

A crude acrylic acid derivative was prepared in the same manner as in Example 1 from 1.031 g (2.5 mmol) of 3-acetoxymethyl-5-amino-6-benzyloxy-1-t-butoxycarbonyl-2,3-dihydro-1H-indole and 418.2 mg of methyl 3-trifluoromethylacetylenecarboxylate. This crude acrylic acid derivative was heated with 1.122 g (5 mmol) of palladium acetate in 250 ml of N, N-dimethylacetamide at 70° C. for 3.5 hours. The reaction mixture was poured onto ice, and thereto 200 ml of ethyl acetate/toluene (1:1) was added. The insoluble matter was removed by filtration. The organic layer was washed with water, and was dried over anhydrous sodium sulfate. Thereafter, the solvent was distilled off. The obtained residue was purified by silica gel column chromatography (hexane: ethyl acetate=3:1). Thereby, methyl 1-acetoxymethyl-5-benzyloxy-3-t-butoxycarbonyl-7-trifluoromethyl-1,2,3,6- tetrahydropyrrolo[3,2-e]indole-8-carboxylate was prepared in a colorless crystal state in a yield of 815.1 mg (58%).

m.p. 156.5°~157.5° C.

Analysis: $C_{28}H_{29}F_3N_2O_7$

|  | C | H | N |
|---|---|---|---|
| Calculated | 59.78 | 5.20 | 4.80 |
| Found | 59.66 | 5.11 | 5.00 |

NMR (CDCl$_3$) δ: 1.58(9H,s), 2.03(3H,s), 3.91(3H,s), 3.88–3.98(1H,m), 3.98–4.08(2H,m), 4.21(1H,dd,J=4 Hz, J=10 Hz), 4.28(1H,m), 5.22(2H,s), 7.39–7.49(5H,m), 7.95(1H,br,s), 9.17(1H,s)

EXAMPLE 3

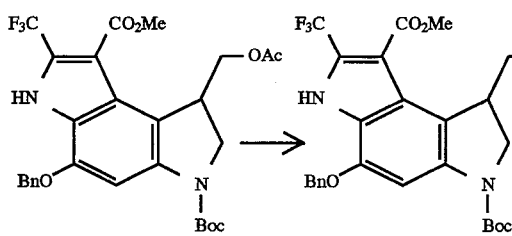

In 4 ml of methanol, was suspended 225 mg (0.4 mmol) of methyl 1-acetoxymethyl-5-benzyloxy-3-t-butoxycarbonyl-7-trifluoromethyl-1,2,3,6-tetrahydropyrrolo[3,2-e]indole-8-carboxylate. Thereto 110.6 mg (0.8 mmol) of potassium carbonate was added, and the mixture was stirred for 7 hours. It was neutralized with 10% citric acid, and diluted with water. The precipitated crystalline matter was collected by filtration, washed with water, and dried. Thereby, methyl 5-benzyloxy-3-t-butoxycarbonyl-1-hydroxymethyl-7-trifluoromethyl-1,2,3,6-tetrahydropyrrolo[3,2-e]indole-8-carboxylate was prepared in a colorless crystalline state in a yield of 206.5 mg (99%).

EXAMPLE 4

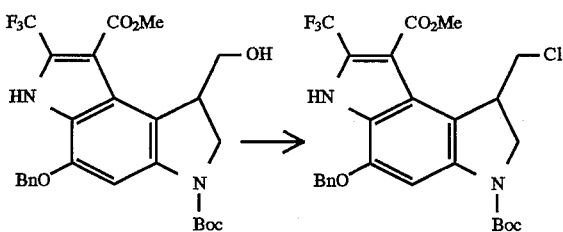

104.1 Milligrams (0.2 mmol) of methyl 5-benzyloxy-3-t-butoxycarbonyl-1-hydroxymethyl-7-trifluoromethyl-1,2,3,6-tetrahydropyrrolo[3,2-e]indole-8-carboxylate, and 104.9 mg (0.4 mmol) of triphenylphosphine were suspended in 1 ml of anhydrous acetonitrile. Thereto 115.3 µl (1.2 mmol) of carbon tetrachloride was added dropwise. The mixture was stirred for 5 hours under atmosphere of argon. After removal of the solvent, the residue was purified by silica gel column chromatography (hexane:ethyl acetate=4:1) to obtain methyl 5-benzyloxy-3-t-butoxycarbonyl-1-chloromethyl-7-trifluoromethyl-1,2,3,6-tetrahydropyrrolo[3,2-e]indole-8-carboxylate in a yield of 106.7 mg (99%).

m.p.161.5°~162.5° C.

Analysis: $C_{26}H_{26}ClF_3N_2O_5$

|  | C | H | N |
|---|---|---|---|
| Calculated | 57.94 | 4.86 | 5.20 |
| Found | 58.17 | 4.85 | 5.27 |

NMR (CDCl$_3$) δ: 1.59(9H,s), 3.34(1H,t,J=10.3 Hz), 3.82 (1H,dd,J=3 Hz, J=10 Hz), 3.96(3H,s), 4.01(1H,dd,J=10 Hz, J=12 Hz), 4.21–4.31(2H,m), 5.22(2H,s), 7.40–7.48(5H,m), 7.95(1H,br,s), 9.22(1H,s)

EXAMPLE 5

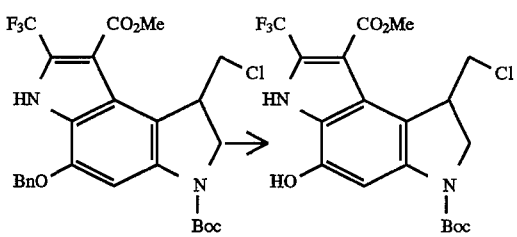

In 2.63 ml of tetrahydrofuran, was dissolved 106.7 mg (198 µmol) of methyl 5-benzyloxy-3-t-butoxycarbonyl-1-chloromethyl-7-trifluoromethyl-1,2,3,6-tetrahydropyrrolo[3,2-e]indole-8-carboxylate. Thereto, 64 mg of 10% palladium on carbon was added, and then 656.4 µl of 25% ammonium formate was added dropwise under ice cooling. The mixture was stirred for one hour, and then the reaction mixture was extracted with ethyl acetate. The extract was dried over anhydrous sodium sulfate, and the solvent was distilled off to obtain methyl-3-t-butoxycarbonyl-1-chloromethyl-5-hydroxy-7-trifluoromethyl-1,2,3,6-tetrahydropyrrolo[3,2-e]indole-8-carboxylate in a yield of 87.9 mg (99%).

NMR (CDCl$_3$) δ: 1.59(9H,s), 3.33(3H,t,J=10.3 Hz), 3.82 (1H,dd,J=3 Hz,J=10 Hz), 3.96(3H,s), 4.01(1H,dd,J=9 Hz, J=12 Hz), 4.21(1H,d,J=12 Hz), 4.29(1H,m), 7.34(1H,br,s), 7.76(1H,br,s), 9.26(1H,s)

EXAMPLE 6

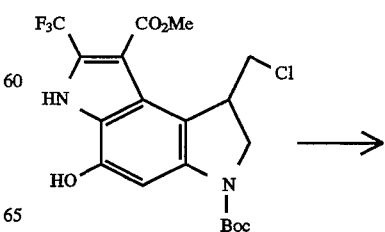

13

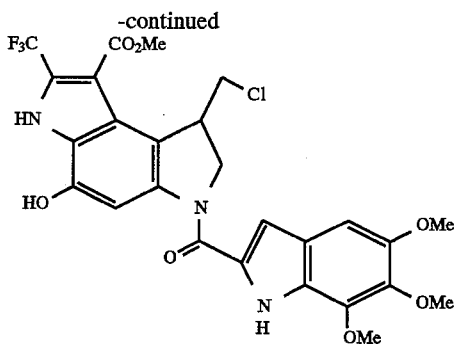
-continued

To 42.6 mg(95 μmol) of methyl 3-t-butoxycarbonyl-1-chloromethyl-5-hydroxy-7-trifluoromethyl-1,2,3,6-tetrahydropyrrolo[3,2-e]indole-8-carboxylate, 1.6 ml of 3M hydrogen chloride-ethyl acetate was added, and the mixture was stirred at room temperature for one hour. Then the solvent was distilled off. The residue with 23.8 mg (95 mol) of 5,6,7-trimethoxyindole-2-carboxylic acid, and 54.6 mg (285 μmol) of 1-(3-dimethylaminopropyl)-3-ethylcarbodiimide hydrochloride was stirred in 0.95 ml of anhydrous dimethylformamide at room temperature under atmosphere of argon overnight. Water was added to the liquid reaction mixture. The resulting mixture was extracted with methylene chloride, and the extract solution was washed with water, 10% sodium hydrogencarbonate, and saturated sodium chloride solution successively, and dried over anhydrous sodium sulfate. Therefrom the solvent was distilled off. The residue was purified by silica gel column chromatography (chloroform:methanol=20:1) to obtain methyl 1-chloromethyl-5-hydroxy-7-trifluoromethyl-3-(5,6,7-trimethoxy-1H-indol-2-ylcarbonyl)-1,2,3,6-tetrahydropyrrolo[3,2-e]indole-8-carboxylate in a yield of 45.3 mg (82%).

NMR (CDCl$_3$) δ: 3.22(1H,t,J=10 Hz), 3.76(1H,dd,J=3 Hz,J=11 Hz), 3.80(3H,s), 3.82(3H,s), 3.85(3H,s), 3.97(3H, s), 4.31(1H,m), 4.41(1H,t,J=9 Hz), 4.60(1H,d,J=10 Hz), 6.78(1H,s), 6.87(1H,d,J=2 Hz), 7.89(1H,s), 9.15(1H, br,s), 9.45(1H,s)

EXAMPLE 7

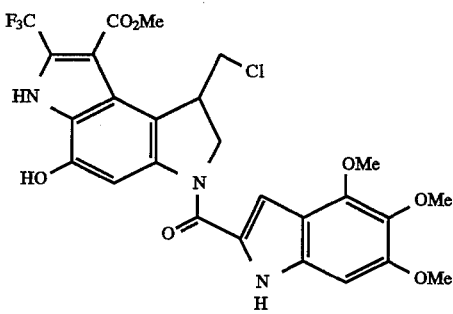

14

Methyl 1-chloromethyl-5-hydroxy-7-trifluoromethyl-3-(4,5,6-trimethoxy-1H-indol-2-ylcarbonyl)-1,2,3,6-tetrahydropyrrolo[3,2-e]indole-8-carboxylate was prepared in the same manner as above by using 5.8 mg (23 μmol) of 4,5,6-trimethoxyindole-2-carboxylic acid in a yield of 10.3 mg (77%).

NMR (CDCl$_3$)+DMSOd$_6$) δ: 3.35(1H,t,J=11 Hz), 3.86–3.89(1H,m), 3.88(3H,s), 3.89(3H,s), 3.98(3H,s), 4.15 (3H,s), 4.44(1H,m), 4.56(1H,t,J=10 Hz), 4.74(1H, d, J=10 Hz), 6.68(1H,s), 7.09(1H,s), 8.04(1H,br,s), 9.08(1H,s), 9.85 (1H,s), 11.4(1H,br,s)

EXAMPLE 8

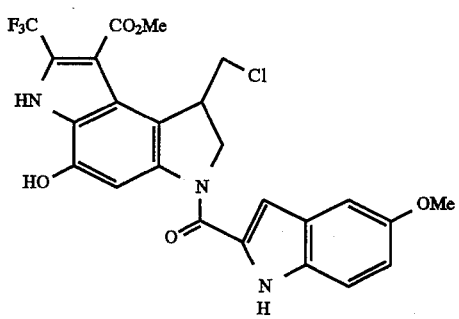

Methyl 1-chloromethyl-5-hydroxy-3-(5-methoxy-1H-indol-2-ylcarbonyl)-7-trifluoromethyl-1,2,3,6-tetrahydropyrrolo[3,2-e]indole-8-carboxylate was prepared in the same manner as above by using 11.2 mg (25 μmol) of methyl 3-t-butoxycarbonyl-1-chloromethyl-5-hydroxy-7-trifluoromethyl- 1,2,3,6-tetrahydropyrrolo[3,2-e]indole-8-carboxylate and 4.8 mg (25 μmol) of 5-methoxyindole-2-carboxylic acid in a yield of 7.2 mg (55%).

NMR (CDCl$_3$+DMSOd$_6$) δ:3.34(1H,t,J=10Hz), 3.87(3H, s), 3.87–3.91(1H,m), 3.97(3H,s), 4.44(1H,m), 4.55(1H,t,J= 10 Hz), 4.76(1H,d,J=11 Hz), 6.97–7.01(2H,m), 7.13(1H,s), 7.39(1H,d,J=10 Hz), 8.02(1H,s), 9.14(1H,dr,s), 9.81(1H,br, s), 11.45(1H,s)

EXAMPLE 9

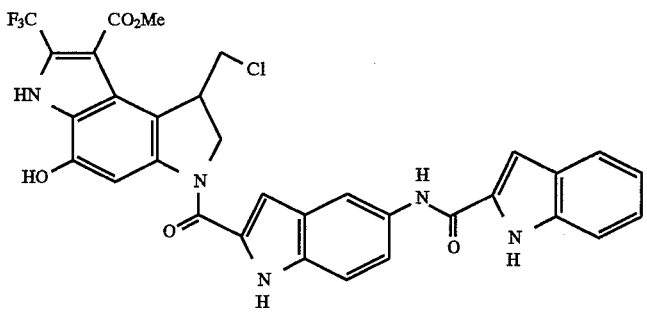

Methyl 1-chloromethyl-5-hydroxy-3-[5-[(1H-indol-2-ylcarbonyl)amino]-1H-indol-2-ylcarbonyl]-7-trifluoromethyl-1,2,3,6-tetrahydropyrrolo[3,2-e]indole-8-carboxylate was prepared in the same manner as above by reaction with 8.0 mg (25 μmol) of 5-(1H-indol-2-ylcarbonyl)amino-1H-indole-2-carboxylic acid in a yield of 7.5 mg (46%).

NMR (CDCl$_3$+DMSOd$_6$) δ: 3.37(1H,t,J=10 Hz), 3.89 (1H,dd,J=3 Hz, J=10.3 Hz), 3.96(3H,s), 4.40(1H,m), 4.58 (1H,t,J=11 Hz), 4.72(1H,d,J=11 Hz), 7.04(1H,d,J=2.0 Hz), 7.10(1H,t,J=7 Hz), 7.24(1H,t,J=7 Hz), 7.36(1H,s), 7.50(1H, s), 7.52(1H,s), 7.58(1H,dd,J=2 Hz, J=11 Hz), 7.59–7.63(1H, m) 7.66(1H,d,J=8 Hz), 7.96(1H,br,s), 8.24(1H,s), 9.59(1H, br,s), 9.75(1H,br,s)

carboxylate was prepared in the same manner as above by using 8.0 mg (25 μmol) of 5-(benzofuran-2-ylcarbonyl)amino-1H-indole-2-carboxylic acid in a yield of 9.1 mg (56%).

NMR (CDCl$_3$+DMSOd$_6$) δ: 3.37(1H,t,J=10 Hz), 3.88 (1H,m), 3.96(3H,s), 4.39(1H,m), 4.57(1H,t,J=10Hz), 4.71 (1H,d,J=11 Hz), 7.05(1H,s), 7.33(1H,t,J=8 Hz), 7.46(1H,t, J=8 Hz), 7.53(1H,d,J=9 Hz), 7.58(1H,d,J=9 Hz), 7.61–7.63 (2H,m), 7.73(1H,d,J=8 Hz), 7.95(1H,br,s), 8.22(1H,s), 9.57–9.60(2H,m), 11.05(1H,br), 12.09(1H,br)

EXAMPLE 10

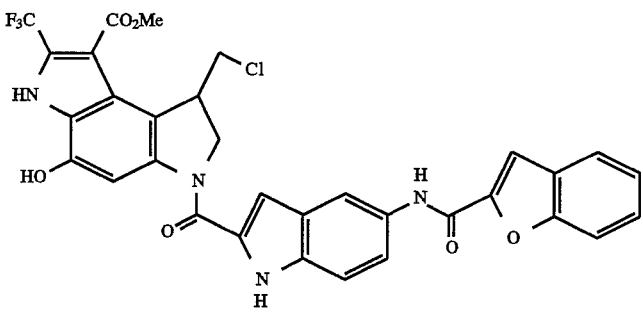

Methyl 3-[5-[(benzofuran-2-ylcarbonyl)amino]-1H-indol-2-ylcarbonyl]-1-chloromethyl-5-hydroxy-7-trifluoromethyl-1,2,3,6-tetrahydropyrrolo[3,2-e]indole-8-

EXAMPLE 11

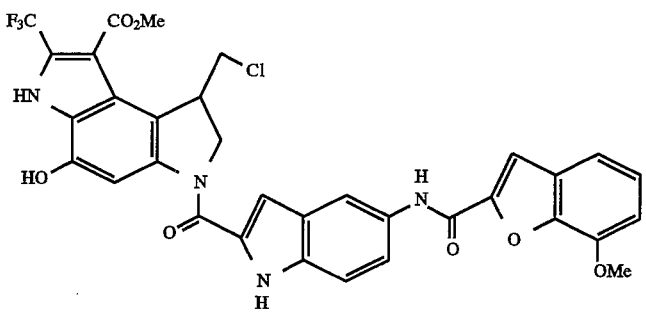

Methyl 1-chloromethyl-5-hydroxy-3-[5-[(7-methoxybenzofuran-2-ylcarbonyl)amino]-1H-indol-2-ylcarbonyl]-7-trifluoromethyl-1,2,3,6-tetrahydropyrrolo[3,2-e]indole- 8-carboxylate was prepared, in the same manner as above, by using 8.1 mg (23 μmol) of 5-(7-methoxybenzofuran-2-ylcarbonyl)amino-1H-indole-2-carboxylic acid, in a yield of 11.0 mg (70%).

NMR (CDCl$_3$+DMSOd$_6$) δ: 3.36(1H,t,J=10 Hz), 3.89 (1H,dd,J=3 Hz,J=11 Hz), 3.98(3H,s), 4.07(3H,s), 4.45(1H, m), 4.58(1H,t,J=10 Hz), 4.77(1H,d,J=11 Hz), 6.96(1H,d,J=8 Hz), 7.09(1H,s), 7.25(1H,d,J=8 Hz), 7.28–7.30(1H,m), 7.49 (1H,d,J=9 Hz), 7.53(1H,dd,J=2 Hz,J=9Hz), 7.60(1H,s), 8.02 (1H,br,s), 8.22(1H,s), 8.65(1H,s), 9.13(1H,s), 9.93(1H,s), 11.39(1H,br)

Methyl 1-chloromethyl-5-hydroxy-7-trifluoromethyl-3-[5-[(5,6,7-trimethoxy-1H-indol-2-ylcarbonyl)amino]-1H-indol-2-ylcarbonyl]-1,2,3,6-tetrahydropyrrolo[3,2-e]indole-8-carboxylate was prepared by using 9.4 mg (23 μmol) of 5-(5,6,7-trimethoxy1H-indol-2-ylcarbonyl)amino-1H-indole-2-carboxylic acid, in the same manner as above, in a yield of 13.2 mg (78%).

NMR (CDCl$_3$+DMSOd$_6$) δ: 3.36(1H,t,J=10 Hz), 3.89 (1H,m), 3.92(3H,s), 3.95(3H,s), 3.98(3H,s), 4.10(3H,s), 4.45(1H,m), 4.57(1H,t,J=10 Hz), 4.77(1H,d,J=10 Hz), 6.86 (1H, s), 7.06(1H,s), 7.17(1H,s), 7.47(1H,d,J=9 Hz), 7.53 (1H,dd,J=2 Hz,J=9 Hz), 8.02(1H,s), 8.20(1H,s), 9.07(1H,s), 9.11(1H,s), 9.87(1H,s), 9.91(1H,s), 11.39(1H,s)

EXAMPLE 12

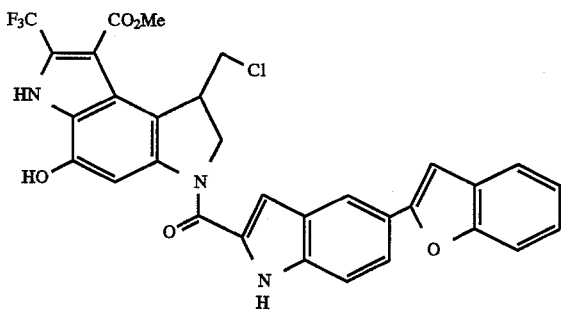

Methyl 3-(5-benzofuran-2-yl)-1H-indol-2-yl-carbonyl)-1-chloromethyl-5-hydroxy-7-trifluoromethyl-1,2,3,6-tetrahydropyrrolo[3,2-e]indole-8-carboxylate was prepared by using 6.4 mg (23 μmol) of 5-(benzofuran-2-yl)-1H-indole-2-carboxylic acid, in the same manner as above, in a yield of 0.6 mg (76%).

NMR (CDCl$_3$+DMSOd$_6$) δ: 3.37(1H,t,J=10 Hz), 3.90 (1H,dd,J=3 Hz,J=10 Hz), 3.98(3H,s), 4.47(1H,m), 4.59(1H, t,J=10.3 Hz), 4.78(1H,d,J=11 Hz), 7.00(1H,s), 7.14(1H,s), 7.21–7.29(2H,m), 7.52–7.59(3H,m), 7.81(1H,d,d,J=2 Hz,J=9 Hz), 8.02(1H,br), 8.27(1H,s), 9.17(1H,s)

EXAMPLE 13

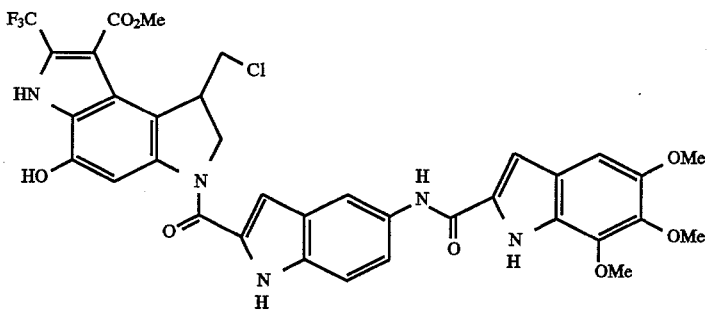

EXAMPLE 14

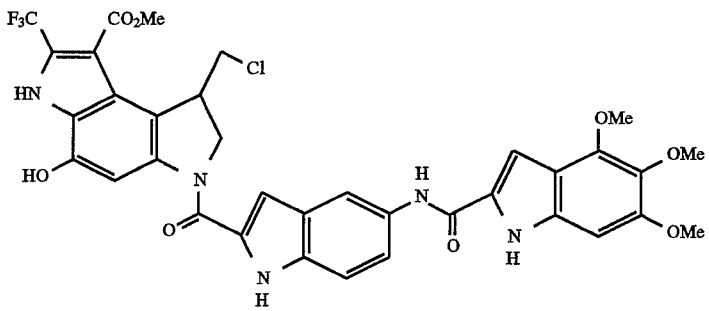

Methyl 1-chloromethyl-5-hydroxy-7-trifluoromethyl-3-[5-[(4,5,6-trimethoxy1H-indol-2-ylcarbonyl)amino]-1H-indol-2-ylcarbonyl]-1,2,3,6-tetrahydropyrrolo[3,2-e]indole-8-carboxylate was prepared by using 9.4 mg (23 μmol) of 5-(4,5,6-trimethoxy-1H-indol-2-ylcarbonyl)amino-1H-indole-2-carboxylic acid, in the same manner as above, in a yield of 8.5 mg (50%).

NMR (CDCl$_3$+DMSOd$_6$) δ: 3.36(1H,t,J=10 Hz), 3.81–3.93(1H,m), 3.877(3H,s), 3.879(3H,s), 3.98(3H,s), 4.15(3H,s), 4.45(1H,m), 4.57(1H,t,J=10 Hz), 4.77(1H,d,J=10 Hz), 6.68(1H,s), 7.06(1H,s), 7.35(1H,s), 7.47(1H,d,J=9 Hz), 7.54(1H,d,J=9 Hz), 8.03(1H,s), 8.21(1H,s), 8.99(1H,s), 9.15(1H,s), 10.02(1H,s), 10.09(1H,s), 11.44(1H,br)

NMR (CDCl$_3$+DMSOd$_6$) δ: 3.37(1H,t,J=10 Hz), 3.89(1H,dd,J=3 Hz,J=11 Hz), 3.98(3H,s), 4.44(1H,m), 4.57(1H, t,J=9 Hz), 4.76(1H,d,J=11 Hz), 7.07(1H,s), 7.50(1H,d,J=9 Hz), 7.55–7.61(3H,m), 7.90–8.00(h,m), 8.07(1H,d,J=9 Hz), 8.25(1H,s), 8.54(1H,s), 9.24(1H,s), 9.36(1H,s), 10.22(1H,s), 11.60(1H,br)

EXAMPLE 15

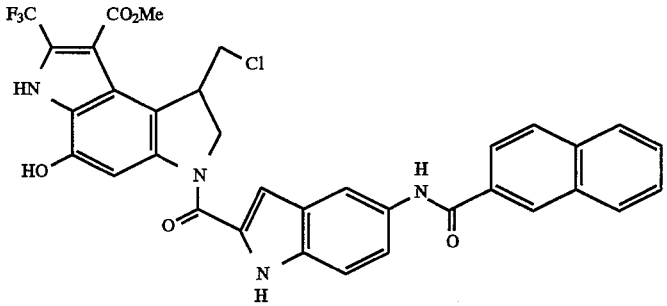

Methyl 1-chloromethyl-5-hydroxy-3-[5-[(naphthalene-3-ylcarbonyl)amino]-1H-indol-2-ylcarbonyl]-7-trifluoromethyl-1,2,3,6-tetrahydropyrrolo[3,2-e]indole-8-carboxylate was prepared in the same manner, by using 6.3 mg (19 μmol) of 5-(naphthalene-3-ylcarbonyl)amino-1H-indol-2-carboxylic acid, in a yield of 10.1 mg (80%).

EXAMPLE 16

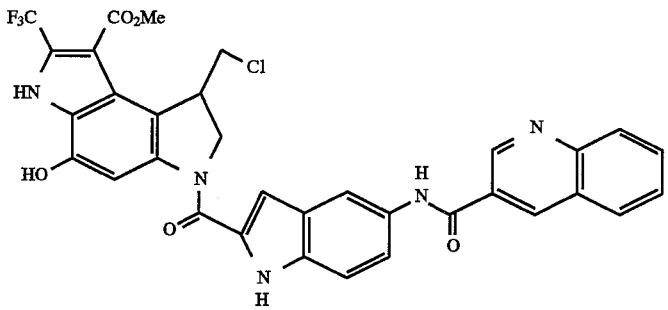

Methyl 1-chloromethyl-5-hydroxy-3-[5-[(quinoline-3-ylcarbonyl)amino]-1H-indol-2-ylcarbonyl]-7- trifluoromethyl-1,2,3,6-tetrahydropyrrolo[3,2-e]indole-8-carboxylate was prepared in the same manner, by using 7.6 mg (23 μmol) of (quinoline-3-ylcarbonyl)amino-1H-indole-2-carboxylic acid, in a yield of 6.4 mg (42%).

NMR (CDCl$_3$+DMSOd$_6$) δ: 3.37(1H,t,J=10 Hz), 3.89 (1H,dd,J=3 Hz,J=11 Hz), 3.98(3H,s), 4.44(1H,m), 4.58(1H, t,J=10 Hz), 4.77(1H,d,J=11 Hz), 7.07(1H,s), 7.49(1H,d,J=9 Hz), 7.61(1H,d,J=10 Hz), 7.66(1H,d,J=7 Hz), 7.83(1H,t,J=7 Hz), 7.97–8.01(1H,m), 8.18(1H,d,J=8 Hz), 8.25(1H,s), 8.87 (1H,s), 9.23(1H,s), 9.53(1H,s), 9.77(1H,br), 10.12(1H,br), 10.79(1H,br), 11.51(1H,br)

Methyl 1-chloromethyl-5-hydroxy-7-trifluoromethyl-3-[5-[(5,6,7-trimethoxyisoquinolin-3-ylcarbonyl)amino]-1H-indol-2-ylcarbonyl]-1,2,3,6-tetrahydropyrrolo[3,2-e]indole-8-carboxylate was prepared by using 9.7 mg (23 μmol) of 5-(5,6,7-trimethoxyisoquinolin-3-ylcarbonyl)amino-1H-indole-2-carboxylic acid, in the same manner as above, in a yield of 5.4 mg (89%).

NMR (CDCl$_3$+DMSOd$_6$) δ: 3.37(1H, t, J=10Hz), 3.89 (1H, m), 3.98(3H, s), 4.05(3H, s), 4.07(3H, s), 4.12(3H, s), 4.44(1H, m), 4.58(1H, m), 4.77(1H, d, J=7 Hz), 7.08(1H, s), 7.17(1H, s), 7.52(1H, d, J=7 Hz), 7.60(1H, m), 8.00(1H, br, s), 8.37(1H, s), 8.87(1H, s), 9.06(1H, s), 9.23(1H, s), 10.25 (1H, br), 10.92(1H, br), 11.58(1H, br)

EXAMPLE 17

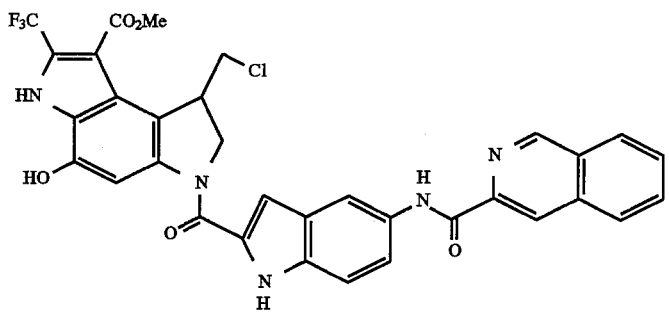

Methyl 1-chloromethyl-5-hydroxy-3-[5-[(isoquinolin-3-ylcarbonyl)amino]-1H-indol-2-ylcarbonyl]-7trifluoromethyl-1,2,3,6-tetrahydropyrrolo[3,2-e]indole-8-carboxylate was prepared by using 7.6 mg(23 μmol) of 3-(5-isoquinolin-3-ylcarbonyl)amino-1H-indole-2-carboxylic acid, in the same manner as above, in a yield of 8.3 mg (54%).

NMR (CDCl$_3$+DMSOd$_6$) δ: 3.37(1H, t, J=8Hz), 3.87–3.98(1H, m), 3.98(3H, s), 4.44(1H, m), 4.58(1H, t, J=8 Hz), 4.77(1H, d, J=11 Hz), 7.09(1H, s), 7.53(1H, d, J=9 Hz), 7.60(1H, d, J=9 Hz), 7.75(1H, t, J=8 Hz), 7.82(1H, t, J=8 Hz), 8.01–8.06(2H, m), 8.10(1H, d, J=8 Hz), 8.39(1H, s), 8.74(1H, s), 9.22(1H, br, s), 9.26(1H, s), 10.19(1H, br, s), 10.31(1H, s), 1.56(1H, br, s)

EXAMPLE 18

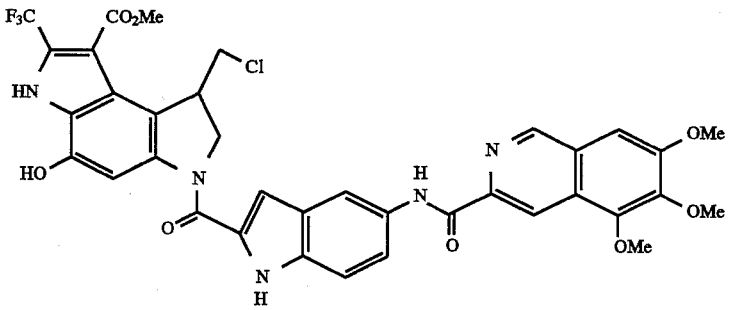

EXAMPLE 19

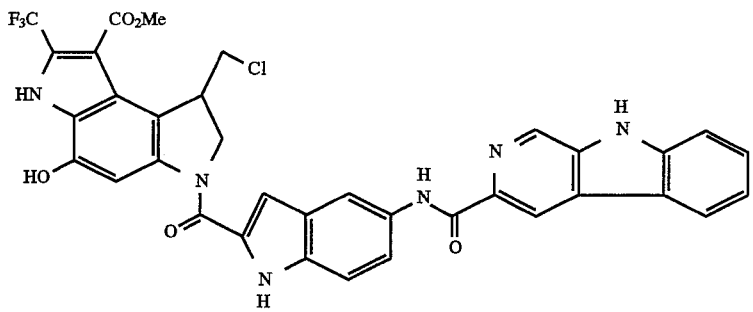

Methyl 1-chloromethyl-5-hydroxy-3-[5-[(9H-pyrido[3,4-b]indol-3-ylcarbonyl)amino]-1H-indol-2ylcarbonyl]-7-trifluoromethyl-1,2,3,6-tetrahydropyrrolo[3,2e]indole-8-carboxylate was prepared by using 8.5 mg (23 μmol) of 5-(9H-pyrido[3,4-b]indol-3-ylcarbonyl)amino-1H-indole-2-carboxylic acid, in the same manner as above, in a yield of 12.5 mg (78%).

NMR (CDCl$_3$+DMSOd$_6$) δ: 3.37(1H, t, J=10 Hz), 3.90 (1H, d, J=11 Hz), 3.98(3H, s), 4.44(1H, m), 4.59(1H, t, J=10 Hz), 4.77(1H, d, J=11 Hz), 7.09(1H, s), 7.33(1H, t, J=8 Hz), 7.53(1H, d, J=9 Hz), 7.57–7.62(3H, m), 8.01(1H, br, s), 8.24(1H, d, J=8 Hz), 8.37(1H, s), 8.89(1H, s), 9.01(1H, s), 9.27(1H, s), 10.25(2H, m), 11.03(1H, s), 11.63(1H, br)

EXAMPLE 20

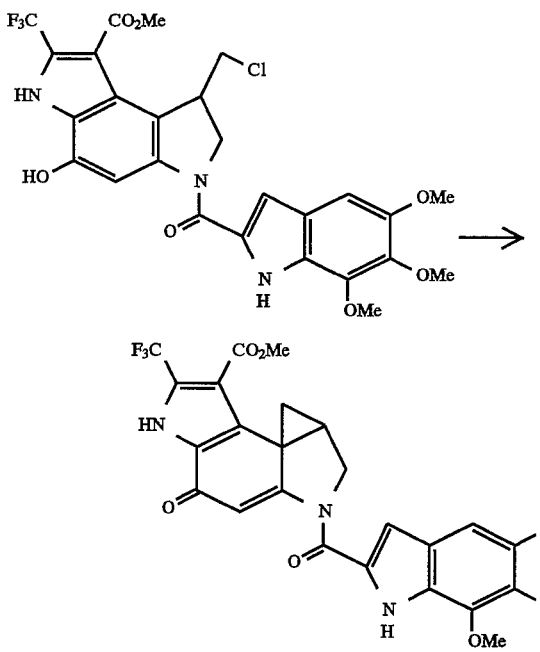

In 2.2 ml of acetonitrile, was suspended 8.0mg (14 μmol) of methyl 1-chloromethyl-5-hydroxy-7-trifluoromethyl-3-(5,6,7-trimethoxy1H-indol-2-ylcarbonyl)-1,2,3,6-tetrahydropyrrolo[3,2-e]indole-8-carboxylate. Thereto 4 μl of 1,8-diazabicyclo[5.4.0]-7-undecene was added, and the mixture was stirred under atmosphere of argon for 3 hours. Then 0.5M phosphate buffer solution was added thereto, and the mixture was extracted with ethyl acetate. The extract was washed with water, and saturated sodium chloride solution successively, and was dried over anhydrous sodium sulfate. The solvent was removed by distillation, and the residue was purified by silica gel column chromatography (methylene chloride:ethyl acetate=1:1). Thereby, methyl 6-trifluoromethyl-2-(5,6,7-trimethoxy1H-indol-2-ylcarbonyl)-1,2,8,8a-tetrahydrocyclopropa[c]-pyrrolo[3,2e]indole-4 (5H)-one-7-carboxylate was prepared in a pale yellow crystalline state in a yield of 6.6 mg (89%).

NMR (CDCl$_3$) δ: 1.42(1H, t, J=4 Hz), 2.38(1H, dd, J=4 Hz, J=8 Hz), 3.68(1H, m), 3.87(3H, s), 3.89(3H, s), 3.94(3H, s), 4.07(3H, s), 4.46(2H, m), 6.80(1H, s), 6.95(1H, d, J=2 Hz), 7.15(1H, s), 9.41(1H, s)

EXAMPLE 21

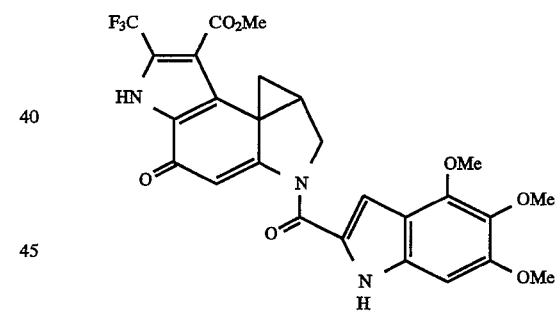

Methyl 6-trifluoromethyl-2-(4,5,6-trimethoxy1H-indol-2-ylcarbonyl)-1,2,8,8a-tetrahydrocyclopropa[c]pyrrolo[3,2-e]indol-4 (5H)-one-7-carboxylate was prepared in the same manner as above by using 7.4 mg (13 μmol) of methyl 1-chloromethyl-5-hydroxy-7-trifluoromethyl-3-(4,5,6-trimethoxy-1H-indol-2-ylcarbonyl)-1,2,3,6-tetrahydropyrrolo[3,2-e]indole-8-carboxylate in a yield of 6.7 mg (97%).

NMR (CDCl$_3$+DMSOd$_6$) δ: 1.39(1H, t, J=4 Hz), 2.33(1H, dd, J=3 Hz, J=8 Hz), 3.65(1H, m), 3.87(6H, s), 3.92(3H, s), 4.11(3H, s), 4.49(2H, m), 6.66(1H, s), 7.05(1H, s), 7.17(1H, s), 10.03(1H, s), 11.80(1H, br)

EXAMPLE 22

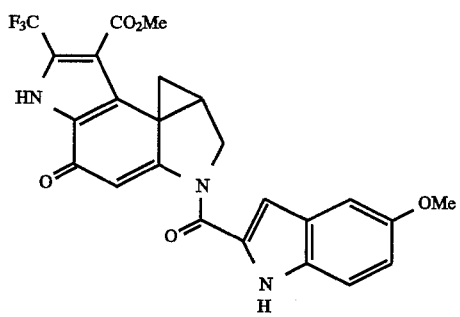

Methyl 2-(5-methoxy-1H-indol-2-ylcarbonyl)-6-trifluoromethyl-1,2,8,8a-tetrahydrocyclopropa[c]pyrrolo[3,2-e]indole-4 (5H)-one-7-carboxylate was prepared in the same manner as above by using 5.6 mg (11 μmol) of methyl 1-chloromethyl-5-hydroxy-3-(5-methoxy1H-indol-2-ylcarbonyl)-7-trifluoromethyl-1,2,3,6-tetrahydropyrrolo[3,2e]indole-8-carboxylate in a yield of 4.3 mg (82%).

NMR (CDCl$_3$+DMSOd$_6$) δ: 1.42 (1H, t, J=4 Hz), 2.31 (1H, dd, J=4 Hz, J=8 Hz), 3.62(1H, m), 3.84(3H, s), 3.86 (3H, s), 4.46(1H, d, J=10 Hz), 4.50(1H, dd, J=4 Hz, J=10 Hz), 6.94–6.96(2H, m), 7.04(2H, s), 7.41(1H, d, J=9 Hz)

EXAMPLE 23

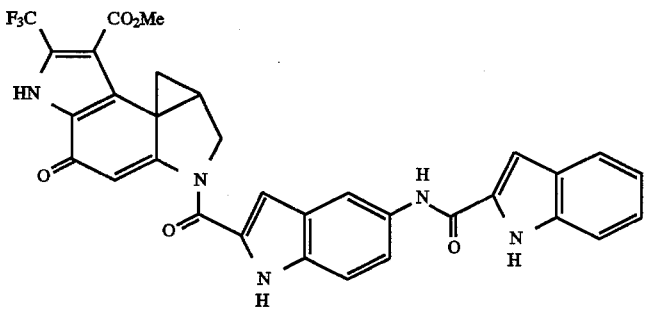

Methyl 2-[5-[(1H-indol-2-ylcarbonyl)amino]-1H-indol-2-ylcarbonyl]-6-trifluoromethyl-1,2,8,8a-tetrahydrocyclopropa[c]pyrrolo[3,2-e]indole-4 (5H)-one-7-carboxylate was prepared by using 6.0 mg (9 μmol) of methyl 1-chloromethyl-5-hydroxy-3-[5-[(1H-indol-2-ylcarbonyl)amino]-1H-indol-2-ylcarbonyl]-7-trifluoromethyl-1,2,3,6-tetrahydropyrrolo[3,2-e]indole-8-carboxylate in the same manner as above in a yield of 5.5 mg (96%).

NMR (CDCl$_3$+DMSOd$_6$) δ: 1.43 (1H, t, J=4 Hz), 2.32 (1H, dd, J=3 Hz, J=7 Hz), 3.62(1H, m), 3.86(3H, s), 4.48 (1H, d, J=10 Hz), 4.54(1H, dd, J=4 Hz, J=10 Hz), 2.03(1H, s), 7.05(1H, s), 7.10(1H, t, J=7 Hz.), 7.24(1H, t, J=7 Hz), 7.35(1H, s), 7.50(1H, d, J=9 Hz), 7.51(1H, d, J=7 Hz), 7.57(1H, d, J=2 Hz), 7.66(1H, d, J=8 Hz), 8.00(1H, s), 8,23(1H, s), 9.71(1H, s), 10.95(1H, s)

EXAMPLE 24

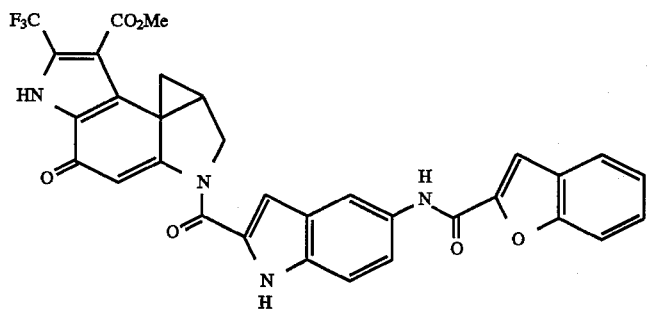

Methyl 2-[5-[(benzofuran-2-ylcarbonyl)amino]-1H-indol-2-ylcarbonyl]-6-trifluoromethyl-1,2,8,8a-tetrahydrocyclopropa[c]pyrrolo[3,2-e]indole-4 (5H)-one-7-carboxylate was prepared by using 7.3 mg. (11 μmol) of methyl 3-[5-[(benzofuran-2-ylcarbonyl)amino]-1H-indol-2-ylcarbonyl]-1- chloromethyl-5-hydroxy-7-trifluoromethyl-1,2,3,6-tetrahydropyrrolo[3,2-e]indole-8-carboxylate in the same manner as above in a yield of 5.9 mg (85%).

NMR (CDCl$_3$+DMSOd$_6$) δ: 1.41(1H, t, J=4 Hz), 2.34(1H, dd, J=3 Hz, J=8 Hz), 3.66(1H, m), 3.86(3H, s), 4.46–4.57 (2H, m), 7.03(1H, s), 7.15(1H, s), 7.33(1H, m), 7.46(1H, t, J=7 Hz), 7.50(2H, s), 7.58–7.61(2H, m), 7.72(1H, d, J=8Hz), 8.26(1H, s), 8.75(1H, s), 10.63(1H, s), 12.30(1H, br)

EXAMPLE 25

EXAMPLE 26

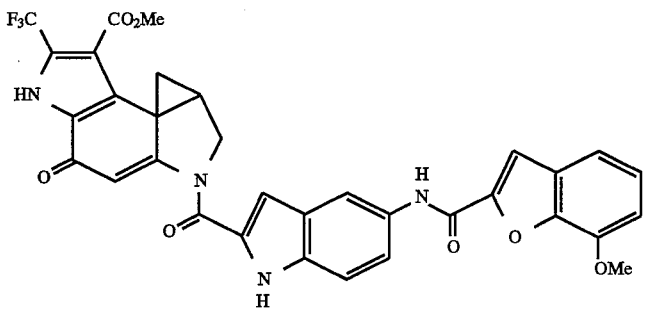

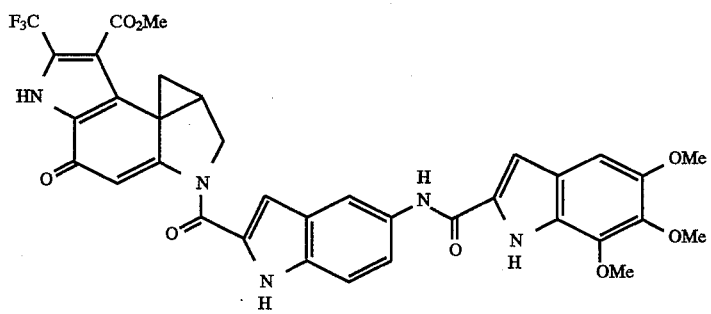

Methyl 2-[5-[(7-methoxybenzofuran-2-ylcarbonyl)amino]-1H-indol-2-ylcarbonyl]-6-trifluoromethyl-1,2,8,8a-tetrahydrocyclopropa[c]pyrrolo[3,2-e]indole-4 (5H)-one-7-carboxylate was prepared by using 9.6 mg (14 μmol) of methyl 1-chloromethyl-5-hydroxy-3-[5-[(7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate in the same manner as above in a yield of 8.5 mg (94%).

NMR (CDCl$_3$+DMSOd$_6$) δ: 1.42 (1H, t, J=4 Hz), 2.34 (1H, dd, J=4 Hz, J=8 Hz), 3.66(1H, m), 3.87(3H, s), 4.07 (3H, s), 4.51(2H, m), 6.96(1H, d, J=8 Hz), 7.04(1H, s), 7.16(1H, s), 7.26(1H, t, J=7 Hz), 7.30(1H, d, J=8 Hz), 7.50(2H, m), 7.60(1H, s), 8.24(1H, s), 8.72(1H, s), 10.60 (1H, s), 12.30(1H, br)

Methyl 3-(5-(benzofuran-2-yl)-1H-indol-2-ylcarbonyl)-6-trifluoromethyl-1,2,8,8a-tetrahydrocyclopropa[c]pyrrolo[3,2-e]indole-4 (5H)-one-7-carboxylate was prepared by using 8.3 mg (14 μmol) of methyl 3-(5-(benzofuran-2-yl)-1H-indol-2-ylcarbonyl)-1-chloromethyl-5-hydroxy-7-trifluoromethyl-1,2,3,6-tetrahydropyrrolo[3,2-e]indole-8-carboxylate in the same manner as above in a yield of 7.6 mg (98%).

NMR (CDCl$_3$+DMSOd$_6$) δ: 1.43(1H, t, J=4 Hz), 2.35(1H, dd, J=4 Hz, J=8 Hz), 3.66(1H, m), 3.87(3H, s), 4.51(2H, m), 6.99(1H, s), 7.09(1H, s), 7.13(1H, s), 7.21–7.29(2H, m), 7.52(1H, d, J=7 Hz), 7.57(1H, s), 7.59(1H, s), 7.81(1H, dd, J=2 Hz, J=9 Hz), 8.21(1H, s), 10.92(1H, s), 12.40(1H, br)

EXAMPLE 27

Methyl 6-trifluoromethyl-2-[5-[(5,6,7-trimethoxy-1H-indol-2-ylcarbonyl)amino]-1H-indol-2-ylcarbonyl]-1,2,8,8a-tetrahydrocyclopropa[c]pyrrolo[3,2-e]indole-4 (5H)-one-7-carboxylate was prepared by using 11.6 mg (16 μmol) of methyl 1-chloromethyl-5-hydroxy-7-trifluoromethyl-3-[5-(5,6,7-trimethoxy1H-indol-2-ylcarbonyl)amino]1H-indol-2-ylcarbonyl]-1,2,3,6-tetrahydropyrrolo[3,2-e]indole-8-carboxylate in the same manner as above in a yield of 8.8 mg (79%).

NMR (CDCl$_3$+DMSOd$_6$) δ: 1.42(1H, dd, J=4 Hz, J=4 Hz), 2.33(1H, dd, J=4 Hz, J=8 Hz), 3.65(1H, m), 3.86(3H, s), 3.91(3H, s), 3.94(3H, s), 4.10(3H, s), 4.49(1H, d, J=10.3 Hz), 4.53(1H, dd, J=4 Hz, 10 Hz), 6.86(1H, s), 7.02(1H, s), 7.11(1H, s), 7.23(1H, s), 7.48(1H, d, J=10 Hz), 7.53(1H, dd, J=2 Hz, 9 Hz), 8.25(1H, s), 9.49(1H, s), 10.23(1H, s), 10.85(1H, s), 12.71(1H, br)

Methyl 3-[5-[(naphthalene-3-ylcarbonyl)amino]1H-indol-2-ylcarbonyl]-6-trifluoromethyl-1,2,8,8a-tetrahydrocyclopropa[c]pyrrolo[3,2-e]indol-4 (5H)-one-7-carboxylate was prepared by using 8.1 mg (12 μmol) of methyl 1-chloromethyl-5-hydroxy-3-[5-[(naphthalene-3-ylcarbonyl)amino]-1H-indol-2-ylcarbonyl[-7-trifluoromethyl-1,2,3,6-tetrahydropyrrolo[3,2-e]indole-8-carboxylate in the same manner as above in a yield of 7.0 mg (92%).

NMR (CDCl$_3$+DMSOd$_6$) δ: 1.42(1H, t, J=4 Hz), 2.33(1H, dd, J=4 Hz, J=7 Hz), 3.65(1H, m), 3.87(1H, s), 4.51(2H, m), 7.04(1H, m), 7.13(1H, s), 7.50(1H, d, J=9 Hz), 7.57–7.59 (3H, m), 7.91(1H, d, J=8 Hz), 7.95(1H, d, J=9 Hz), 7.99(1H, d, J=7 Hz), 8.06(1H, d, J=8 Hz), 8.28(1H, s), 8.53(1H, s), 9.38(1H s), 10.72(1H, s), 12.60(1H, br)

EXAMPLE 28

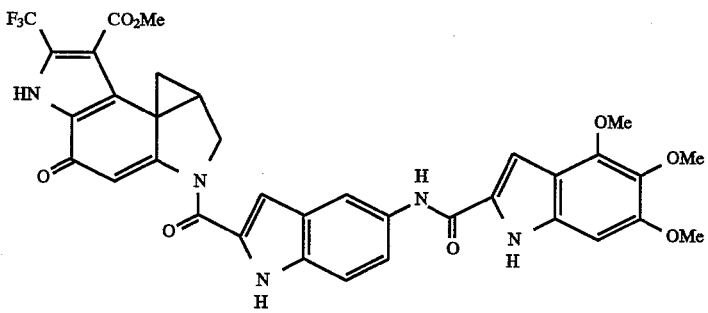

Methyl 6-trifluoromethyl-2-[5-[(4,5,6-trimethoxy-1-H-indol-2-ylcarbonyl)amino]-1H-indol-2-ylcarbonyl]-1,2,8,8a-tetrahydrocyclopropa[c]pyrrolo[3,2-e]indole-4 (5H)-one-7-carboxylate was prepared by using 6.5 mg(8.8 μmol) of methyl 1-chloromethyl-5-hydroxy-7-trifluoromethyl-3-[5 [(4,5,6-trimethoxy1H-indol-2-ylcarbonyl)amino]-1H-indol-2-ylcarbonyl]-1,2,3,6-tetrahydropyrrolo[3,2-e]indole-8-carboxylate in the same manner as above in a yield of 6.1 mg 98%).

NMR (CDCl$_3$+DMSOd$_6$) δ: 1.42(1H, t, J=4 Hz), 2.34(1H, dd, J=4 Hz, J=8 Hz), 3.66(1H, m), 3.866(3H, s), 3.875(3H, s) 3.88(3H, s), 4.14(3H, s), 4.50(2H, s), 6.66(1H, s), 7.01 (1H, s), 7.16(1H, s), 7.33(1H, s), 7.45(1H, d, J=8 Hz), 7.51(1H, d, J=8 Hz), 8.22(1H, s), 8.93(1H, s), 9.97(1H, s), 9.97(1H, s), 10.32(1H, s), 11.86(1H, br)

EXAMPLE 29

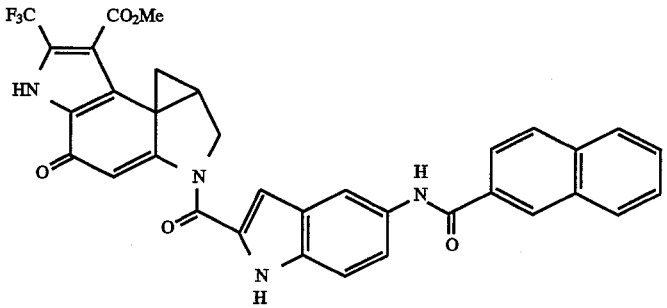

EXAMPLE 30

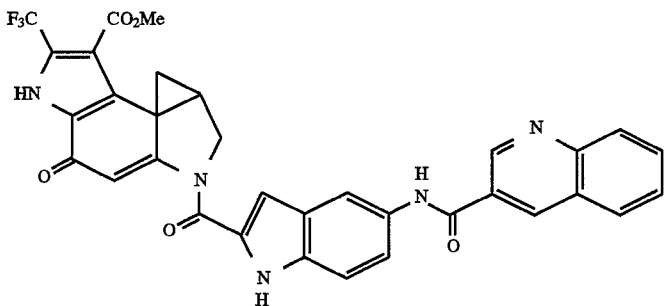

Methyl 3-[5-[(quinoline-3-ylcarbonyl)amino]-1H-indol-2-ylcarbonyl]-6-trifluoromethyl-1,2,8,8a-tetrahydrocyclopropa[c]pyrrolo[3,2-e]indol-4 (5H)-one-7-carboxylate was prepared by using 4.7 mg (7.1 μmol) of methyl 1-chloromethyl-5-hydroxy-3-[5-[(quinoline-3-ylcarbonyl)amino]-1-indol-2ylcarbonyl]-7-trifluoromethyl-1,2,3,6-tetrahydropyrrolo[3,2-e]indole-8-carboxylate in the same manner as above in a yield of 4.1 mg (93%).

NMR (CDCl$_3$+DMSOd$_6$) δ: 1.44(1H, t, J=4 Hz), 2.32(1H, dd, J=4 Hz, J=8 Hz), 3.64(1H, m), 3.86(3H, s), 4.49–4.60 (2H, m), 7.06(1H, s), 7.53–7.69(3H, m), 7.84(1H, t, J=7 Hz), 8.00(1H, d, J=8 Hz), 8.15(1H, d, J=8 Hz), 8.26(1H, s), 8.9(1H, s), 9.50(1H, s), 10.27(1H, s), 11.38(1H, s), 11.46 (1H, s), 13.15(1H, br)

EXAMPLE 31

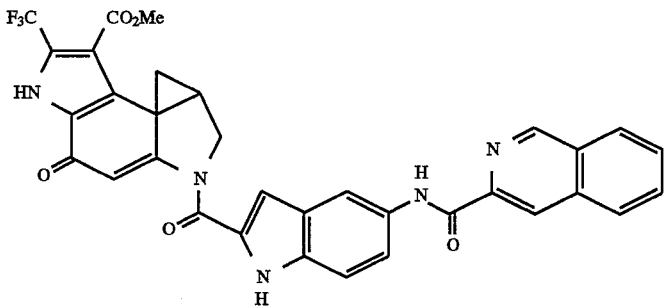

Methyl 3-[5-[(isoquinolin-3-ylcarbonyl)amino]-1H-indol-2-ylcarbonyl]-6-trifluoromethyl-1,2,8,8a-tetrahydrocyclopropa[c]pyrrolo[3,2-e]indol-4 (5H)-one-7-carboxylate was prepared by using 5.3 mg (8 μmol) of methyl 1-chloromethyl-5-hydroxy-3-[5-[(isoquinolin-3-ylcarbonyl) amino]-1H-indol-2-ylcarbonyl]-7-trifluoromethyl-1,2,3,6-tetrahydropyrrolo[3,2-e]indole-8-carboxylate in the same manner as above in a yield of 4.9 mg (97%).

NMR (CDCl$_3$+DMSOd$_6$) δ: 1.42(1H, t, J=4 Hz), 2.34(1H, dd, J=4 Hz, J=8 Hz), 3.67(1H, m), 3.87(3H, s), 4.50–4.56 (2H, m), 7.06(1H, s), 7.17(1H, s), 7.52(1H, d, J=9 Hz), 7.57(1H, dd, J=8 Hz), 7.75(1H, t, J=7 Hz), 7.80(1H, t, J=7 Hz), 8.05(1H, d, J=8 Hz), 8.10(1H, d, J=8 Hz), 8.41(1H, d, J=2 Hz), 8.74(1H, s), 9.25(1H, s), 10.30(1H, s), 10.46(1H, s), 12.20(1H, s)

EXAMPLE 32

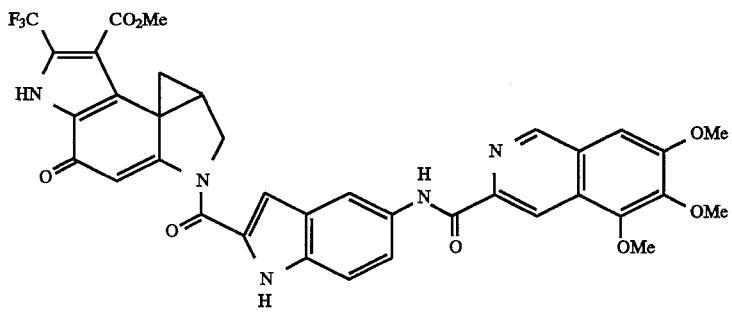

33

Methyl 6-trifluoromethyl-2-[5-[(5,6,7-trimethoxyisoquinolin-3-ylcarbonyl)amino]-1H-indol-2-ylcarbonyl]-1,2,8,8a-tetrahydrocyclopropa[c]pyrrolo[3,2e]indol-4 (5H)-one-7-carboxylate was prepared by using 12.8 mg (17 μmol) of methyl 1-chloromethyl-5-hydroxy-7-trifluoromethyl- 3-[5-[(5,6,7-trimethoxyisoquinolin-3-ylcarbonyl)amino]-1H-indol-2-ylcarbonyl]-1,2,3,6-tetrahydropyrrolo[3,2-e]indole-8-carboxylate in the same manner as above in a yield of 11.2 mg (92%).

NMR (CDCl$_3$+DMSOd$_6$) δ: 1.42(1H, t, J=4 Hz), 2.32(1H, dd, J=4 Hz, J=8 Hz), 3.65(1H, m), 3.86(3H, s), 4.05(3H, s), 4.07(3H, s), 4.11(3H, s), 4.50(1H, d, J=10 Hz), 4.55(1H, dd, J=4 Hz, J=10 Hz), 7.04(1H, s), 7.11(1H, s), 7.46(1H, s), 7.53(1H, d, J=9 Hz), 7.57(1H, dd, J=2 Hz, J=9 Hz), 8.37(1H, s), 8.84(1H, s), 9.06(1H, s), 10.26(1H, s), 11.11(1H, s), 12.85(1H, br)

EXAMPLE 33

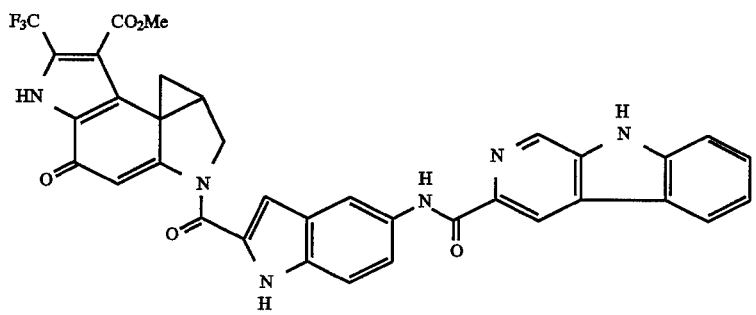

Methyl 2-[5-[(9H-pyrido[3,4-b]indol-3-ylcarbonyl)amino]-1H-indol-2-ylcarbonyl]-6-trifluoromethyl-1,2,8,8a-tetrahydrocyclopropa[c]pyrrolo[3,2-e]indol-4 (5H)-one-7-carboxylate was prepared by using 10.2 mg (15 μmol) of methyl 1-chloromethyl-5-hydroxy-3-[5-[(9H-pyrido[3,4-b]indol-3-ylcarbonyl)amino]-1H-indol-2-ylcarbonyl]-7-trifluoromethyl-1,2,3,6-tetrahydropyrrolo[3,2-e]indole-8-carboxylate in the same manner, as above in a yield of 8.4 mg (87%).

NMR (CDCl$_3$+DMSOd$_6$) δ: 1.42(1H, t, J=4 Hz), 2.33(1H, dd, J=4 Hz, J=7 Hz), 3.65(1H, m), 3.86(3H, s), 4.53(2H, m), 7.05(1H, m), 7.15(1H, s), 7.33(1H, t, J=8 Hz), 7.53–8.23 (1H, d, J=8Hz), 8.39(1H, s), 8 88(1H, s), 9.01(1H, s), 10.24(1H, s), 10.73(1H, s), 11.00(1H, s), 12.60(1H, br)

EXAMPLE 34

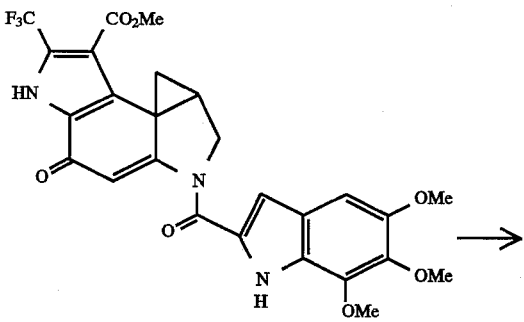

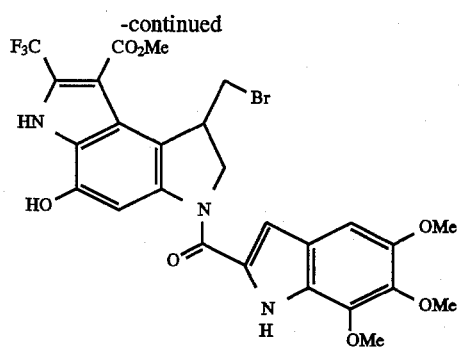

In 1 ml of acetonitrile, was dissolved 4.6 mg (9 μmol) of methyl 6-trifluoromethyl-2-(5,6,7-trimethoxy-1H-indol-2-ylcarbonyl)-1,2,8,8a-tetrahydrocyclopropa[c]pyrrolo[3,2-e]indol-4 (5H)-one-7-carboxylate. Thereto 0.5 ml of 1M hydrobromic acid was added, and the mixture was stirred for 6 hours. Then 1 ml of aqueous 0.5M potassium dihydrogenphosphate solution was added thereto, and the mixture was extracted with methylene chloride. The extract was washed with water, and saturated sodium chloride solution successively, and was dried over anhydrous sodium sulfate. The solvent was removed by distillation, and the residue was purified by silica gel column chromatography (hexane:ethyl acetate=1:2). Thereby, methyl 1-bromomethyl-5-hydroxy-7-trifluoromethyl-3-(5,6,7-trimethoxy-1H-indol-2-ylcarbonyl)-1,2,3,6-tetrahydropyrrolo[3,2e]indole-8-carboxylate was prepared in a pale yellow crystalline state in a yield of 4.7 mg (89%).

NMR (CDCl$_3$+DMSOd$_6$) δ: 3.21(1H, t, J=10 Hz), 3.76 (1H, m), 3.92(3H, s), 3.95(3H, s), 3.99(3H, s), 4.09(3H, s), 4.50–4.56(2H, m), 4.71(1H, d, J=9 Hz), 6.90(1H, s), 6.99 (1H, d, J=2 Hz), 8.01(1H, s), 9.19(1H, s), 9.48(1H, s), 11.45(1H, s)

EXAMPLE 35

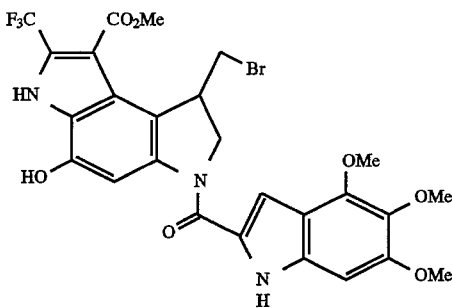

Methyl 1-bromomethyl-5-hydroxy-7-trifluoromethyl-3 (4,5,6-trimethoxy1H-indol-2-ylcarbonyl)-1,2,3,6-tetrahydropyrrolo[3,2-e]indole-8-carboxylate was prepared by using 4.8 mg(9 μmol) of methyl 6-trifluoromethyl-2-(4, 5,6-trimethoxy-1H-indol-2-ylcarbonyl)-1,2,8,8a-tetrahydrocyclopropa[c]pyrrolo[3,2-e]indol-4 (5H)-one-7-carboxylate in the same manner as above in a yield of 5.3 mg (97%).

NMR (CDCl$_3$ +DMSOd$_6$ ) δ: 3.23(1H, t, J=10 Hz), 3.76(1H, dd, J=2 Hz, J=10 Hz), 3.86(3H, s), 3.88(3H, s), 3.99(3H, s), 4.15(3H, s), 4.49–4.59(2H, m), 4.73(1H, d, J=10 Hz), 6.67(1H, s), 7.10(1H, d, J=2 Hz), 8.06(1H, s),9.11(1H, s), 9.84(1H, s), 11.32(1H, s)

EXAMPLE 36

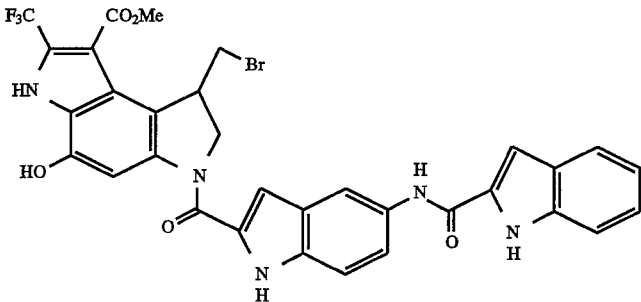

Methyl 1-bromomethyl-5-hydroxy-3-[5-[(1H-indol-2-ylcarbonyl)amino]-1H-indol-2-ylcarbonyl)-7-trifluoromethyl-1,2,3,6-tetrahydropyrrolo[3,2-e]indole-8-carboxylate was prepared by using 3.7 mg (6 μmol) of methyl 2-[5-[(1H-indol-2-ylcarbonyl)amino]-1H-indol-2-ylcarbonyl]-6-trifluoromethyl-1,2,8,8a-tetrahydrocyclopropa[c]pyrrolo[3,2e]indol-4 (5H)-one-7-carboxylate in the same manner as above in a yield of 3.9 mg(93%).

NMR (CDCl$_3$+DMSOd$_6$) δ: 3.23(1H, t, J=10 Hz), 3.77 (1H, m), 3.99(3H, s), 4.52–4.60(2H, m), 4.75(1)t, d, J=10 Hz), 7.07(1H, s), 7.15(1H, t, J=8 Hz), 7.24(1H, br, s), 7.28–7.33(1H, m), 7.46–7.50(2H, m), 7.53(1H, dd, J=2 Hz, J=9 Hz), 7.70(1H, d, J=8Hz), 8.02(1H, s), 8.21(1H, s), 8.94(1H, s), 9.12(1H, s),9.87(1H, s), 10.00(1H, s), 11.38 (1H, s)

EXAMPLE 37

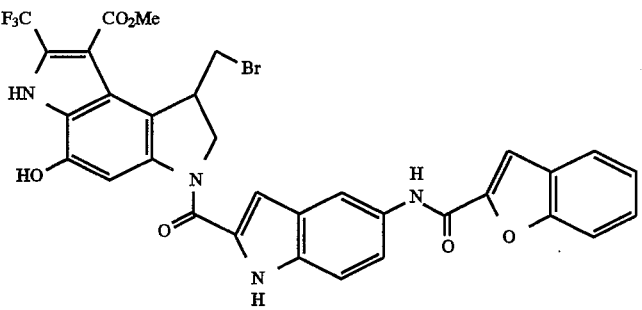

Methyl 3-[5-[(benzofuran-2-ylcarbonyl)amino]-1H-indol-2-ylcarbonyl]-1-bromomethyl-5-hydroxy-7-trifluoromethyl-1,2,3,6-tetrahydropyrrolo[3,2-e]indole-8- carboxylate was prepared by using 9.4 mg (15 μmol) of methyl 2-[5-[(benzofuran-2-ylcarbonyl)amino]-1H-indol-2-ylcarbonyl]-6-trifluoromethyl-1,2,8,8a-tetrahydrocyclopropa[c]pyrrolo[3,2-e]indol-4 (5H)-one-7-carboxylate in the same manner as above in a yield of 9.2 mg (86%).

NMR (CDCl$_3$+DMSOd$_6$) δ: 3.24(1H, t J=10 Hz), 3.78 (1H, m), 4.00(3H, s), 4.51–4.61(2H, m), 4.75(1H, d, J=10 Hz), 7.09(1H, s), 7.31–7.36(2H, m), 7.47(1H, t, J=7 Hz), 7.51(1H, s), 7.59–7.62(2H, m), 7.72(1H, d, J=8 Hz), 8.02 (1H, br, s), 8.25(1H, s), 8.64(1H, s), 9.13(1H, s), 9.94(1H, s), 11.39(1H, s)

EXAMPLE 38

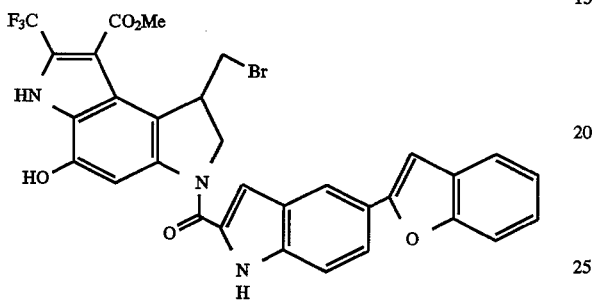

Methyl 3-(5-(benzofuran-2-y1)-1H-indol-2-ylcarbonyl)-1-bromomethyl-5-hydroxy-7-trifluoromethyl-1,2,3,6-tetrahydropyrrolo[3,2-e]indole-8-carboxylate was prepared by using 5.6 mg (10 μmol) of methyl 3-(5(benzofuran-2-yl)-1H-indol-2-ylcarbonyl)-6-trifluoromethyl-1,2,8,8a-tetrahydrocyclopropa[c]pyrrolo[3,2-e]indol-4 (5H)-one-7-carboxylate in the same manner as above in a yield of 6.2 mg (98%).

NMR (CDCl$_3$+DMSOd$_6$) δ: 3.24(1H, t, J=10 Hz), 3.77 (1H, m), 3.99(3H, s), 4.52–4.62(2H, m), 4.76(1H, d, J=10 Hz), 7.00(1H, s), 7.14(1H, s), 7.21–7.28(2H, m), 7.53(1H, d, J=8 Hz), 7.58(1H, d, J=8.3 Hz), 7.81(1H, d, J=9 Hz), 8.02(1H, s), 8.27(1H, s), 9.21(1H, d, J=2 Hz), 10.40(1H, br, s), 10.80(1H, br), 11.57(1H, br, s)

EXAMPLE 39

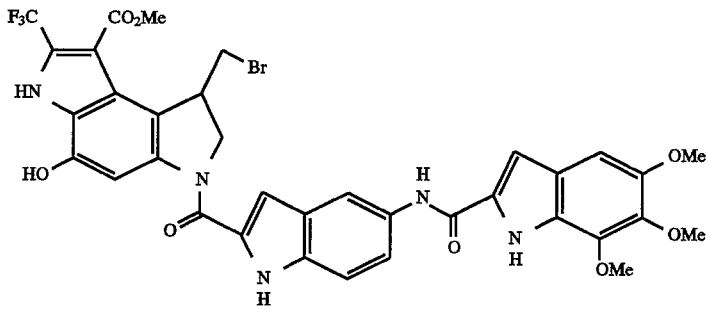

Methyl 1-bromomethyl-5-hydroxy-7-trifluoromethyl-3-[5[(5,6,7-trimethoxy1H-indol-2-ylcarbonyl)amino]-1H-indol-2-ylcarbonyl]-1,2,3,6-tetrahydropyrrolo[3,2-e]indole-8-carboxylate was prepared by using-6.0 mg (9 μmol) of methyl 6-trifluoromethyl-2-[5-[(5,6,7-trimethoxy-1H-indol-2-ylcarbonyl)amino]-1H-indol-2-ylcarbonyl]-1,2,8,8a-tetrahydrocyclopropa[c]pyrrolo[3,2-e]indol-4 (5H)-one-7-carboxylate in the same manner as above in a yield of 6.5 mg (97%).

NMR (CDCl$_3$+DMSOd$_6$) δ: 3.24(1H, t, J=10 Hz), 3.76 (1H, m), 3.91(3H, s), 3.94(3H, s), 3.99(3H, s), 4.10(3H, s), 4.49–4.60(2H, m), 4.74(1H, d, J=10 Hz), 6.86(1H, s), 7.05 (1H, s), 7.23(1H, s), 7.48(1H, d, J=9 Hz),7.54(1H, dd, J=2 Hz, J=9 Hz), 8.01(1H, br, s), 8.21(1H, s), 9.40(1H, s), 10.16(1H, s), 10.27(1H, s),

EXAMPLE 40

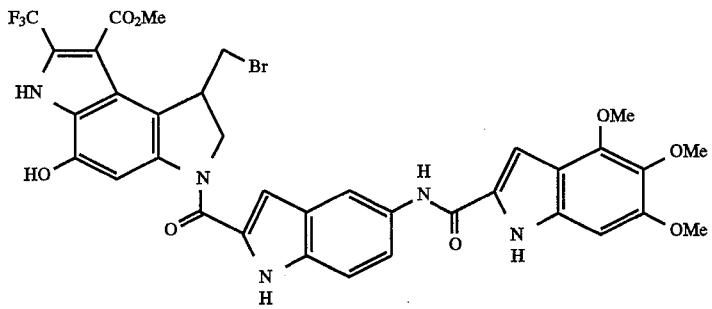

Methyl 1-bromomethyl-5-hydroxy-7-trifluoromethyl-3-[5-[(4,5,6-trimethoxy1H-indol-2-ylcarbonyl)amino]-1H-indol-2-ylcarbonyl]-1,2,3,6-tetrahydropyrrolo[3,2-e]indole-8-carboxylate was prepared by using 3.8 mg (5 μmol) of methyl 6-trifluoromethyl-2-[5-[(4,5,6-trimethoxy1H-indol-2-ylcarbonyl)amino]-1H-indol-2-ylcarbonyl]-1,2,8,8a-tetrahydrocyclopropa[c]pyrrolo[3,2-e]indol-4 (5H)-one-7-carboxylate in the same manner as above in a yield of 4.2 mg (99%).

NMR (CDCl$_3$+DMSOd$_6$) δ: 3.22(1H, t, J=10 Hz), 3.76 (1H, m), 3.84(3H, s), 3.87(3H, s), 3.98(3H, s), 4.14(3H, s), 4.50–4.57(2H, m), 4.73(1H, d, J=10 Hz), 6.66(1H, s), 7.04 (1H, s), 7.34(1H, s), 7.44(1H, d, J=8 Hz),7.51(1H, d, J=8 Hz), 8.05(1H, br, s), 8.19(1H, s), 8.98(1H, s), 9.18(1H, s), 10.12(2H, br, s), 11.42(1H, s)

EXAMPLE 41

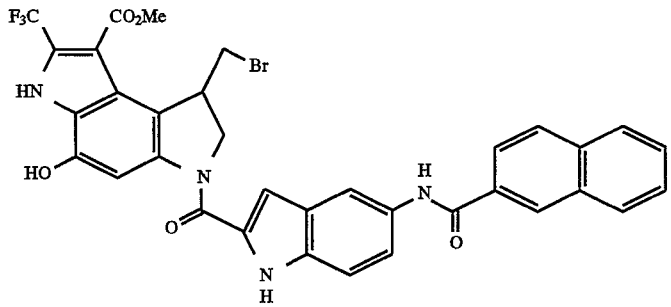

Methyl 1-bromomethyl-5-hydroxy-3-[5-[(naphthalene-3-ylcarbonyl)amino]-1H-indol-2-ylcarbonyl]-7-trifluoromethyl-1,2,3,6-tetrahydropyrrolo[3,2-e]indole-8-carboxylate was prepared by using 2.9 mg(5 μmol) of methyl 3-[5-[(naphthalene-3-ylcarbonyl)amino]-1H-indol-2-ylcarbonyl]-6-trifluoromethyl-1,2,8,8a-tetrahydrocyclopropa[c]pyrrolo[3,2e]indol-4 (5H)-one-7-carboxylate in the same manner as above in a yield of 3.2 mg (97%).

NMR(CDCl$_3$+DMSOd$_6$) δ; 3.23(1H, t, J=10 Hz), 3.77 (1H, m), 3.99(3H, s), 4.49(1H, m), 4.58(1H, t J=10 Hz), 4.74(1H, d, J=11Hz),7.50(1H, d, J=9 Hz), 7.55–7.60(3H, m), 7.91(1H, d, J=7 Hz), 7.95(1H, d, J=8 Hz), 7.99(1H, d, J=7 Hz), 8.07(1H, d, J=8 Hz), 8.25(1H, s), 8.53(1H, s), 9.27(1H, s),9.35(1H, s,), 10.23 (1H, s), 10.94(1H, s), 11.61 (1H, s)

EXAMPLE 42

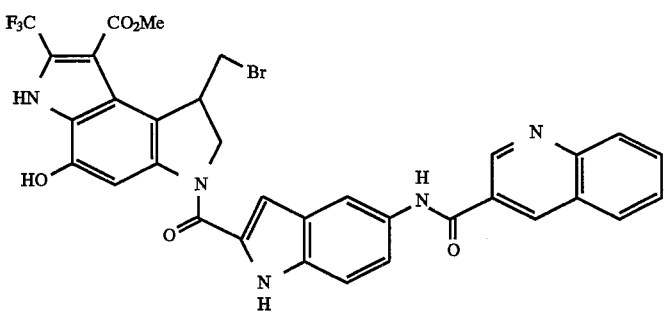

Methyl 1-bromomethyl-5-hydroxy-3-[5-[(quinoline-3-ylcarbonyl)amino]-1H-indol-2-yl carbonyl]-7-trifluoromethyl-1,2,3,6-tetrahydropyrrolo[3,2-e]indole-8-carboxylate was prepared by using 2.7 mg (4 μmol) of methyl 3-[5-[(quinoline-3-ylcarbonyl)amino]-1H-indol-2-ylcarbonyl]-6-trifluoromethyl-1,2,8,8a-tetrahydrocyclopropa[c]pyrrolo[3,2-e]indol-4 (5H)-one-7-carboxylate in the same manner as above in a yield of 2.6 mg(84%).

NMR (CDCl$_3$+DMSOd$_6$) δ: 3.24(1H, t, J=10 Hz), 3.76 (1H, m), 3.99(3H, s), 4.51–4.58(2H, m), 4.75(1H, d, J=10.3 Hz), 7.06(1H, s),7.45(1H, d, J=9 Hz), 7.58(1H, d, J=8 Hz), 7.64(1H, t, J=8 Hz), 7.83(1H, t, J=8 Hz),7.97 (1H, d, J=7 Hz), 8.03(1H, br, s), 8.18(1H, d, J=8 Hz), 8.24(1H, s), 8.85(1H, s), 9.29(1H, s), 9.53(1H, s), 9.65(1H, br, s), 10.01 (1H, br, s), 11.44(1H, br, s)

Methyl 1-bromomethyl-5-hydroxy-7-trifluoromethyl-3-[5-[(5,6,7-trimethoxyisoquinolin-3-ylcarbonyl)amino]-1H-indol-2-ylcarbonyl]-1,2,3,6-tetrahydropyrrolo[3,2-e]indole-8-carboxylate was prepared by using 7.0 mg (10 μmol) of methyl 6-trifluoromethyl-2-[5-[(5,6,7-trimethoxyisoquinolin-3-ylcarbonyl)amino]-1H-indol-2-ylcarbonyl]-1,2,8,8a-tetrahydrocyclopropa[c]pyrrolo[3,2-e]indol-4 (5H)-one-7-carboxylate in the same manner as above in a yield of 7.4 mg (95%).

NMR (CDCl$_3$+DMSOd$_6$) δ: 3.25(1H, t, J=10 Hz), 3.77 (1H, m), 3.99(3H, s), 4.05(3H, s), 4.07(3H, s), 4.12(3H, s), 4.48(1H, m), 4.59(1H, t, J=8 Hz), 4.74(1H, d, J=11 Hz), 7.07(1H, s), 7.19(1H, s), 7.54(1H, d, J=9 Hz),7.60(1H, dd, J=2 Hz, J=9Hz), 7.98(1H, br, s), 8.36(1H, s), 8.85(1H, s), 9.07(1H, s), 9.39(1H, s), 10.27(1H, s), 10.66(1H, s), 11.85 (1H, s)

EXAMPLE 43

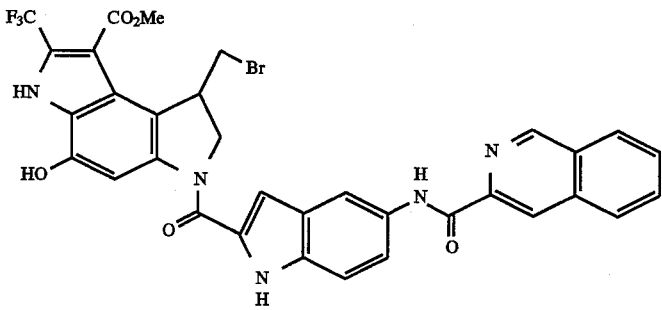

Methyl 1-bromomethyl-5-hydroxy-3-[5-[(isoquinolin-3-ylcarbonyl)amino]-1H- indol-2-ylcarbonyl]-7-trifluoromethyl-1,2,3,6-tetrahydropyrrolo[3,2-e]indole-8-carboxylate was prepared by using 3.1 mg(5 μmol) of methyl 3-[5-[(isoquinolin-3-ylcarbonyl)amino]-1H-indol-2-ylcarbonyl]-6-trifluoromethyl-1,2,8,8a-tetrahydrocyclopropa[c]pyrrolo[3,2-e]indol-4 (5H)-one-7-carboxylate in the same manner as above in a yield of 3.5 mg (98%).

NMR (CDCl$_3$+DMSOd$_6$) δ: 3.24(1H, t, J=10 Hz), 3.78 (1H, d, J=9 Hz), 8.99(8H, s), 4.51–4.59(2H, m), 4.76(1H, d, J=10 Hz), 7.09(1H, s), 7.51(1H, d, J =9 Hz),7.62(1H, d, J=9 Hz),7.76(1H, t, J=8 Hz),7.88(1H, t, J=8 Hz),8.03–8.12(4H, m), 8.40(1H, s), 8.80(1H, s), 9.26(1H, s), 10.02(1H, br), 10.34(1H, s), 11.44(1H, s)b

EXAMPLE 44

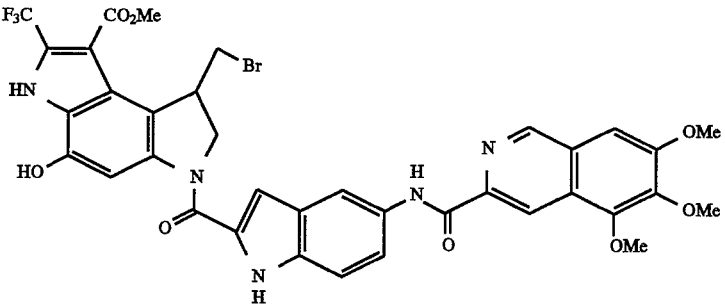

EXAMPLE 45

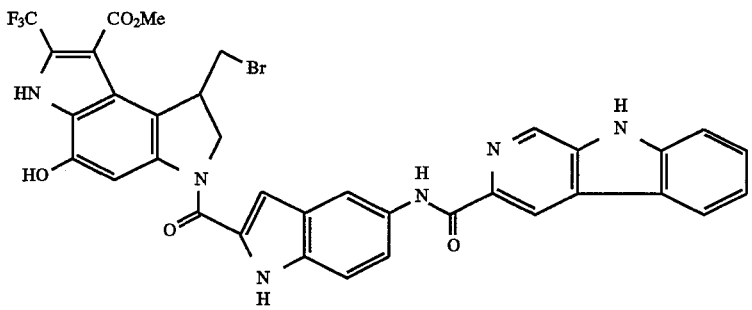

Methyl 1-bromomethyl-5-hydroxy-3-[5-[(9H-pyrido[3,4-b]indol-3-ylcarbonyl)amino]-1H-indol-2-yl carbonyl]-7-trifluoromethyl-1,2,3,6-tetrahydropyrrolo[3,2-e]indole-8-carboxylate was prepared by using 5.9 mg (9 µmol) of methyl 2-[5-[(9H-pyrido[3,4-b]indol-3-ylcarbonyl)amino] 1H-indol-2-ylcarbonyl]-6-trifluoromethyl-1,2,8,8a-tetrahydrocyclopropa[c]pyrrolo[3,2-e]indol-4 (5H)-one-7-carboxylate in the same manner as above in a yield of 6.4 mg (96%).

NMR (CDCl$_3$+DMSOd$_6$) δ: 3.24(1H, t, J=10 Hz), 3.76 (1H, m), 3.99(3H, s), 4.51(1H, m), 4.57(1H, t, J=10 Hz), 4.76(1H, d, J=11 Hz), 7.10(1H, s), 7.33(1H, m), 7.51(1H, d, J=9 Hz), 7.54–7.67(3H, m), 8.03(1H, br, s), 8.23(1H, (1H, s), 8.88(1H, s), 9.02(1H, s), 9.25(1H, s), 10.10(1H, br), 10.24(1H, s), 10.80(1H, br), 11.51(1H, br)

EXAMPLE 46

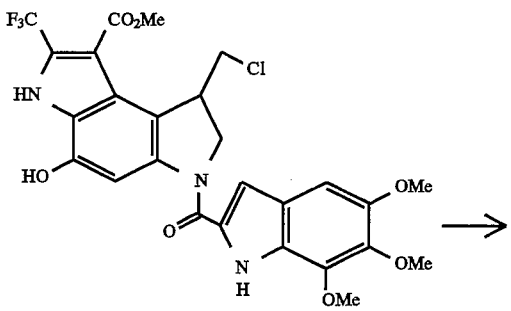

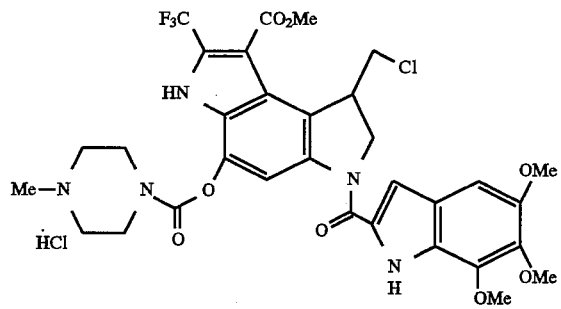

5.0 Milligrams (9µmol) of methyl 1-chloromethyl-5-hydroxy-7-trifluoromethyl-3-(5,6,7-trimethoxy1H-indol-2-ylcarbonyl)-1,2,3,6-tetrahydropyrrolo[3,2-e]indol-8-carboxylate was suspended in methylene chloride. Thereto, 2.3 mg (11 µmol) of p-nitrophenyl chloroformate and 1.6 µl (11 µmol) of triethylamine was added, and the mixture was stirred under ice cooling for 50 minutes. Further thereto, 1.4 µl (13 µmol) of N-methylpiperazine was added and the mixture was stirred overnight at room temperature.

The reaction mixture was diluted with chloroform. The diluted mixture was washed with water, 10% sodium hydrogencarbonate, and water successively, and dried over anhydrous sodium sulfate. The solvent was distilled off, and the residue was purified by silica gel column chromatography (chloroform:methanol=8:1). Thereby, methyl 1-chloromethyl-5-(4-methylpiperazin-1-ylcarbonyl)oxy-7-trifluoromethyl-3-(5,6,7-trimethoxy-1H-indol-2-ylcarbonyl-1,2,3,6-tetrahydropyrrolo[3,2-e]indole-8-carboxylate in a colorless crystal state in a yield of 4.5 mg (74%).

NMR (CDCl$_3$) δ: 2.38(3H, s), 2.46–2.52(4H, m), 3.39 (1H, t, J=10 Hz), 3.59–3.72(2H, m),3.76–3.83(2H, m), 3.91 (1H, m),3.92(3H, s),3.95(3H, s), 3.99(3H, s), 4.09(3H, s), 4.54–4.62(2H, m), 4.76–4.82(1H, m), 6.89(1H, s), 7.01(1H, d, J=2 Hz), 8.36(1H, s), 9.33(1H, s), 9.57(1H, s)

To 3.0 mg(4.3 µmol) of the resulting crystal, was added 0.4 ml of 3M hydrogen chloride-ethyl acetate, and the solvent was distilled off. The residue was washed with ether to give 3.1 mg (97%) of the hydrochloride salt thereof in a colorless crystal state.

NMR (DMSOd$_6$) δ: 2.85(3H, br, s), 3.10–3.26(3H, m), 3.46–3–65(4H, m), 3.80(3H, s), 3.82(3H, s), 3.90(3H, s), 3.94(3H, s), 3.93–3.96(1H, m), 4.35–4.81(3H, m), 4.72(1H, dd, J=9Hz, J=11Hz), 6.97(1H, s), 7.04(1H, s), 8.14(1H, s), 10.78(1H, br), 11.39(1H, s), 13.16(1H, s)

EXAMPLE 47

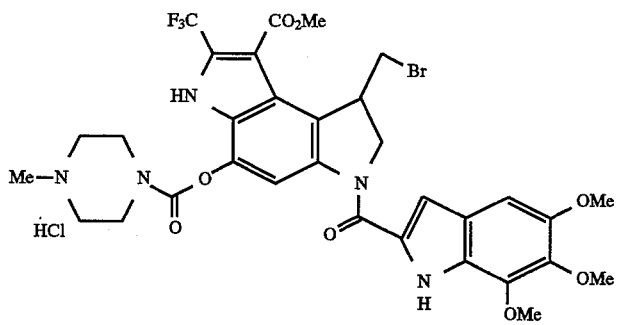

Methyl 1-bromomethyl-5-(4-methylpiperazin-1-ylcarbonyl)oxy-7-trifluoromethyl-3-(5,6,7-trimethoxy-1H-indol-2-ylcarbonyl)-1,2,3,6-tetrahydropyrrolo[3,2-e]indole-8-carboxylate was prepared by using 11.09 mg (18 μmol) of methyl 1-bromomethyl-5-hydroxy-7-trifluoromethyl-3-(5,6,7-trimethoxy-1H-indol-2-ylcarbonyl)-1,2,3,6-tetrahydropyrrolo[3,2-e]indole-8-carboxylate in the same manner as above in a yield of 6.9 mg (52%).

NMR (CDCl$_3$) δ: 2.37(3H, s), 2.47–2.58(4H, m), 3.26 (1H, t, J=10 Hz), 3.60–3.70(2H, m), 3.76–3.83(3H, m), 3.92(3H, s), 3.95(3H, s), 4.00(3H, s), 4.09(3H, s), 4.56–4.67 (2H, m), 4.77(1H, d, J=10 Hz), 6.90(1H, s), 7.01(1H, d, J=2Hz), 8.36(1H s), 9.34(1H, s), 9.59(1H, s)

Hydrochloride salt: 4.8 mg (96%)

NMR (DMSOd$_6$) δ: 2.86(3H, br, s), 3.15–3.28(3H, m), 3.43–3.70(4H, m), 3.77–3.82(1H, m), 3.81(3H, s), 3.83(3H, s), 3.92(3H, s), 3.96(3H, s), 4.16(1H, m), 4.35–4.53(3H, m), 4.72(1H, t, J=10 Hz), 6.96(1H, s), 7.03(1H, s), 8.14(1H, s), 8.30(1H, s), 11.35(1H, s), 13.12(1H, s)

NMR (CDCl$_3$) δ: 2.37(3H, s), 2.46–2.60(4H, m), 3.40 (1H, dd, 3.40(1H, dd, J=9 Hz, J=11 Hz), 3.60–3.72(2H, m), 3.77–3.92(3H, m), 3.99(3H, s), 4.56–4.67(2H, m), 4.80(1H, m), 7.08(1H, s), 7.34(1H, t, J=7 Hz), 7.42–7.49(3H, m), 7.59(1H, d J=8 Hz), 7.62(1H, s), 7.73(1H, d, J=8 Hz), 8.23(1H, s), 8.37(1H, s), 8.42(1H, s), 9.34(1H, s), 9.72(1H, s)

Hydrochloride salt: 3.5 mg (97%)

NMR (DMSOd$_6$) δ: 2.86(1H, br, s), 3.15–3.27(3H, m), 3.45–3.68(4H, m), 3.90–3.97(1H, m), 3.92(3H, s), 4.18(1H, m), 4.43(2H, br, s), 4.60(1H, d, J=11 Hz), 4.80(1H, t, J=10 Hz), 7.22(1H, s), 7.37(1H, t, J=7 Hz), 7.49–7.52(2H, m), 7.63(1H, d, J=9 Hz), 7.72(1H, d, J=8 Hz), 7.76(1H, s), 7.83(1H, d, J=7 Hz), 8.20(1h, s), 8.23(1H, s), 8.30(1H, d, J=5 Hz), 10.48(1H, br), 11.65(1H, s), 13.11(1H, br)

EXAMPLE 48

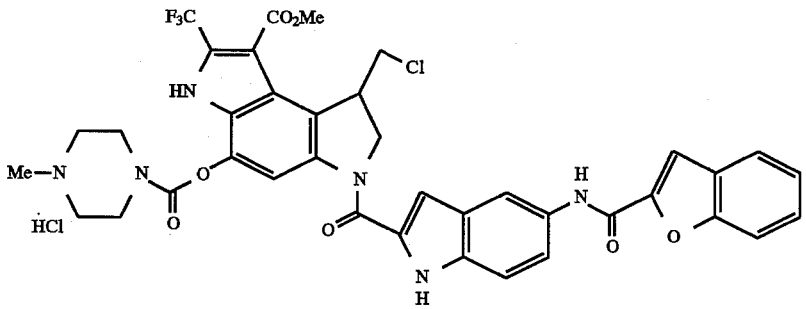

Methyl 3-[5-(benzofuran-2-ylcarbonyl)amino]-1H-indol-2-ylcarbonyl]-1-chloromethyl-5-(4-methylpiperazin-1-ylcarbonyl)oxy-7-trifluoromethyl-1,2,3,6-tetrahydropyrrolo]3,2-e]indole-8-carboxylate was prepared by using 5.0 mg (8 μmol) of methyl 3-[5-(benzofuran-2-ylcarbonyl)amino]-1H-indol-2-ylcarbonyl]-1-chloromethyl-5-hydroxy-7-trifluoromethyl-1,2,3,6-tetrahydropyrrolo[3,2-e]indole-8-carboxylate in the same manner as above in a yield of 4.8 mg(80%).

EXAMPLE 49

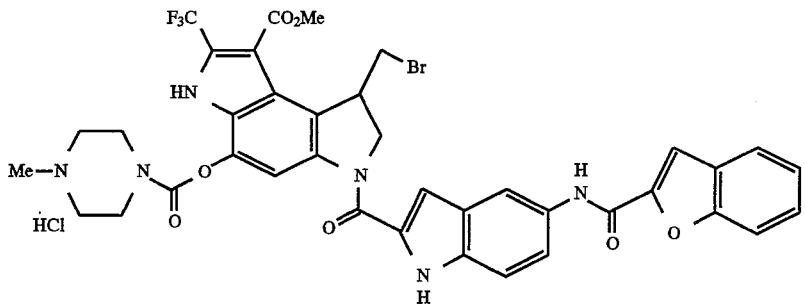

Methyl 3-[5-(benzofuran-2-ylcarbonyl)amino]-1H-indol-2-ylcarbonyl]-1-bromomethyl-5-(4-methylpiperazin-1-ylcarbonyl)oxy-7-trifluoromethyl-1,2,3,6-tetrahydropyrrolo[3,2-e]indole-8-carboxylate was prepared by using 6.9 mg (10 μmol) of methyl 3-[5-[(benzofuran-2-ylcarbonyl)amino]-1H-indol-2-ylcarbonyl]-1-bromomethyl-5-hydroxy-7-trifluoromethyl-1,2,3,6-tetrahydropyrrolo[3,2e]indole-8-carboxylate in the same manner as above in a yield of 6.8 mg(83%).

NMR (CDCl$_3$) δ: 2.37(3H, s), 2.46–2.60(4H, m), 3.27 (1H, t, J=10 Hz), 3.61–3.71(2H, m), 3.73–3.85(3H, m), 4.00(3H, s), 4.56–4.69(2H, m), 4.77(1H, d, J=9 Hz), 7.08 (1H, s), 7.34(1H, t, J=7 Hz), 7.47(3H, m), 7.59(1H, d, J=9 Hz), 7.63(1H, s), 7.73(1H, d, J=7 Hz), 8.23(1H, m), 8.37 (1H, s), 8.42(1H, s), 9.34(1H, s), 9.73(1H, br)

Hydrochloride salt: 5.4 mg (98%)

NMR (DMSOd$_6$) δ: 2.87(3H, br, s), 3.12–3.30(3H, m), 3.45–3.63(4H, m), 3.84(1H, dd, J=3Hz, J=10 Hz), 3.93(3H, s), 4.17(1H, m), 4.35–4.52(2H, m), 4.58(1H, d, J=11 Hz), 4.81(1H, t, J=10Hz), 7.21(1H, d, J=2 Hz), 7.38(1H, t, J=7 Hz), 7.49–7.53(2H, m), 7.63(1H, dd, J=2 Hz, J=9 Hz), 7.73(1H, d, J=8 Hz), 7.77(1H, s), 7.83(1H, d J=7 Hz), 8.20(1H, s), 8.23(1H, s), 8.31(1H, s), 10.49(1H, s), 11.65 (1H, br), 13.13(1H, br)

Methyl 1-chloromethyl-5-hydroxy-7-trifluoromethyl-3-[5-[(5,6,7-trimethoxycinnolin-3-ylcarbonyl)amino]-1H-indol-2-ylcarbonyl]-1,2,3,6-tetrahydropyrrolo[3,2-e]indole-8-carboxylate was prepared by using 9.7 mg (23 μmol) of 5-(5,6,7-trimethoxyisoquinolin-3-ylcarbonyl)amino-1H-indole-2-carboxylic acid in the same manner as in Example 6 in a yield of 13.4 mg (77%).

NMR (DMSOd$_6$) δ: 3.41(1H, t, J=10 Hz), 3.91(1H, d, J=10 Hz), 3.99(3H, s), 4.090(3H, s), 4.094(3H, s), 4.15(3H, s), 4.45(1H, m), 4.60(1H, t, J=10 Hz), 4.78(1H, d, J=11 Hz), 7.08(1H, s), 7.52(1H, d, J=9 Hz), 7.60(1H, d, J=9 Hz), 7.68(1H, s), 8.06(1H, brs), 8.36(1H, s), 8.97(1H, s), 9.39 (1H, br), 10.44(1H, br), 10.47(1H, s), 11.67(1H, br)

EXAMPLE 50

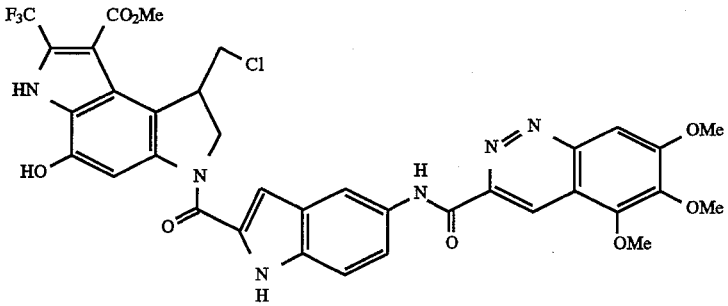

EXAMPLE 51

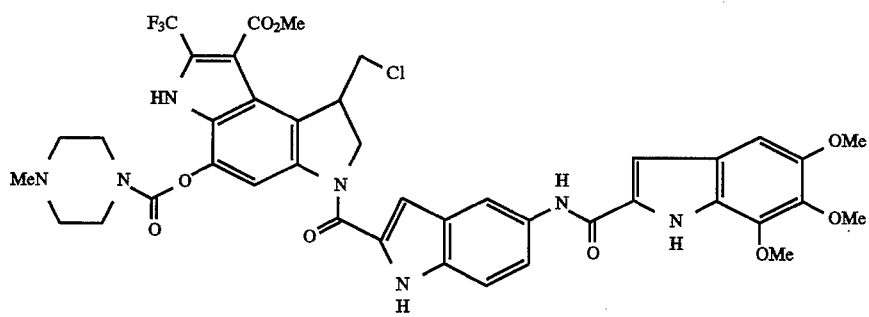

Methyl 1-chloromethyl-5-(4-methylpiperazin-1-ylcarbonyl)oxy-7-trifluoromethyl-3-[5-[(5,6,7-trimethoxy1H-indol-2-ylcarbonyl)amino]-1H-indol-2-ylcarbonyl)-1,2,3,6tetrahydropyrrolo[3,2-e]indol, e-8-carboxylate was prepared by using 12.0 mg (16 µmol) of methyl 1-chloromethyl-5-hydroxy-7-trifluoromethyl-3-[5-[(5,6,7-trimethoxy1H-indol-2-ylcarbonyl)amino]-1H-indol-2-ylcarbonyl]-1,2,3,6-tetrahydropyrrolo[3,2-e]indole-8-carboxylate in the same manner as in Example 46 in a yield of 6.3 mg (45%).

NMR (CDCl$_{13}$) δ: 2.36(3H, s), 2.52(4H, s), 3.36(1H, brs), 3.63~3.85(5H, m), 3.90(3H, s), 3.94(3H, s), 3.96(3H, s), 4.09(3H, s), 4.51~4.59(2H, m), 4.73(1H, d, J=10 Hz), 6.82 (1H, s), 7.00(1H, s), 7.13(1It, brs), 7.42~7.44(2H, m), 8.19 (1H, brs), 8.30(1H, s), 9.05(1H, brs), 9.79(1H, brs), 9.87 (1H, brs), 11.48(1H, brs)

EXAMPLE 52

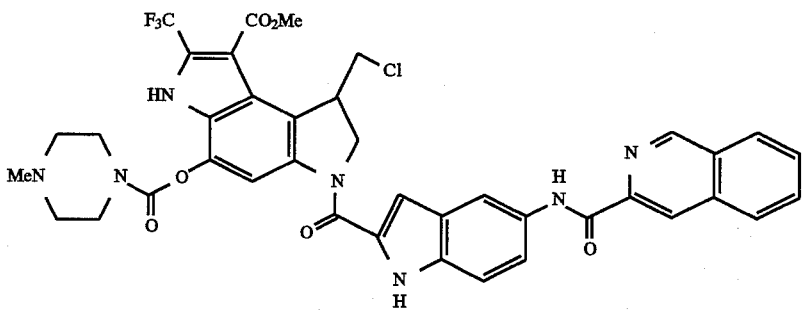

Methyl 1-chloromethyl-5-(4-methylpiperazin-1-ylcarbonyl)oxy-3-[5-[(isoquinolin-3-ylcarbonyl)amino]-1H-indol-2-ylcarbonyl)-7-trifluoromethyl-1,2,3,6-tetrahydropyrrolo[3,2-e]indole-8-carboxylate was prepared by using 7.6 mg (11 µmol) of methyl 1-chloromethyl-5-hydroxy-3-[5-[(isoquinolin-3-ylcarbonyl)amino)]-1H-indol-2ylcarbonyl]-7-trifluoromethyl-1,2,3,6-tetrahydropyrrolo[3,2-e]indole-8-carboxylate in the same manner as in Example 46 in a yield of 3.8 mg (43%).

NMR (CDCl$_3$) δ: 2.35(3H, s), 2.52(4H, s), 3.38(1H, t, J=9 Hz), 3.67(2H s), 3.83~3.87(3H, m), 3.98(3H, s), 4.56~4.62 (2H, m), 4.77(1H, d, J=9 Hz), 7.04(1H, s), 7.41(1H, d, J=9 Hz), 7.51(1H, dd, J=2Hz, J=9 Hz), 7.74(1H, t, J=7 Hz), 7.81(1H, t, J=7 Hz), 8.05(1H, d, J=8 Hz), 8.09(1H, d, J=8 Hz), 8.33.(1H, s), 8.38(1H, s), 8.76(1H, s), 9.25(1H, s), 9.41(1H, s), 10.02(1H, br), 10.27(1H, s)

EXAMPLE 53

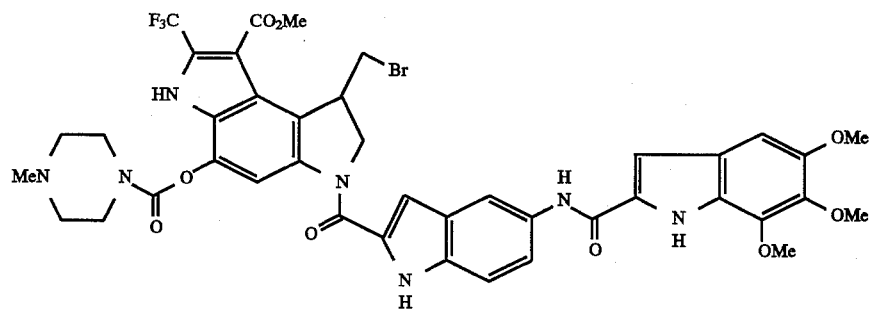

Methyl 1-bromomethyl-5-(4-methylpiperazin-1-ylcarbonyl)oxy- 7-trifluoromethyl-3-[5-[(5,6,7-trimethoxy1H-indol-2-ylcarbonyl)amino]1H-indol-2-ylcarbonyl]-1,2,3,6-tetrahydropyrrolo[3,2-e]indole-8-carboxylate was prepared by using 9.9 mg (13 μmol) of methyl 1-bromomethyl-5-hydroxy-7-trifluoromethyl-3-[5-[(5,6,7-trimethoxy-1H-indol-2-ylcarbonyl)amino]-1H-indol-2-ylcarbonyl]-1,2,3,6-tetrahydropyrrolo[3,2-e]indole-8-carboxylate in the same manner as in Example 46 in a yield of 7.0 mg (61%).

NMR (CDCl₃) δ: 2.36(3H, s), 2.53(4H, brs), 3.23(1H, brs), 3.63~3.84(5H, m), 3.91(3H, s), 3.94(3H, s), 3.98(3H, s), 4.09(3H, s), 4.58(2H, brs), 4.72(1H, d, J=9 Hz), 6.83(1H, s), 7.01(1H, s), 7.15(1H, brs), 7.42(2H, m), 8.21(1H, brs), 8.30(1H, s), 9.13(1H, brs), 9.83(1H, brs), 9.92(1H, brs), 11.61(1H, brs)

EXAMPLE 54

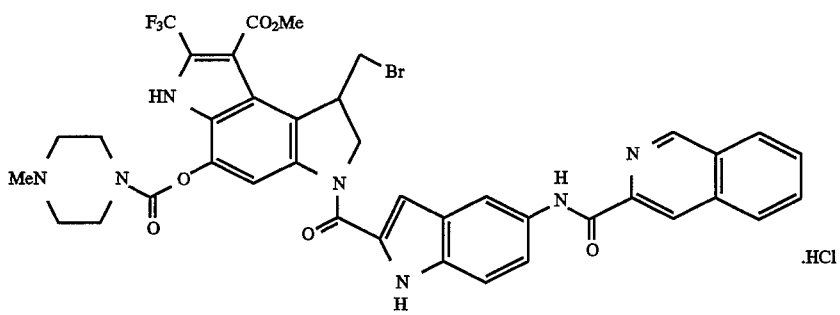

Methyl 1-bromomethyl-5-(4-methylpiperazin-1-ylcarbonyl)oxy-3-[5-[(isoquinolin-3-ylcarbonyl)amino]-1H-indol-2-yl carbonyl]-7-trifluoromethyl-1,2,3,6-tetrahydropyrrolo[3,2-e]indole-8-carboxylate hydrochloride salt was prepared by using 13.0 mg (.18 μmol) of methyl 1-bromomethyl-5-hydroxy-3-[5-[(isoquinolin-3-ylcarbonyl)amino]-1H-indol-2-ylcarbonyl]-7-trifluoromethyl-1,2,3,6-tetrahydropyrrolo[3,2-e]indole-8-carboxylate in the same manner as in Example 46 in a yield of 2.2 mg (13%).

NMR (DMSOd₆) δ: 2.86(3H, brs), 3.21~3.61(7H, m), 3.85(1H, m), 3.93(3H, s), 4.16(1H, m), 4.42~4.48(2H, m), 4.59(1H, d, J=11 Hz), 4.83(1H, t, J=9 Hz), 7. 22(1H, s), 7.52(1H, d, J=9 Hz), 7.76(1H, d, J=9 Hz), 7.86(1H, t, J=8 Hz), 7.93(1H, t, J=8 Hz), 8.21(1H, s), 8.26(1H, d, J=8 Hz), 8.32(1H, d, J=6 Hz), 8.41(1H, s), 8.74(1H, s), 9.50(1H, s), 10.71(1H, s), 10.84(1H, br), 11.65(1H, s), 13.17(1H, s)

EXAMPLE 55

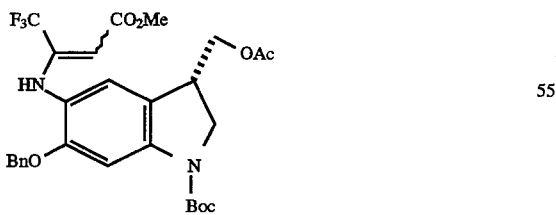

Methyl 3-((3S)-3-acetoxymethyl-6-benzyloxy-1-t-butoxycarbonyl-2,3-dihydro-1H-indol-5-yl)amino-3-trifluoromethylacrylate was prepared/from (3S)-3-acetoxymethyl-5-amino-6-benzyloxy-1-(t-butoxycarbonyl)-2,3-dihydroindole in the same manner as in Example 1.

[α]_D^{25}=+8.9° (c=0.53, chloroform)

EXAMPLE 56

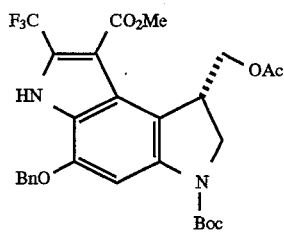

Methyl (1S)-1-acetoxymethyl-5-benzyloxy-3-t-butoxycarbonyl-7-trifluoromethyl-1,2,3,6-tetrahydropyrrolo[3,2-e]indole-8-carboxylate was prepared from methyl 3-((3S)-3-acetoxymethyl-6-benzyloxy-1-t-butoxycarbonyl-2,3-dihydro-1H-indol-5-yl)amino-3-trifluoromethylacrylate in the same manner as in Example 2.

[α]_D^{25}=−70° (c=0.20, chloroform)

EXAMPLE 57

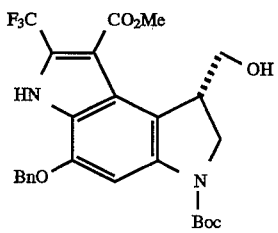

Methyl (1S)-5-benzyloxy-3-t-butoxycarbonyl-1-hydroxymethyl-7-trifluoromethyl-1,2,3,6-tetrahydropyrrolo[3,2-e]indole-8-carboxylate was prepared from methyl (1S)-1-acetoxymethyl-5-benzyloxy-3-t-butoxycarbonyl-7-trifluoromethyl-1,2,3,6-tetrahydropyrrolo[3,2-e]indole-8-carboxylate in the same manner as in Example 3.

[α]_D^{25}=−32° (c=0.45, chloroform)

EXAMPLE 58

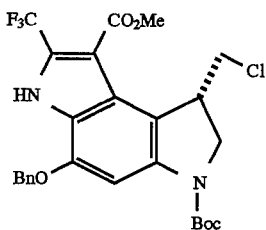

Methyl (1S)-5-benzyloxy-3-t-butoxycarbonyl-1-chloromethyl-7-trifluoromethyl-1,2,3,6-tetrahydropyrrolo[3,2-e]indole-8-carboxylate was prepared from methyl (1S)-5-benzyloxy-3-t-butoxycarbonyl-1-hydroxymethyl-7-trifluoromethyl-1,2,3,6-tetrahydropyrrolo[3,2-e]indole-8-carboxylate in the same manner as in Example 4.

$[\alpha]_D^{23} = -60°$ (c=0.40, chloroform)

EXAMPLE 59

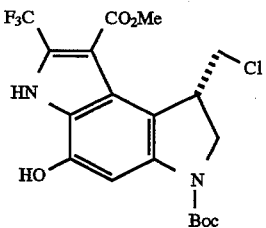

Methyl (1S)-3-t-butoxycarbonyl-1-chloromethyl-5-hydroxy-7-trifluoromethyl-1,2,3,6-tetrahydropyrrolo[3,2-e]indole-8-carboxylate was prepared from methyl (1S)-5benzyloxy-3-t-butoxycarbonyl-1-chloromethyl-7-trifluoromethyl-1,2,3,6-tetrahydropyrrolo[3,2-e]indole-8-carboxylate in the same manner as in Example 5.

$[\alpha]_D^{23} = -78°$ (c=0.32, chloroform)

EXAMPLE 60

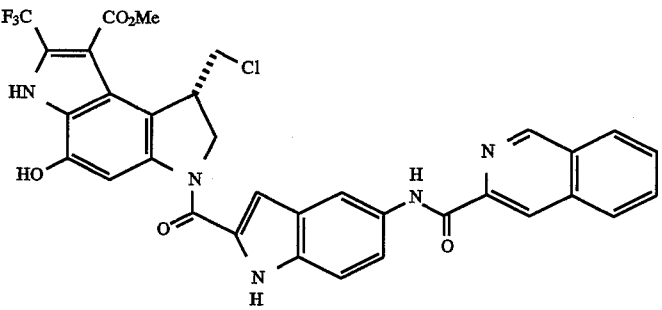

Methyl (1S)-1-chloromethyl-5-hydroxy-3-[5-[(isoquinolin-3-ylcarbonyl)amino]-1H-indol-2-ylcarbonyl]-7-trifluoromethyl-1,2,3,6-tetrahydropyrrolo[3,2-e]indole-8-carboxylate was prepared by using 3-(5-isoquinolin-3-ylcarbonyl)amino-1H-indole-2-carboxylic acid in the same manner as in Example 6.

NMR (DMSOd$_6$) δ: 3.52(1H, t, J=8 Hz), 3.87(1H, m), 3.89(3H, s), 4.30(1H, m), 4.56(1H, d, J=11 Hz), 4.72(1H, t, J=8 Hz), 7.18(1H, s), 7.50(1H, d, J=9 Hz), 7.73(1H, d, J=9 Hz), 7.84(1H, t, J=7 Hz), 7.91(1H, t, J=7 Hz), 7.96(1H, s), 8.25~8.31(2H, m), 8.39(1H, s), 8.73(1H, s), 9.48(1H, d, J=2 Hz), 10.56(1H, brs), 10.68(1H, brs), 11.72(1H, s), 13.05 (1H, brs)

$[\alpha]_D^{24} = +63°$ (c=0.24, tetrahydrofuran)

EXAMPLE 61

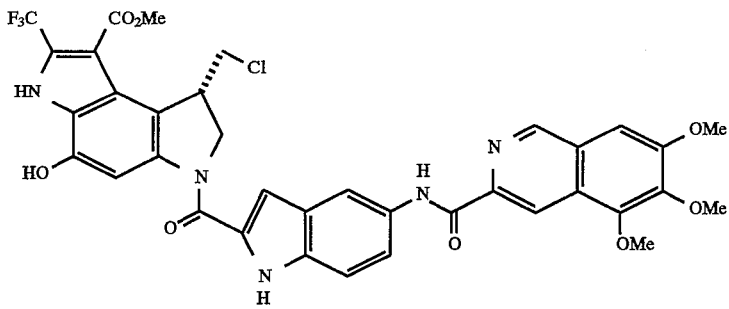

Methyl(1S)-1-chloromethyl-5-hydroxy-7-trifluoromethyl-3-[5-[(5,6,7-trimethoxyisoquinolin-3-ylcarbonyl)amino]-1H-indol-2-ylcarbonyl]-1,2,3,6-tetrahydropyrrolo[3,2-e]indole-8-carboxylate was prepared by using 5-(5,6,7-trimethoxyisoquinolin-3-ylcarbonyl)amino-1H-indole-2-carboxylic acid in the same manner as in Example 6.

$[\alpha]_D^{26}$=+63° (c=0.24, tetrahydrofuran)

EXAMPLE 62

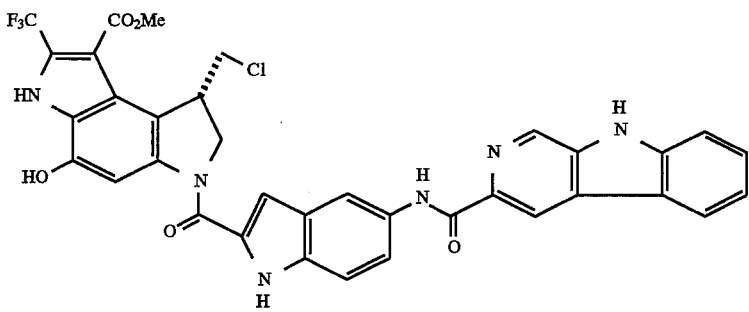

Methyl (1S)-1-chloromethyl-5-hydroxy-3-[5-[(9H-pyrido[3,4-b]indol-3-ylcarbonyl)amino]-1H-indol-2-ylcarbonyl]-7-trifluoromethyl-1,2,3,6-tetrahydropyrrolo[3,2-e]indole-8-carboxylate was prepared by using 5-(9H-pyrido[3,4-b]indol-3-ylcarbonyl)amino-1H-indole-2-carboxylic acid in the same manner as in Example 6.

$[\alpha]_D^{26}$=+67° (c=0.31, tetrahydrofuran)

Methyl (1S)-1-chloromethyl-5-hydroxy-3-[5-[(7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate was prepared by using 5-(7-methoxybenzofuran-2-ylcarbonyl)amino-1H-indole-2-carboxylic acid in the same manner as in Example 6.

$[\alpha]_D^{26}$=+53° (c=0.36, tetrahydrofuran)

EXAMPLE 63

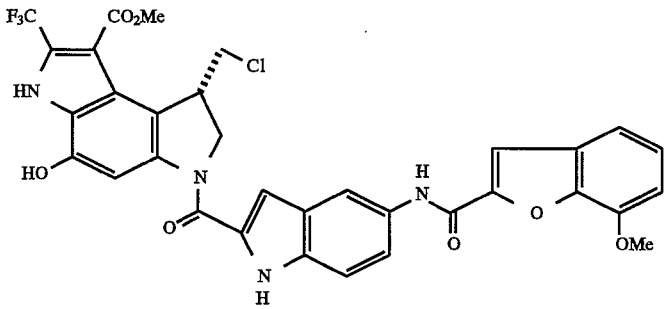

EXAMPLE 64

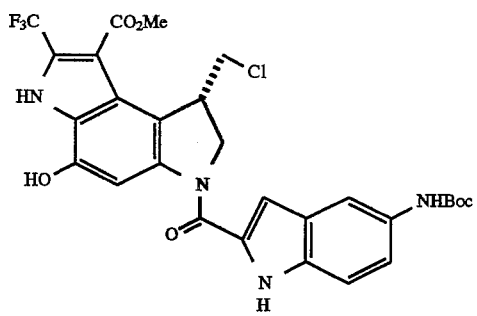

Methyl (1S)-3-[5-(t-butoxycarbonyl)amino-1H-indol-2-ylcarbonyl]-1-chloromethyl-5-hydroxy-7-trifluoromethyl-1,2,3,6-tetrahydropyrrolo[3,2-e]indole-8-carboxylate was prepared by using 13.8 mg (50 μmol) of 5-(t-butoxycarbonyl)-amino-1H-indole-2-carboxylic acid in the same manner as in Example 6 in a yield of 22.4 mg (74%).

NMR (CDCl$_3$) δ: 1.55(9H, s), 3.29(1H, t, J=10 Hz), 3.77(1H, d, J=10 Hz), 3.92(3H, s), 4.41(1H, m), 4.52(1H, t, J=10 Hz), 4.64(1H, d, J=11 Hz), 6.57(1H, s), 6.93(1H, s), 7.01(1H, brd, J=7 Hz), 7.21(1H, brd, J=8 Hz), 7.66(1H, brs), 8.21(1H, brs), 9. 60(2H, br), 10.13(1H, brs)

$[\alpha]_D^{24}$=+29° (c=0.20, tetrahydrofuran)

EXAMPLE 65

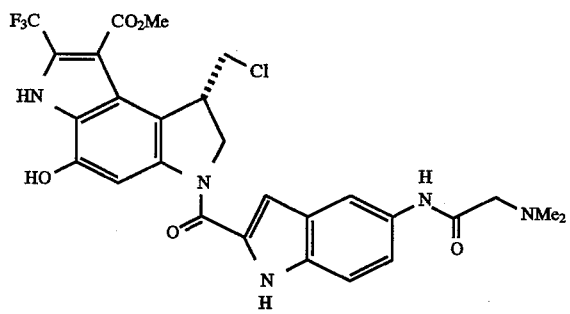

Methyl (1S)-1-chloromethyl-3-[5(dimethylaminomethylcarbonyl)amino-1H-indol-2-ylcarbonyl]-5-hydroxy-7-trifluoromethyl-1,2,3,6-tetrahydropyrrolo[3,2-e]indole-8-carboxylate was prepared from 12.1 mg (20 μmol) of methyl (1S)-3-[5-(t-butoxycarbonyl)amino-1H-indol-2-ylcarbonyl]-1-chloromethyl-5-hydroxy-7-trifluoromethyl-1,2,3,6-tetrahydropyrrolo[3,2-e]indole-8-carboxylate and 2.8 mg (20 μmol) of N, N-dimethylglycine hydrochloride in the same manner as in Example 6 in a yield of 7.8 mg (66%).

NMR (DMSOd$_6$) δ: 2.34 (6H, s), 3.12(2H, s), 3.49(1H, t, J=11 Hz), 3.84(1H, m), 3.88(3H, s), 4.28(1H, m), 4.53(1H, d, J=11 Hz), 4.68(1H, t, J=9 Hz), 7.10(1H, m), 7.41(2H, m), 7.93(1H, brs), 8.08(1H, s), 9.62(1H, s), 10.50(1H, br), 11.64(1H, s), 13.00(1H, br)

$[\alpha]_D^{24}$=+85° (c=0.20, tetrahydrofuran)

EXAMPLE 66

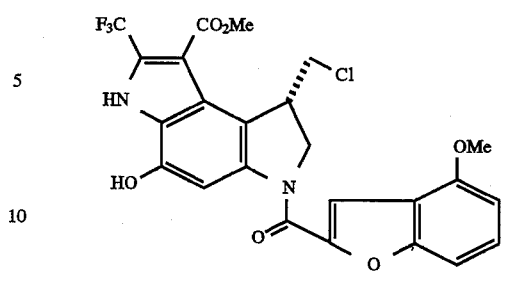

Methyl (1S)-1-chloromethyl-5-hydroxy-3-(4-methoxybenzofuran-2-yl carbonyl)-7-trifluoromethyl-1,2,3,6-tetrahydropyrrolo[3,2-e]indole-8-carboxylate was prepared by using 4.8 mg (25 μmol) of 4-methoxybenzofuran-2-carboxylic acid in the same manner as in Example 6 in a yield of 11.6 mg (89%).

NMR (DMSOd$_6$) δ: 3.52(1H, dd, J=9 Hz, J=10 Hz), 3.84(1H, dd, J=3 Hz, 11 Hz), 3.87(3H, s), 3.97(3H, s), 4.22~4.32(1H, m), 4.49(1H, d, J=11 Hz), 4.69(1H, t J=10 Hz), 6.89(1H, d, J=8 Hz), 7.31(1H, d, J=9 Hz), 7.45(1H, t, J=8 Hz), 7.62(1H, s), 7. 90(1H, brs), 10.65(1H, brs), 13.15 (1H, brs)

$[\alpha]_D^{26}$=−11° (c=0.20, tetrahydrofuran)

EXAMPLE 67

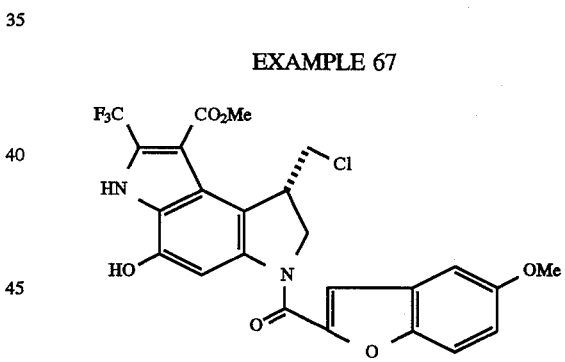

Methyl (1S)-1-chloromethyl-5-hydroxy-3-(5-methoxybenzofuran-2-ylcarbonyl)-7-trifluoromethyl-1,2,3,6-tetrahydropyrrolo[3,2-e]indole-8-carboxylate was prepared by using 4.8 mg (25 μmol) of 5-methoxybenzofuran-2-carboxylic acid in the same manner as in Example 6 in a yield of 7.1 mg (54%).

NMR (DMSOd$_6$) 8:3.53(1H, dd, J=8 Hz, J=10 Hz), 3.83(3H, s), 3.82~3. 90(1H, m), 3.87(3H, s), 4.24~4.32(1H, m), 4.52(1H, d, J=12 Hz), 4.65(1H, t, J=10 Hz), 7.09(1H, dd, J=3 Hz, J=9 Hz), 7.29(1H, d, J=3 Hz), 7.61(1H, s), 7.63(1H, d, J=9 Hz), 7.91(1H, brs), 10.60(1H, brs), 13.11(1H, brs)

$[\alpha]_D^{26}$=+1.4° (c=0.20, tetrahydrofuran)

EXAMPLE 68

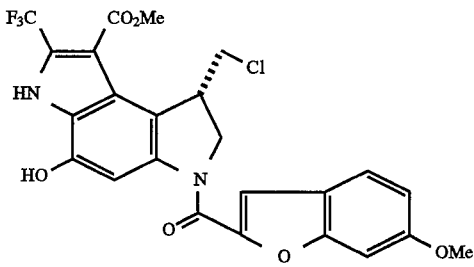

Methyl (1S)-1-chloromethyl-5-hydroxy-3-(6-methoxybenzofuran-2-ylcarbonyl)-7-trifluoromethyl-1,2,3,6-tetrahydropyrrolo[3,2-e]indole-8-carboxylate was prepared by using 4.8 mg (25 μmol) of 6-methoxybenzofuran-2-carboxylic acid in the same manner as in Example 6 in a yield of 9.8 mg (75%).

NMR (DMSOd$_6$) δ: 3.52(1H, dd, J=9 Hz, J=11 Hz), 3.87(3H, s), 3.88(3H, s), 4.24~4.32(1H, m), 4.53(1H, d, J=11 Hz), 4.65(1H, dd, J=9 Hz, J=11 Hz), 7.00(1H, dd, J=2 Hz, J=9 Hz), 7.32(1H, d, J=2 Hz), 7.63(1H, s), 7.68(1H, d, J=9 Hz), 7.90(1H, brs), 10.59(1H, brs), 13.09(1H, brs)

$[\alpha]_D^{26}$=+16° (c=0.20, tetrahydrofuran)

EXAMPLE 69

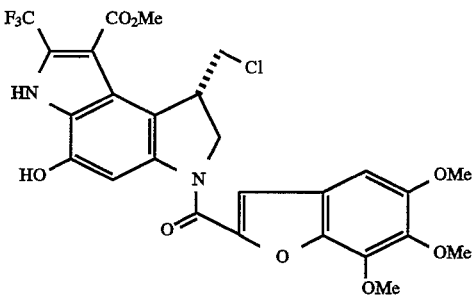

Methyl (1S)-1-chloromethyl-5-hydroxy-7-trifluoromethyl-3-(5,6,7-trimethoxybenzofuran-2-ylcarbonyl)-1,2,3,6-tetrahydropyrrolo[3,2-e]indole-8-carboxylate was prepared by using 6.3 mg (25 μmol) of 5,6,7-trimethoxybenzofuran-2-carboxylic acid in the same manner as in Example 6 in a yield of 10.5 mg (72%).

NMR (CDCl$_3$) δ: 3.36(1H, t, J=11 Hz), 3.85~3.95(1H, m), 3.91(3H, s), 3.95(3H, s), 3.97(3H, s), 4.28(3H, s), 4.46~4.51 (1H, m), 4.65(1h, dd 11 Hz), 4.90(1H, t, J=11 Hz), 6.83(1H, s), 7.68(1H, s), 8.54(1H, s), 9.72(1H, brs), 11.17(1H, brs)

$[\alpha]_D^{23}$=+18° (c=0.20, tetrahydrofuran)

EXAMPLE 70

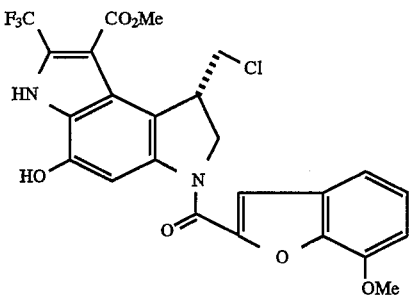

Methyl (1S)-1-chloromethyl-5-hydroxy-3-(7-methoxybenzofuran-2-ylcarbonyl)-7-trifluoromethyl-1,2,3,6-tetrahydropyrrolo[3,2-e]indole-8-carboxylate was prepared by using 4.4 mg (23 μmol) of 7-methoxybenzofuran-2-carboxylic acid in the same manner as in Example 6 in a yield of 9.3 mg (77%).

NMR (DMSOd$_6$) δ: 3.52(1H, dd, J=8 Hz, J=10 Hz), 3.84(1H, dd, J=3 Hz, J=10 Hz), 3.88(3H, s), 4.00(3H, s), 4.29(1H, m), 4.52(1H, d, J=10 Hz), 4.64(1H, dd, J=8 Hz, J=10 Hz), 7.09(1H, d, J=8 Hz), 7.28(1H, t, J=8 Hz), 7.36(1H, dd, J=1 Hz, J=8 Hz), 7.66(1H, s), 7.92(1H, brs), 10.59(1H, brs), 13.09(1H, brs)

$[\alpha]_D^{24}$=+33° (c=0.20, tetrahydrofuran)

EXAMPLE 71

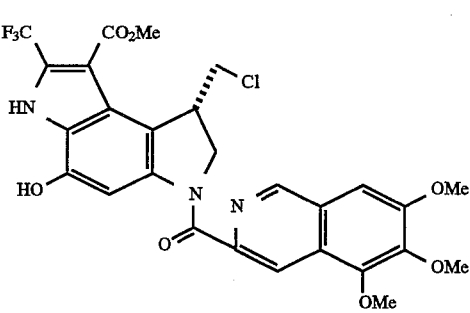

Methyl (1S)-1-chloromethyl-5-hydroxy-7-trifluoromethyl-3-(5,6,7-trimethoxyisoquinolin-3-ylcarbonyl)-1,2,3,6-tetrahydropyrrolo[3,2-e]indole-8-carboxylate was prepared by using 6.0 mg (23 μmol) of 5,6,7-trimethoxyisoquinoline-3-carboxylic acid in the same manner as in Example 6 in a yield of 11.1 mg (81%).

NMR (DMSOd$_6$) δ: 3.44(1H, t, J=9 Hz), 3.79(1H, m), 3.85(3H, s), 3.95(3H, s), 4.01(3H, s), 4.04(3H, s), 4.16(1H, m), 4.21(1H, d, J=11 Hz), 4.48(1H, t, J=9 Hz), 7.50(1H, s), 7.96(1H, brs), 8.26(1H, s), 9.21(1H, s), 10.60(1H, br), 12.90(1H, br)

$[\alpha]_D^{24}$=-46° (c=0.20, tetrahydrofuran)

EXAMPLE 72

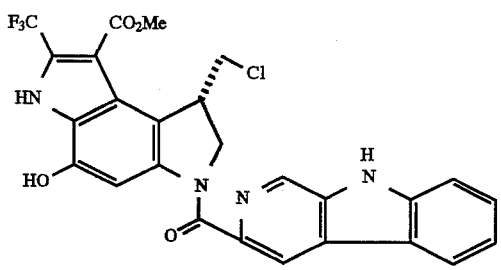

Methyl (1S)-1-chloromethyl-5-hydroxy-7-trifluoromethyl-3-(9H-pyrido[3,4-b]indol-3-ylcarbonyl)-1,2,3,6-tetrahydropyrrolo[3,2-e]indole-8-carboxylate was prepared by using 4.9 mg (23 μmol) of 9H-pyrido[3,4-b]indole-3-carboxylic-acid in the same manner as in Example 6 in a yield of 9.9 mg (79%).

NMR (DMSOd$_6$) δ: 3.42(1H, t, J=9 Hz), 3.81(1H, m), 3.85(3H, s), 4.16(1H, m), 4.30(1H, d, J=11 Hz), 4.55(1H, m), 7.31(1H, t, J=8 Hz), 7.60(1H, t, J=8 Hz), 7.67(1H, d, J=8 Hz), 7.98(1H, brs), 8.37(1H, d, J=8 Hz), 8.67(1H, brs), 8.95(1H, s), 10.58(1H, br), 11.95(1H, s), 13.00(1H, br), $[\alpha]_D^{24}$=−52° (c=0.20, tetrahydrofuran)

EXAMPLE 73

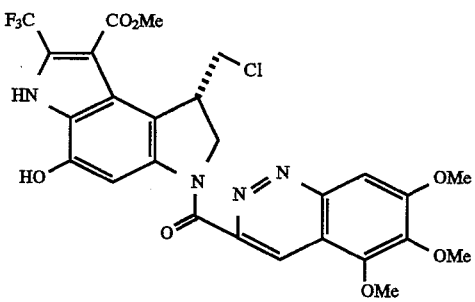

Methyl (1S)-1-chloromethyl-5-hydroxy-7-trifluoromethyl-3-(5,6,7-trimethoxycinnolin-3-ylcarbonyl)-1,2,3,6-tetrahydropyrrolo[3,2-e]indole-8-carboxylate was prepared by using 6.1 mg (23 μmol) of 5,6,7-trimethoxycinnoline-3-carboxylic acid in the same manner as in Example 6 in a yield of 9.9 mg (72%).

NMR (DMSOd6) δ: 3.50(1H, t, J=10 Hz), 3.80(1H, dd, J=2 Hz, J=10 Hz), 3.86(3H, s), 4.00(3H, s), 4.08(3H, s), 4.11(3H, s), 4.18~4.24(2H, m), 4.54(1H, dd, J=9 Hz, J=11 Hz), 7.75(1H, s), 8.04(1H, s), 8.45(1 H, s), 10.63(1H, s), 13.10(1H, s)

$[\alpha]_D^{24}$=−19° (c=0.20, tetrahydrofuran)

EXAMPLE 74

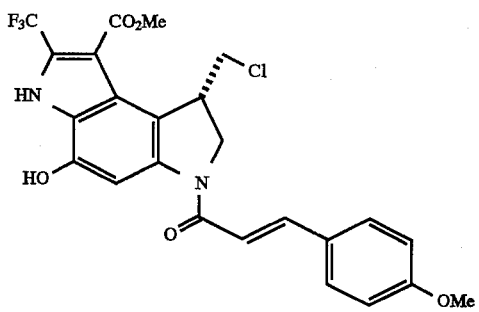

Methyl (1S)-1-chloromethyl-5-hydroxy-3-[2-(4-methoxyphenyl)ethylene-1-ylcarbonyl]-7-trifluoromethyl-1,2,3,6-tetrahydropyrrolo[3,2-e]indole-8-carboxylate was prepared by using 4.1 mg (23 μmol) of 4-methoxycinnamic acid in the same manner as in Example 6 in a yield of 6.1 mg (52%).

NMR (DMSOd$_6$) δ: 3.46(1H, dd, J=9 Hz, J=10 Hz), 3.79~3.82(1H, m), 3.82(3H, s), 3.88(3H, s), 4.26(1H, br), 4.37(1H, t, J=10 Hz), 4.43(1H, d, J=10 Hz), 6.99(2H, d, J=9 Hz), 7.05(1H, d, J=15 Hz), 7.62(1H, d, J=15 Hz), 7.74(2H, d, J=9 Hz), 8.10(1H, brs), 10.49(1H, s), 13.00(1H, s)

$[\alpha]_D^{24}$=−59° (c=0.20, tetrahydrofuran)

EXAMPLE 75

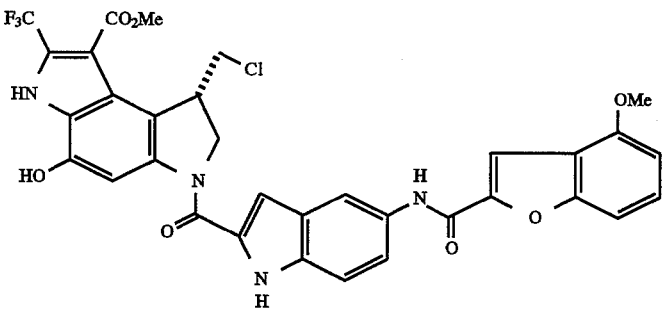

Methyl (1S)-1-chloromethyl-5-hydroxy-3-[5-(4-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate was prepared by using 8.8 mg (25 μmol) of 5-(4-methoxybenzofuran-2-ylcarbonyl)amino-1H-indole-2-carboxylic acid in the same manner as in Example 6 in a yield of 12.5 mg (73%).

NMR (DMSOd₆) δ: 3.53(1H, dd, J=9 Hz, J=11 Hz), 3.82~3.92(1H, m), 3. 88(3H, s), 3.97(3H, s), 4.25~4.35(1H, m), 4.54(1H, d, J=11 Hz), 4.72(1H, t, J=11 Hz), 6.89(1H, d, J=8 Hz),7.18(1H, s),7.31(1H, d, J=9 Hz),7.44(1H, t, J=8 Hz),7.49(1H, d J=9 Hz), 7.58~7.64(1H, m), 7.79(1H, s), 7.95(1H, brs), 8.21(1H, s), 10.39(1h,s,), 10.59(1H, brs), 11.74(1H, s), 13.10(1H, brs)

$[\alpha]_D^{25}=+57°$ (c=0.20, tetrahydrofuran)

Methyl (1S)-1-chloromethyl-5-hydroxy-3-[5-(6-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate was prepared by using 8.8 mg (25 μmol) of 5-(6-methoxybenzofuran-2-ylcarbonyl)amino-1H-indole-2-carboxylic acid in the same manner as in Example 6 in a yield of 13.7 mg (80%).

EXAMPLE 76

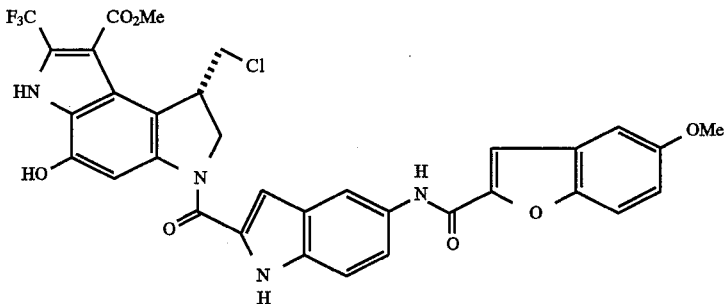

Methyl (1S)-1-chloromethyl-5-hydroxy-3-[5-(5-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate was prepared by using 8.8 mg (25 μmol) of 5-(5-methoxybenzofuran-2-ylcarbonyl)amino-1H-indole-2-carboxylic acid in the same manner as in Example 6 in a yield of 10.7 mg (63%).

NMR (DMSOd₆) δ: 3.46(1H, dd, J=8 Hz, J=11 Hz), 3.77(3H, s), 3.78~3. 84(1H, m), 3.81(3H, s), 4.18~4.26(1H, m), 4.47(1H, d, J=11 Hz), 4.65(1H, t, J=11 Hz), 7.02(1H, dd, J=2 Hz, J=9 Hz), 7.11(1H, s), 7.25(1H, d, J=3 Hz), 7.42(1H, d, J=9 Hz), 7.53~7.57(2H, m), 7.62(1H, s), 7.89(1H, brs), 8.14(1H, s), 10.38(1H, s), 10.53(1H, s), 11.67(1H, s), 13.04 (1H, s)

$[\alpha]_D^{25}=+44°$ (c=0.20, tetrahydrofuran)

NMR (DMSOd₆) δ: 3.53(1H, dd, J=10 Hz, J=11Hz), 3.82~3.92(1H, m), 3.87(3H, s), 3.89(3H, s), 4.25~4.28(1H, m), 4.54(1H, d, J=10 Hz), 4.70~4.75(1H, m), 7.00(1H, dd, J=2 Hz, J=9 Hz), 7.18(1H, s), 7.28(1H, d, J=2 Hz), 7.49(1H, d, J=9 Hz), 7.60(1H, dd, J=2 Hz, J=9 Hz), 7.66~7.74(2H, m), 7.95(1H, brs), 8.20(1 H, s), 10.34(1H, s), 10.59(1H, s), 11.73(1H, s), 13.11(1H, s)

$[\alpha]_D^{26}=+42°$ (c=0.20, tetrahydrofuran)

EXAMPLE 77

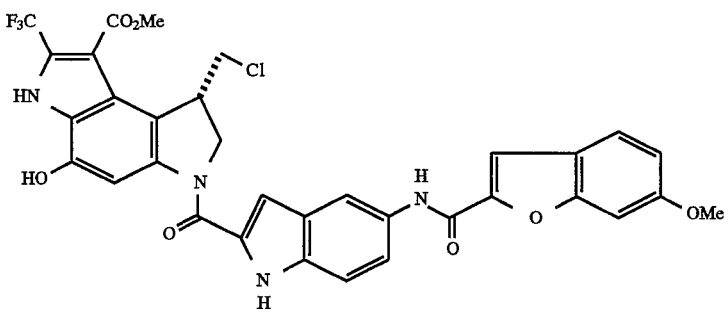

EXAMPLE 78

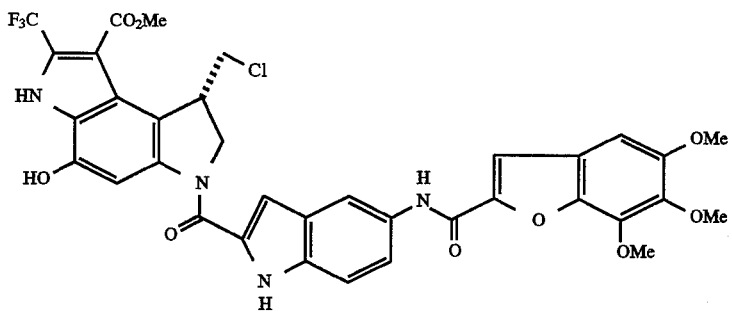

Methyl (1S)-1-chloromethyl-5-hydroxy.-7trifluoromethyl-3-[5-(5,6,7-trimethoxybenzofuran-2-ylcarbonyl)amino-1H-indol-2-ylcarbonyl]-1,2,3,6-tetrahydropyrrolo[3,2-e]indole-8-carboxylate was prepared by using 8.2 mg (20 μmol) of 5-(5,6,7-trimethoxybenzofuran-2-ylcarbonyl)amino-1H-indole-2-carboxylic acid in the same manner as in Example 6 in a yield of 8.7 mg (59%).

NMR (DMSOd$_6$) δ: 3.53(1H, dd, J=9 Hz, J=11 Hz), 3.81(3H, s), 3.82~3. 92(1H, m), 3.86(3H, s), 3.88(3H, s), 4.17(3H, s), 4.25~4.35(1H, m), 4.54(1H, d, J=11 Hz), 4.72 (1H, t, J=11 Hz), 7.08(1H, s),7.18(1H, s),7.49(1H, d, J=9Hz) ,7.56(1H, J=2 Hz, J=9 Hz), 7.69(1H, s), 7.95(1H, brs), 8.17(1H, s), 10.32(1H, s), 10.60(1H, brs), 11.75(1H, s), 13. 10(1H, brs)

$[α]_D^{25}$=+55° (c=0.20, tetrahydrofuran)

EXAMPLE 79

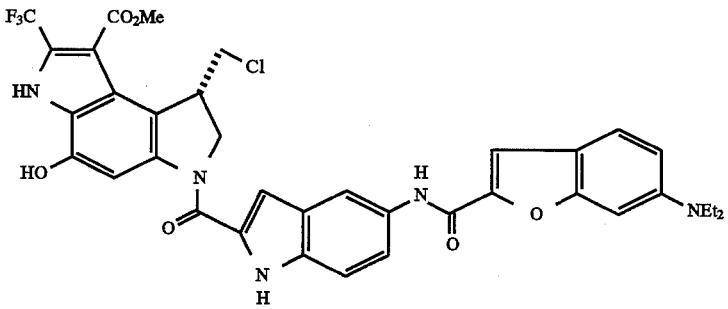

Methyl (1S)-1-chloromethyl-3-[5-(6-diethylaminobenzofuran-2-ylcarbonyl)amino-1H-indol-2-ylcarbonyl]-5-hydroxy-7-trifluoromethyl-1,2,3,6tetrahydropyrrolo[3,2-e]indole-8-carboxylate was prepared by using 9.8 mg (25 μmol) of 5-(6-diethylaminobenzofuran-2-ylcarbonyl)amino-1H-indole-2-carboxylic acid in the same manner as in Example 6 in a yield of 15.1 mg (83%).

NMR (DMSOd$_6$) δ: 1.15(6H, t, J=7 Hz, 3.43(4H, q, J=7 Hz), 3.50~3.55(1H, m),3.85~3.95(1H, m),3.88(3H, s),4.25~4.35(1H, m),4.53(1H, d, J=11 Hz),4. 70~4.78(1H, m), 6.79(1H, s), 6.81(1H, s), 7.17(1H, s), 7.47(1H, d, J=9 Hz), 7.52~7.61(3H, m), 7.95(1H, brs), 8.19(1H, s), 10.14 (1H, s), 10.59(1H, brs), 11.70(1H, s), 13. 11(1H, brs)

$[α]_D^{25}$=+58° (c=0.20, tetrahydrofuran)

EXAMPLE 80

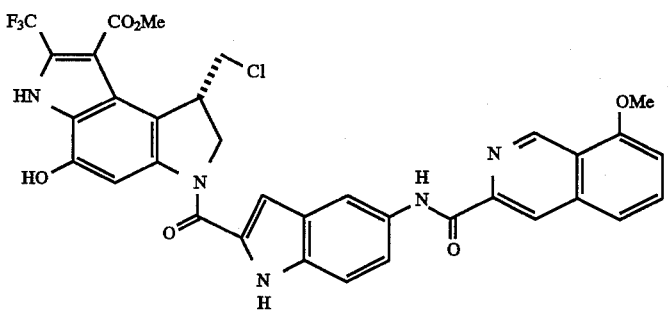

Methyl (1S)-1-chloromethyl-5-hydroxy-3-[5-(8-methoxyisoquinolin-3-ylcarbonyl)amino-1H-indol-2-ylcarbonyl]-7-trifluoromethyl-1,2,3,6-tetrahydropyrrolo[3,2-e]indole-8-carboxylate was prepared by using 4.0 mg (11 µmol) of 5-(8-methoxyisoquinolin-3-ylcarbonyl)amino-1H-indole-2-carboxylic acid in the same manner as in Example 6 in a yield of 4.0 mg (52%).

NMR (DMSOd$_6$) δ: 3.52(1H, t, J=10 Hz), 3.82~3.95(1H, m), 3.88(3H, s), 4.08(3H, s), 4.25~4.35(1H, m), 4.54(1H, d, J=11 Hz), 4.71(1H, t, 10 Hz), 7.18(1H, s), 7.28(1H, d, J=8 Hz), 7.50(1H, d, J=9 Hz), 7.70~7.75(1H, m), 7.78(1H, d, J=8 Hz), 7. 83(1H, t, J=8 Hz), 7.95(1H, brs), 8.38(1H, brs), 8.66(1H, s), 9.60(1H, s), 10.60(1 H, brs), 10.70(1H, s), 11.72(1H, s), 13.10(1H, brs)

$[α]_D^{25}$=+53° (c=0.20, tetrahydrofuran)

Methyl (1 S)-1-chloromethyl-5-hydroxy-3-[5-(6-methoxyisoquinolin-3-ylcarbonyl)amino-1H-indol-2-ylcarbonyl]-7-trifluoromethyl-1,2,3,6-tetrahydropyrrolo[3,2-e]indole-8-carboxylate was prepared by using 9.0 mg (25 µmol) of 5-(6-methoxyisoquinolin-3-ylcarbonyl)amino-1-H-indole-2-carboxylic acid in the same manner as in Example 6 in a yield of 13.6 mg (78%).

NMR (DMSOd$_6$) δ: 3.53(1H, dd, J=9 Hz, J=11 Hz), 3.84~3.94(1H, m), 3. 89(3H, s), 3.97(3H, s), 4.25~4.35(1H, m), 4.54(1H, d, J=11 Hz), 4.73(1H, t, J=11 Hz), 7.18(1H, s), 7.45(1H, dd, J=3 Hz, J=9Hz), 7.49(1H, d, J=9 Hz), 7.67(1H, d, J=2 Hz), 7.70~7.76(1H, m), 7.95(1H, brs), 8.20(1H, d, J=9 Hz), 8.38(1 H, s), 8.61(1H, s), 9.32(1H, s), 10.59(1H, s), 10.66(1H, s), 11.72(1H, s), 13.11(1H, s)

$[α]_D^{25}$=+60° (c=0.20, tetrahydrofuran)

EXAMPLE 81

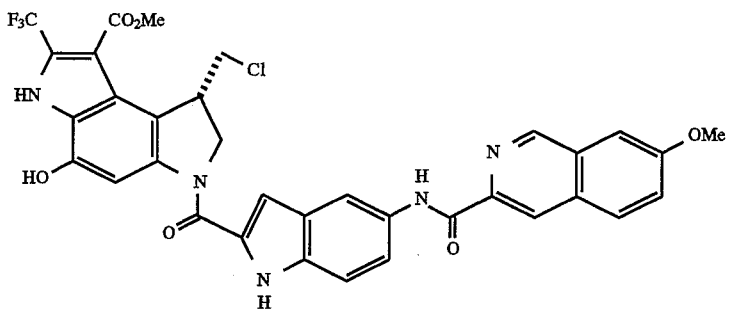

Methyl (1S)-1-chloromethyl-5-hydroxy-3-[5-(7-methoxyisoquinolin- 3-ylcarbonyl)amino-1H-indol-2-ylcarbonyl]-7-trifluoromethyl-1,2,3,6-tetrahydropyrrolo[3,2e]indole-8-carboxylate was prepared by using 7.3 mg (20 µmol) of 5-(7-methoxyisoquinolin-3-ylcarbonyl)amino-1H-indole-2-carboxylic acid in the same manner as in Example 6 in a yield of 9.4 mg(68%).

NMR (DMSOd$_6$) δ: 3.52(1H, dd, J=8 Hz, J=10 Hz), 3.83~3.93(1H, m), 3. 88(3H, s), 3.98(3H, s), 4.25~4.35(1H, m), 4.54(1H, d, J=10 Hz), 4.73(1H, t, J=10 Hz), 7.18(1H, s), 7.49(1H, d, J=9 Hz), 7.55(1H, dd, J=3 Hz, J=9 Hz), 7.68~7.76(2H, m), 7.95(1H, brs), 8.18(1H, d, J=9 Hz), 8.37(1H, d, J=2 Hz), 8.65(1H, s), 9.37(1H, s), 10.59(1H, s), 10.62(1H, s), 11.71(1H, s), 13.10(1H, brs)

$[α]_D^{25}$=+71° (c=0.20, tetrahydrofuran)

EXAMPLE 82

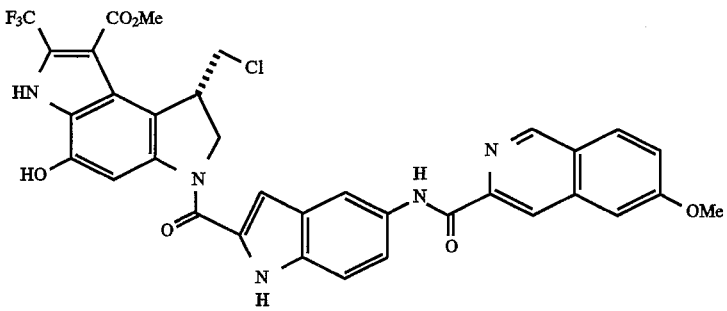

EXAMPLE 83

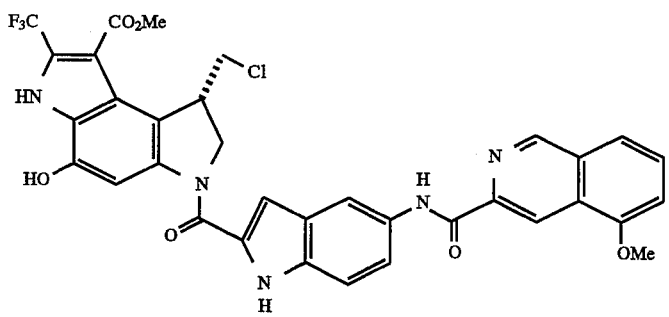

Methyl (1S)-1-chloromethyl-5-hydroxy-3-[5-(5-methoxyisoquinolin-3-ylcarbonyl)amino-1H-indol-2-ylcarbonyl]-7-trifluoromethyl-1,2,3,6-tetrahydropyrrolo[3,2-e]indole-8-carboxylate was prepared by using 9.0 mg(25 µmol) of 5-(5-methoxyisoquinolin-3-ylcarbonyl)amino-1H-indole-2-carboxylic acid in the same manner as in Example 6 in a yield of 11.1 mg (64%).

NMR (DMSOd$_6$) δ: 3.53(1H, t, J=11 Hz), 3.84~3.95(1H, m), 3.88(3H, s), 4.08(3H, s), 4.25~4.35(1H, m), 4.54(1H, d, J=11 Hz), 4.73(1H, t, J=11 Hz), 7.19(1H, s), 7.37(1H, d, J=8 Hz), 7.50(1H, d, J=9 Hz), 7.73(1 H, dd, J=2 Hz, J=9 Hz), 7.78(1H, t, J=8 Hz), 7.85(1H, d, J=8 Hz), 7.95(1H, brs), 8.38(1H, d, J=2 Hz), 8.83(1H, s), 9.44(1H, s), 10.60(1H, brs), 10.68(1H, s), 11.72(1H, s), 13.10(1H, brs)

$[\alpha]_D^{25}$=+66° (c=0.20, tetrahydrofuran)

EXAMPLE 84

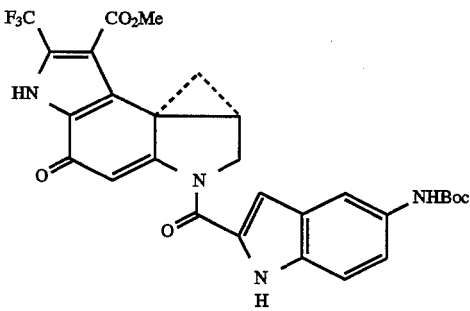

Methyl (7bR, 8aS)-2-[5-(t-butoxycarbonyl)amino-1H-indole-2-ylcarbonyl]-6-trifluoromethyl-1,2,8,8a-tetrahydrocyclopropa[c]pyrrolo[3,2-e]indole-4 (5H)-one-7-carboxylate was prepared by using 5.5 mg (9.1 µmol) of methyl (1S)-3-[5-(t-butoxycarbonyl)amino-1H-indol-2-ylcarbonyl]-1-chloromethyl-5-hydroxy-7-trifluoromethyl-1,2,3,6-tetrahydropyrrolo[3,2-e]indole-8-carboxylate in the same manner as in Example 20 in a yield of 4.9 mg (95%).

NMR (CDCl$_3$) δ: 1.40(1H, t, J=4 Hz), 1.54(9H, s), 2.34(1H, dd, J=4 Hz, J=8 Hz), 3.66(1H, m), 3.87(3H, s), 4.48(2H, m), 6.85(1H, brs), 6.96(1H, d, J=1 Hz), 7.18(1H, s), 7.22(1H, dd, J=2 Hz, J=9 Hz), 7.38(1H, d, J=9 Hz), 7.82(1H, brs), 9.98(1H, s), 11.83(1H, br)

$[\alpha]_D^{25}$=+120° (c=0.20, tetrahydrofuran)

EXAMPLE 85

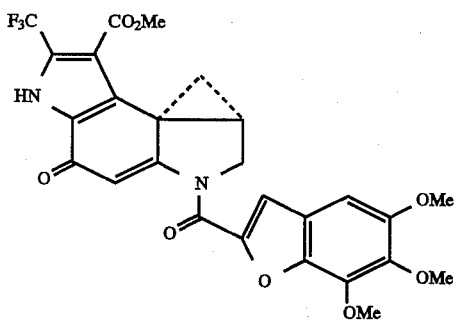

Methyl (7bR, 8aS)-6-trifluoromethyl-2-(5,6,7-trimethoxybenzofuran-2-ylcarbonyl)-1,2,8,8a-tetrahydrocyclopropa[c]pyrrolo[3,2-e]indol-4 (5H)-one-7-carboxylate was prepared by using 20.1 mg (35 µmol) of methyl (1S)-1-chloromethyl-5-hydroxy-7-trifluoromethyl-3 (5,6,7-trimethoxybenzofuran-2-ylcarbonyl)-1,2,3,6-tetrahydropyrrolo[3,2-e]indole-8-carboxylate in the same manner as in Example 20 in a yield of 14.1 mg (74%).

NMR (CDCl$_3$) δ: 1.48(1H, t, J=4 Hz), 2.42(1H, dd, J=4 Hz, J=8 Hz), 3.88(3H, s), 3.92(3H, s), 3.94(3H, s), 4.14(3H, s), 4.44~4.53(2H, m), 6.76(1H, brs), 6. 81(1H, s), 7.55(1H, s)

$[\alpha]_D^{27}$=+221° (c=1.1, chloroform)

EXAMPLE 86

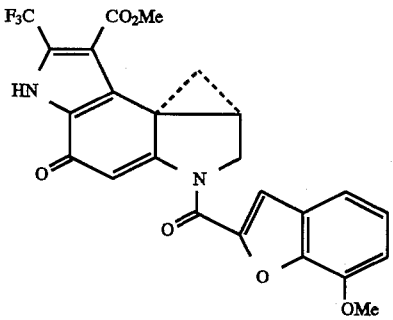

Methyl (7bR, 8aS)-2-(7-methoxybenzofuran-2-ylcarbonyl)-6-trifluoromethyl-1,2,8,8a-tetrahydrocyclopropa[c]pyrrolo[3,2-e]indol-4 (5H)-one-7-carboxylate was prepared by using 5.7 mg (11 µmol) of methyl (1S)-1-chloromethyl-5-hydroxy-3-(7-methoxybenzofuran-2-ylcarbonyl)-7-trifluoromethyl-1,2,3, 6-tetrahydropyrrolo[3,2-e]indole-8-carboxylate in the same manner as in Example 20 in a yield of 5.3 mg(98%).

NMR (CDCl$_3$) δ: 1.46(1H, t, J=4 Hz), 2.39(1H, dd, J=4 Hz, J=8 Hz), 3.68(1H, m), 3.87(3H, s), 4.00(3H, s), 4.54~4.62(2H, m), 6.94(1H, dd, J=1 Hz, J=7 Hz), 7.00(1H, brs), 7.24(1H, d, J=8 Hz), 7.28(1H, dd, J=1 Hz, J=8 Hz), 7.61(1H, s), 10.55(1H, br)

[α]$_D^{24}$=+201° (c=0.53, chloroform)

EXAMPLE 87

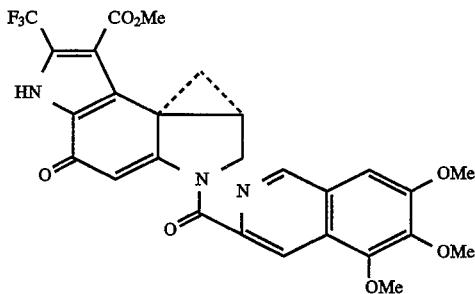

Methyl (7bR, 8aS)-6-trifluoromethyl-2-(5,6,7-trimethoxyisoquinolin-3-ylcarbonyl)-1,2,8,8a-tetrahydrocyclopropa[c]pyrrolo[3,2-e]indol-4 (5H)-one-7-carboxylate was prepared by using 5.8 mg (9.7 μmol) of methyl (1S)-1-chloromethyl-5-hydroxy-7-trifluoromethyl-3-(5,6,7-trimethoxyisoquinolin-3-ylcarbonyl)-1,2,3,6-tetrahydropyrrolo[3,2-e]indole-8-carboxylate in the same manner as in Example 20 in a yield of 5.0 mg (93%).

NMR (CDCl$_3$) δ: 1.63(1H, t, J=4 Hz), 2.42(1H, dd, J=4 Hz, J=8 Hz), 3.58(1H, m), 3.87(3H, s), 4.03(3H, s), 4.05(3H, s), 4.09(3H, s), 4.30(1H, d, J=12 Hz), 4.45(1H, dd, J=5 Hz, J=12 Hz), 6.25(1H, brs), 7.08(1H, s), 8.44(1H, s), 8.98(1H, s), 10.42(1H, br)

]α]$_D^{25}$=+73° (c=0.50, chloroform)

EXAMPLE 88

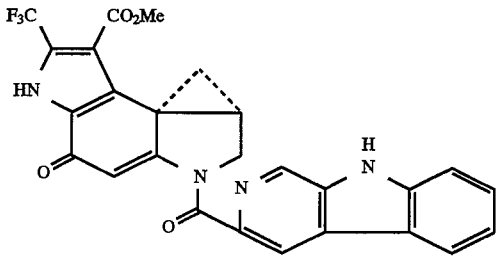

Methyl (7bR, 8aS)-2-(9H-pyrido[3,4-b]indol-3-ylcarbonyl)-6-trifluoromethyl-1,2,8,8a-tetrahydrocyclopropa[c]pyrrolo[3,2-e]indol-4 (5H)-one-7-carboxylate was prepared by using 6.7 mg (12 μmol) of methyl (1S)-1-chloromethyl-5-hydroxy-3-(9H-pyrido[3,4-b]indol-3-ylcarbonyl)-7-trifluoromethyl-1,2,3,6-tetrahydropyrrolo[3,2-e]indole-8-carboxylate in the same manner as in Example 20 in a yield of 5.4 mg (88%).

NMR (CDCl$_3$) δ: 1.56(1H, brs), 2.27(1H, brd, J=4 Hz), 3.55(1H, m), 3.83(3H, s), 4.21(1H, d, J=10 Hz), 4.40(1H, dd, J=4 Hz, J=11 Hz), 6.06(1H, brs), 7.33(1H, t, J=8 Hz), 7.50(1H, d, J=8 Hz), 7.58(1H, t, J=8 Hz), 8.06(1H, d, J=8 Hz), 8.46(1H, s), 8.84(1H, brs), 9.83(1H, br), 10.62(1H, br)

[α]$_D^{24}$=+81° (c=0.54, chloroform)

EXAMPLE 89

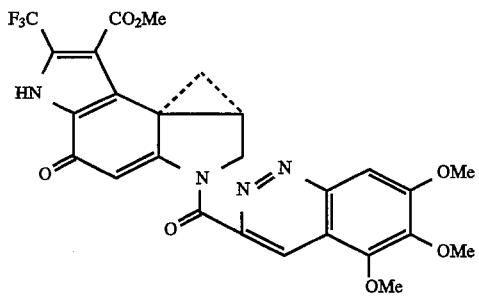

Methyl (7bR, 8aS)-6-trifluoromethyl-2-(5,6,7-trimethoxycinnolin-3-ylcarbonyl)-1,2,8,8a-tetrahydrocyclopropa[c]pyrrolo[3,2-e]indol-4 (5H)-one-7-carboxylate was prepared by using 5.7 mg (9.6 μmol) of methyl (1S)-1-chloromethyl-5-hydroxy-7-trifluoromethyl-3-(5,6,7-trimethoxycinnolin-3-ylcarbonyl)-1,2,3,6-tetrahydropyrrolo[3,2-e]indole-8-carboxylate in the same manner as in Example 20 in a yield of 4.6 mg (85%).

NMR (CDCl$_3$) δ: 1.66(1H, brs), 2.43(1H, dd, J=4 Hz, J=8 Hz), 3.63(1H, m), 3.87(3H, s), 4.07(3H, s), 4.13(3H×2, s), 4.45(1H, d, J=11 Hz), 4.60(1H, dd, J=5 Hz, J=11 Hz), 6.56(1H, br), 7.62(1H, s), 8.59(1H, s), 10.40(1H, br)

[α]$_D^{24}$=+141° (c=0.46, chloroform)

EXAMPLE 90

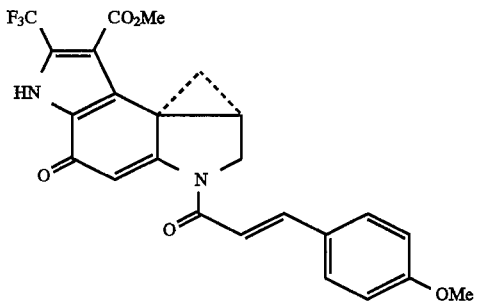

Methyl (7bR, 8aS)-2-[2-(4-methoxyphenyl)ethylene-1-ylcarbonyl)-6-trifluoromethyl-1,2,8,8a-tetrahydrocyclopropa[c]pyrrolo[3,2-e]indol-4 (5H)-one-7-carboxylate was prepared by using 3.8 mg (7.4 μmol) of methyl (1S)-1-chloromethyl-5-hydroxy-3-[2-(4-methoxyphenyl)ethylene-1-ylcarbonyl)-7-trifluoromethyl-1,2,3,6-tetrahydropyrrolo[3,2-e]indole-8-carboxylate in the same manner as in Example 20 in a yield of 3.5 mg (99%).

NMR (CDCl$_3$) δ: 1.37(1H, dd, J=4 Hz, J=5 Hz), 2.39 (1H, dd, J=4 Hz, J=8 Hz), 3.59(1H, m), 3.86(3H, s), 3.87(3H, s), 4.18(1H, dd, J=5 Hz, J=11 Hz), 4.25(1H, d, J=11 Hz), 6.72(1H, d, J=16 Hz), 6.78(1H, br), 6.93(2H, d, J=9 Hz), 7.53(2H, d, J=9 Hz), 7.80(1H, d, J=15 Hz), 10.41(1H, br)

[α]$_D^{24}$=+129° (c=0.35, chloroform)

EXAMPLE 91

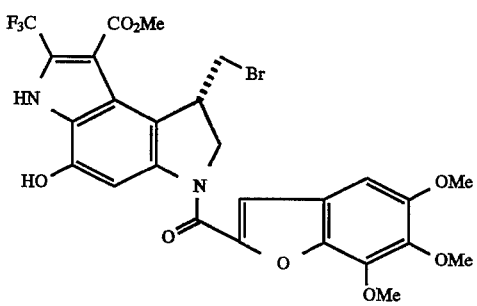

Methyl (1S)-1-bromomethyl-5-hydroxy-7-trifluoromethyl-3-(5,6,7-trimethoxybenzofuran-2-ylcarbonyl)-1,2,3,6-tetrahydropyrrolo[3,2-e]indole8-carboxylate was prepared by using 11.8 mg(22 μmol) of methyl (7bR,8aS)-6-trifluoromethyl-2-(5,6,7-trimethoxybenzofuran-2-ylcarbonyl)-1,2,8,8a-tetrahydrocyclopropa[c]pyrrolo[3,2-e]indol-4 (5H)-one-7-carboxylate in the same manner as in Example 34 in a yield of 12.0 mg (89%).

NMR (CDCl₃) δ: 3.21(1H, t, J=11 Hz), 3.75(1H, dd, J=3.0 Hz, J=11 Hz), 3. 90(3H, s), 3.95(3H, s), 3.99(3H, s), 4.28(3H, s), 4.49~4.59(1H, m), 4.67(1H, dd, J=9 Hz, J=11 Hz), 4.89(1H, d, J=12 Hz),6.79(1H, s), 7.69(1H, s), 8.53(1H, s), 9.87(1H, brs), 11.28(1H, brs)

$[\alpha]_D^{27}$=–48° (c=1.2, chloroform)

EXAMPLE 92

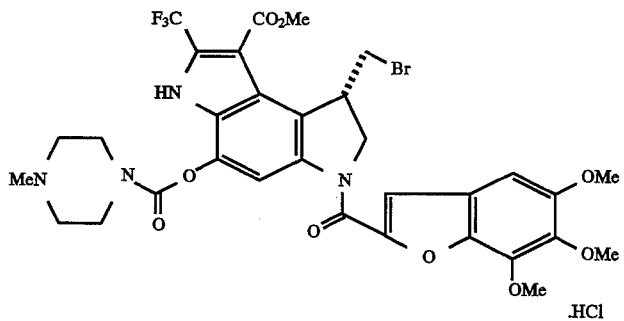

Methyl (1S)-1-bromomethyl-5-(4-methylpiperazin-1-ylcarbonyl)oxy-7-trifluoromethyl-3-(5,6,7trimethoxybenzofuran-2-ylcarbonyl)-1,2,3,6-tetrahydropyrrolo[3,2-e]indole-8-carboxylate was prepared by using 12.0 mg (19 μmol) of methyl (1S)-1-bromomethyl-5-hydroxy-7-trifluoromethyl-3-(5,6,7-trimethoxybenzofuran-2-ylcarbonyl)-1,2,3,6-tetrahydropyrrolo[3,2-e]indol-8-carboxylate in the same manner as in Example 46 in a yield of 9.5 mg (66%).

NMR (CDCl₃) δ: 2.37(3H, s), 2.52(4H, brs), 3.27(1H, t, J=9 Hz), 3.64(2H, brd, J=5 Hz), 3.78(3H, brd, J=6 Hz), 3.93(3H, s), 3.96(3H, s), 4.00(3H, s), 4.30(3H, s), 4.58~4.67 (2H, m), 4.93(1H, d, J=9 Hz), 6.84(1H, s), 7.54(1H, s), 8.36(1H, brs), 9.74(1H, brs)

$[\alpha]_D^{25}$=+30° (c=0.95,chloroform)

Hydrochloride salt: 9.4 mg (95%)

NMR (DMSOd₆) δ: 2.86(3H,brs), 3.06~3.42(4H,m), 3.54 (3H,t,J=9 Hz), 3.80(3H,s), 3.81~3.88(1H,s), 3.85(3H,s), 3.92(3H,s), 4.18(3H,s), 4.08~4.28(1H,m), 4.35~4.55(2H, m), 4.66(1H,d,J=11 Hz), 4.75(1H,t,J=10 Hz), 7.07(1H,s), 7.64(1H,s), 8.21(1H,s), 10.46(1H,brs), 13.19(1H,brs)

$[\alpha]_D^{24}$=+22° (c=0.13, methanol)

EXAMPLE 93

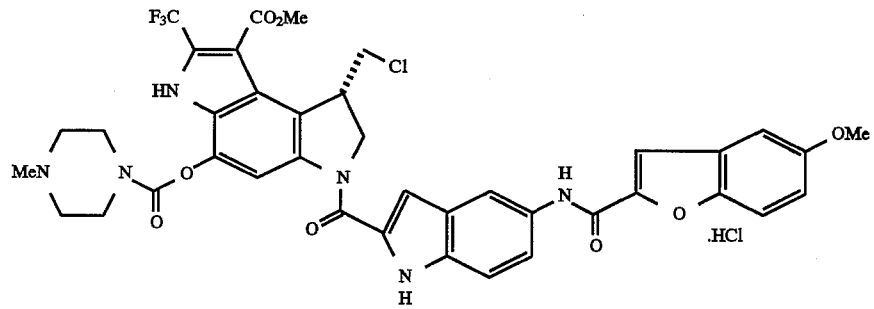

Methyl (1S)-1-chloromethyl-5-(4-methylpiperazin-1-ylcarbonyl)oxy-3-[5-(5-methoxybenzofuran-2-ylcarbonyl)

amino-1H-indol-2-ylcarbonyl]-7-trifluoromethyl-1,2,3,6-tetrahydropyrrolo[3,2-e]indole-8-carboxylate hydrochloride was prepared by using 5.6 mg (8.2 μmol) of methyl (1S)-1-chloromethyl-5-hydroxy-3-[5-(5-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate in the same manner as in Example 46 in a yield of 1.9 mg (2%).

NMR (CDCl₃) δ: 2.38(3H,s), 2.52(4H,brd,J=5 Hz), 3.40 (1H,t,J=10 Hz), 3.66(2H,brd,J=5 Hz), 3.76~3.95(3H,m), 3.87(3H,s), 3.99(3H,s), 4.55~4.65(2H,m), 4.75~4.85(1H, m), 7.07(1H,dd,J=3 Hz, J=9 Hz), 7.10(1 H,brs), 7.13(1H,d, J=2 Hz), 7.43~7.53(3H,m), 7.56(1H,s), 8.36(1H,s), 8.38 (1H,s), 9.37(1H,brs), 9.65(1H,brs)

$[\alpha]_D^{27}$=+44° (c=0.16, chloroform)

Hydrochloride salt:

NMR (DMSOd₆) δ: 2.85(3H, brs), 3.11~3.70(7H, m), 3.80~3.90(1H, m), 3.83(3H, s), 3.92(3H, s), 4.10~4.23(1H, m), 4.42(2H, brs), 4.59(1H, J=11 Hz), 4.81(1H, t, J=11 Hz), 7.09(1H, dd, J=3 Hz, J=9 Hz), 7.22(1H, s), 7.32(1H, d, J=2 Hz), 7. 50(1H, d, J=9 Hz), 7.63(2H, d, J=9 Hz), 7.70(1H, s), 8.20(1H, s), 8.22(1H, s), 10.46(1H, s), 10.85(1H, brs), 11.66(1H, s), 13.17(1H, brs)

$[\alpha]_D^{24}$=+12° (c=0.19, methanol)

EXAMPLE 94

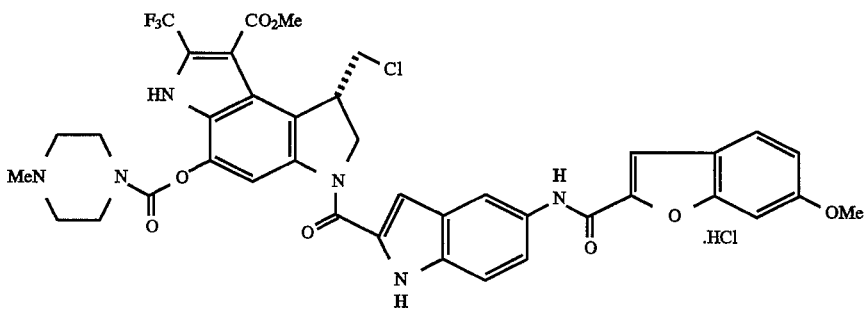

Methyl (1S)-1-chloromethyl-5-(4-methylpiperazin-1-ylcarbonyl)oxy-3-[5-(6-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate was prepared by using 6.5 mg (10 μmol) of methyl (1S)-1-chloromethyl-5-hydroxy-3-[5-(6-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate in the same manner as in Example 46 in a yield of 3.6 mg (46%).

NMR (CDCl₃) δ: 2.51(3H, s), 2.65(4H, brd, J=5 Hz), 3.40(1H, t, J=10 Hz), 3.65(2H, brd, J=5Hz), 3.79(2H, brs), 3.84~3.94(1H, m), 3.90(3H, s), 3.98(3H, s), 4. 51~4.61(2H, m), 4.72~4.82(1H, m), 6.96(1H, dd, J=2 Hz, J=9 Hz), 7.06(2H, d, J=3 Hz), 7.42(2H, s), 7.52~7.60(2H, m), 8.22 (1H, s), 8.33(1H, s), 8.35(1H, s), 9.43(1H, brs), 9.90(1H, br)

$[\alpha]_D^{26}$=+25° (c=0.36,chloroform)

Hydrochloride salt: 3.7 mg(100%)

NMR (DMSOd₆) δ: 2.86(3H, brs), 3.10~3.70(7H, m), 3.87(3H, s), 3.88~3.97(1H, m), 3.92(3H, s), 4.16(1H, brs), 4.42(1H, brs), 4.60(1H, d, J=11 Hz), 4.81(1H, t, J=10 Hz), 7.00(1H, dd, J=2 Hz, J=9 Hz), 7.22(1H, s), 7.27(1H, s), 7.50 (1H, d, J=9 Hz), 7.61(1H, d, J=9 Hz), 7.70(2H, d, J=8 Hz), 8.20(1H, s), 8.21(1H, s), 10.35(1H, s), 10.55(1H, brs), 11.64(1H, s), 13.15(1H, brs)

$[\alpha]_D^{24}$=+5.8° (c=0.13, methanol)

EXAMPLE 95

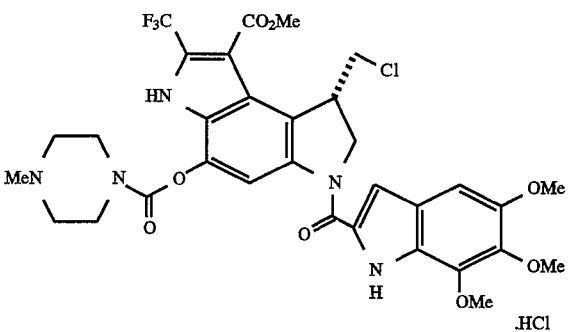

Methyl (1S)-1-chloromethyl-5-(4-methylpiperazin-1-ylcarbonyl)oxy-7-trifluoromethyl-3-[5-(5,6,7,-trimethoxybenzofuran-2-ylcarbonyl)amino-1H-indol-2-ylcarbonyl]-1,2,3,6-tetrahydropyrrolo[3,2-e]indole-8-carboxylate was prepared by using 5.7 mg (7.7 μmol) of methyl (1S)-1-chloromethyl-5-hydroxy-7-trifluoromethyl-3-[5-(5,6,7-trimethoxybenzofuran-2-ylcarbonyl)amino-1H-indol-2-ylcarbonyl]-1,2,3,6-tetrahydropyrrolo[3,2-e]indole-8-carboxylate in the same manner as in Example 46 in a yield of 1.1 mg (16%).

NMR (CDCl₃) δ: 2.38(3H, s), 2.53(4H, brd, J=5 Hz), 3.41(1H, dd, J=9 Hz, J=11 Hz), 3.66(2H, brd, J=6 Hz), 3.83(2H, brd, J=5 Hz), 3.86~3.94(1H, m), 3.93(3H, s), 3.97(3H, s), 3.99(3H, s), 4.23(3H, s), 4.55~4.65(2H, m), 4.80(1H, d, J=9 Hz(, 6.86(1H, s), 7.10(1H, d, J=2 Hz), 7.46~7.51(2H, m), 7.54(1H, s), 8.25(1H, s), 8.36(1H, s), 8.39(1H, s), 9.38(1H, brs), 9.70(1H, br)

$[\alpha]_D^{24}$=+31° (c=0.11, chloroform)

Hydrochloride salt: 1.0 mg(85%)

NMR (DMSOd₆) δ: 2.86(3H, s), 3.10~3.40(4H, m), 3.51 (2H, brs), 3.60~3.70(1H, m), 3.81(3H, s), 3.86(3H, s), 3.89~3.98(1H, m), 3.91(3H, s), 4.01~4.24(1H, m), 4.17(3H, s), 4.42(2H, brs), 4.60(1H, d, J=11 Hz), 4.81(1H, t, J=11 Hz), 7.08(1H, s), 7.22(1H, d, J=2 Hz), 7.51(1H, d, J=9 Hz), 7.57(1H, dd, J=2 Hz, J=9 Hz), 7.69(1H, s), 8.18(1H, brs), 8.20(1H, s), 10.33(1H, s), 10.70(1H, brs), 11.67(1H, brs), 13.16(1H, brs)

$[\alpha]_D^{24}$=+22° (c=0.13, methanol)

EXAMPLE 96

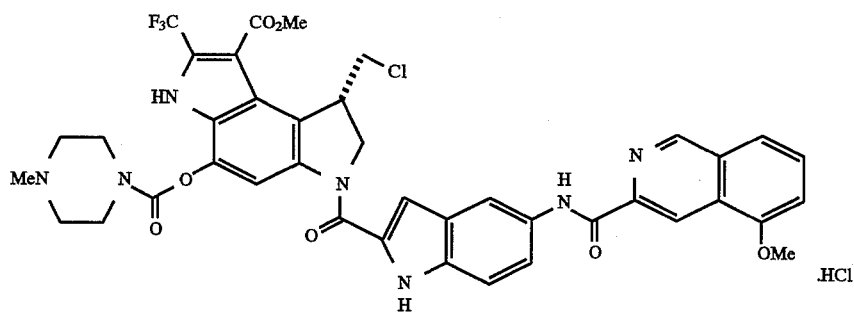

Methyl (1S)-1-chloromethyl-5-(4-methylpiperazin-1-ylcarbonyl)oxy-3-[5-(5-methoxyisoquinolin-3-ylcarbonyl)amino-1H-indol-2-ylcarbonyl]-7 -trifluoromethyl-1,2,3,6-tetrahydropyrrolo[3,2-e]indole-8-carboxylate was prepared by using 6.3 mg (9.1 µmol) of methyl (1S)-1-chloromethyl-5-hydroxy-3-[5-(5-methoxyisoquinolin-3-ylcarbonyl)amino-1H-indol-2-ylcarbonyl]-7-trifluoromethyl-1,2,3,6-tetrahydropyrrolo[3,2-e]indole-8-carboxylate in the same manner as in Example 46 in a yield of 5.6 mg (75%).

NMR (CDCl$_3$) δ: 2.32(3H, s), 2.49(4H, brs), 3.39(1H, t, J=10 Hz), 3.64(2H, brs), 3.73~3.89(3H, m), 3.98(3H, s), 4.06(3H, s), 4.50~4.65(2H, m), 4.77(1H, d, J=10 Hz), 7.03 (1H, s), 7.08(1H, dd, J=3 Hz, J=6 Hz), 7.40(1H, d, J=9 Hz), 7.49(1H, d, J=9 Hz), 7.55~7.66(2H, m), 8.35(1H, s), 8.38 (1H, s), 9.10(1H, s), 9.16(1H, s), 9.49(1H, brs), 10.25(1H, s)

$[\alpha]_D^{26}$=+35° (c=0.56, chloroform)

Hydrochloride salt: 5.6 mg (97%)

NMR (DMSOd$_6$) δ: 2.86(3H, d, J=5 Hz), 3.12~3.40(4H, m), 3.52~3.60(2H, m), 3.61~3.70(1H, m), 3.90~3.98(1H, m), 3.92,(3H, s), 4.08(3H, s), 4.18(1H, brd, J=13 Hz), 4.43(2H, brs), 4.61(1H, d, J=11 Hz), 4.82(1H, t, J=10 Hz), 7.23(1H, brs), 7.38(1H, d, J=8 Hz), 7.52(1H, d, J=9 Hz), 7.75(1H, brd, J=8 Hz), 7.78(1H, t, J=8 Hz), 7. 85(1H, d, J=8 Hz), 8.21(1H, s), 8.39(1H, brd), 8.83(1H, brs), 9.44(1H, brs), 10.70(2H, brs), 11.65(1H, brs), 13.16(1H, brs)

$[\alpha]_D^{24}$=+31° (c=0.13, methanol)

Methyl (1S)-1-chloromethyl-5-(4-methylpiperazin-1-ylcarbonyl)oxy-7-trifluoromethyl-3-[5-(5,6,7-trimethoxyisoquinolin-3-ylcarbonyl)amino]-1H-indol-2-ylcarbonyl]-1,2,3,6-tetrahydropyrrolo[3,2-e]indole-8-carboxylate was prepared by using 20.4 mg (27 µmol) of methyl (1S)-1-chloromethyl-5-hydroxy-7-trifluoromethyl-3-[5-(5,6,7-trimethoxyisoquinolin-3-ylcarbonyl)amino]-1H-indol-2-ylcarbonyl]-1,2,3,6-tetrahydropyrrolo-[3,2-e]indole-8-carboxylate in the same manner as in Example 46 in a yield of 12.4 mg (52%).

NMR (CDCl$_3$) δ: 2.30(3H, s), 2.47(4H, s), 3.39(1H, t, J=9 Hz), 3.63(2H, s), 3.78(2H, s), 3.84(1H, dd, J=3 Hz, J=11 Hz), 3.96(3H, s), 4.04(3H, s), 4.05(3H, s), 4.12(3H, s), 4.52~4.59(2H, m), 4.74(1H, d, J=10 Hz), 7.01(1H, s), 7.12 (1H, s), 7.38(1H, d, J=9 Hz), 7.47(1H, d, J=9 Hz), 8.32(1H, s), 8.38(1H, s), 8.90(1H, s), 9.02(1H, s), 9.57(1H, br), 10.20(1H, s)

$[\alpha]_D^{26}$=+28° (c=0.83, chloroform)

Hydrochloride salt:

$[\alpha]_D^{26}$=+38° (c=0.40, methanol)

EXAMPLE 97

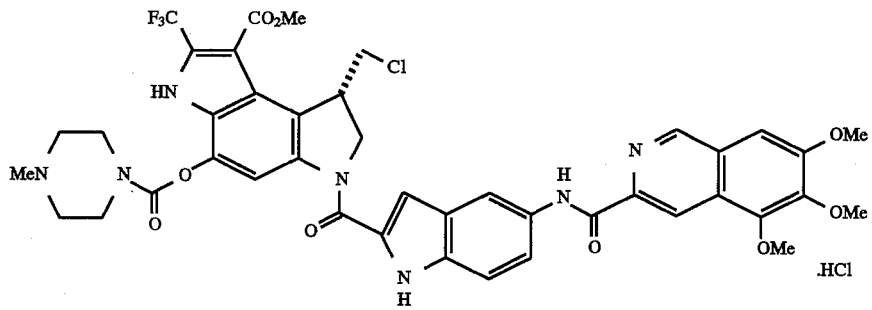

EXAMPLE 98

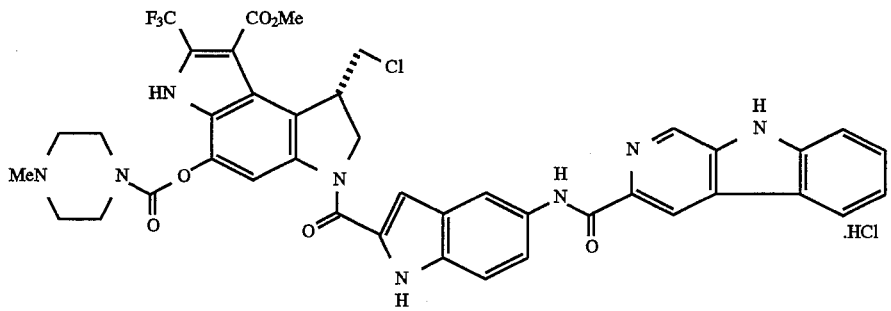

Methyl (1S)-1-chloromethyl-5-(4-methylpiperazin-1-ylcarbonyl)oxy-3-[5-[(9H-pyrido[3,4-b]indol-3-ylcarbonyl)amino]-1H-indol-2-ylcarbonyl]-7-trifluoromethyl-1,2,3,6-tetrahydropyrrolo[3,2-e]indole-8-carboxylate was prepared by using 20.3 mg (29 μmol) of methyl (1S)-1-chloromethyl-5-hydroxy-3-[5-[(9H-pyrido[3,4-b]indol-3-ylcarbonyl)amino]-1H-indol-2-ylcarbonyl]-7-trifluoromethyl-1,2,3,6-tetrahydropyrrolo[3,2-e]indole-8-carboxylate in the same manner as in Example 46 in a yield of 13.6 mg (57%).

$[\alpha]_D^{26}$=+51° (c=0.91, tetrahydrofuran)

Hydrochloride salt:

NMR (DMSOd$_6$) δ: 2.87(3H, brs), 3.17~3.43(3H, m), 3.48~3.63(4H, m), 3.89~3.95(1H, m), 3.92(3H, s), 4.16(1H, m), 4.43(2H, brs), 4.62(1H, d, J=11 Hz), 4.82(1H, t, J=10 Hz), 7.23(1H, s), 7.37(1H, t, J=8 Hz), 7.54(1H, d, J=9 Hz), 7.66(1H, t, J=8 Hz), 7.73(1H, d, J=8 Hz), 8.21(1H, s), 8.38(1H, s), 8.46(1H, d, J=8 Hz), 9.06(1H, s), 9.16(1H, br), 10.67(1H, s), 10.97(1H, br), 11.65(1H, s), 12.24(1H, s), 13.16(1H, s)

$[\alpha]_D^{26}$=+37° (c=0.40, dimethylformamide)

carboxylate was prepared by using 23.0 mg (34 μmol) of methyl (1S)-1-chloromethyl-5-hydroxy-3-[5-[(7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate in the same manner as in Example 46 in a yield of 17.4 mg(64%).

NMR (CDCl$_3$) δ: 2.30(3H, s), 2.36~2.48(4H, m), 2.97 (1H, t, J=10 Hz), 3.47(2H, m), 3.67(1H, m), 3.77(2H, s), 3.94(3H, s), 4.11(3H, s), 4.23~2.33(2H, m), 4.51(1H, d, J=10 Hz), 6.90(1H, s), 6.98(1H, d, J=7 Hz), 7.24~7.34(3H, m), 7.43(1H, dd, J=2 Hz, J=9 Hz), 7.54(1H, s), 7.73(1H, s), 8.44(1H, s), 8.66(1H, s), 10.45(1H, br)

$[\alpha]_D^{26}$=+8.3° (c=1.2, chloroform)

Hydrochloride salt:

NMR (DMSOd6) δ: 2.86(3H, s), 3.20~3.69(6H, m, ), 3.62(1H, t, J=10 Hz), 3.92(3H, s), 3.94(1H, m), 4.01(3H, s), 4.19(1H, m), 4.43(2H, m), 4.63(1H, d, J=10 Hz), 4.78(1H, t, J=9 Hz), 7.07(1H, d, J=7 Hz), 7.19(1H, d, J=2 Hz), 7.26(1H, t, J=8 Hz), 7.34(1H, d, J=7 Hz), 7.51(1H, d, J=9

EXAMPLE 99

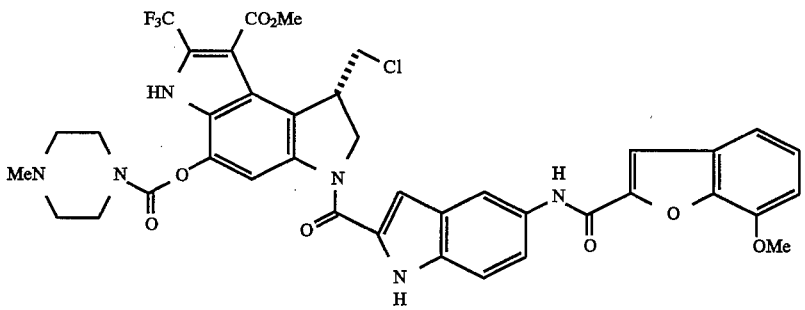

Methyl (1S)-1-chloromethyl-3-[5[(7-methoxybenzofuran-2-ylcarbonyl)amino]-1H-indol-2-ylcarbonyl]-5-(4-methylpiperazin-1-ylcarbonyl)oxy-7-trifluoromethyl-1,2,3,6-tetrahydropyrrolo[3,2-e]indole-8-

Hz), 7.62(1H, dd, J=1Hz, J=9 Hz), 7.75(1H, s), 8.20(1H, s), 8.23(1H, d, J=1 Hz), 10.40(1H, s), 11.21(1H, brs), 11.63(1H, s), 13.11(1H, s)

$[\alpha]_D^{26}$=+26° (c=0.40, methanol)

EXAMPLE 100

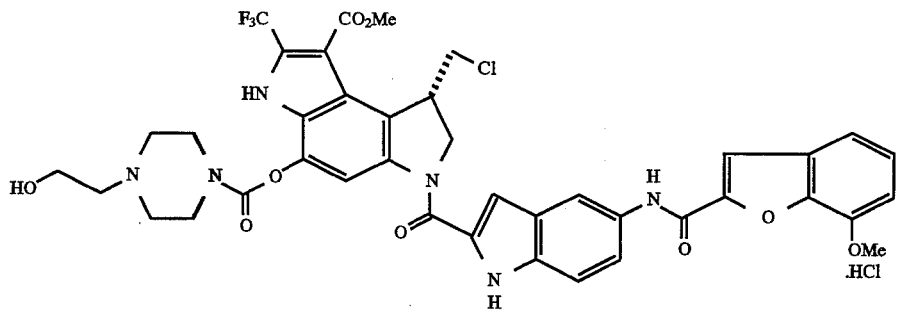

Methyl (1S)-1-chloromethyl-5-[4-(2-hydroxyethyl) piperazin-1-ylcarbonyl)oxy-3-[5-(7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate hydrochloride was prepared by using 25.6 mg (37 μmol) of methyl (1S)-1-chloromethyl-5-hydroxy-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate and 6.8 μl (56 μmol) of 1-(2-hydroxyethyl)piperazine in the same manner as in Example 46 in a yield of 22.2 mg (69%).

NMR (CDCl$_3$) δ: 2.48~2.74(6H, m), 3.23(1H, t, J=9 Hz), 3.58(2H, brs), 3.67(2H, t, J=5 Hz), 3.76~3.85(3H, m), 3.97(3H, s), 4.09(3H, s), 4.46~4.55(2H, m), 4.67~4.75(1H, m), 6.97(1H, d, J=7 Hz), 7.04(1H, d, J=2 Hz), 7.26(1H, d, J=8 Hz), 7.31(1H, t, J=7 Hz), 7.43(1H, d, J=9Hz), 7.50(1H, dd, J=2 Hz, J=9 Hz), 7.60(1H, s), 8.04(1H, s), 8.40(1H, s), 8.56(1H, s), 9.52(1H, brs), 9.99(1H, brs)

$[\alpha]_D^{25}$=−15° (c=1.9, chloroform)

Hydrochloride salt:

NMR (DMSOd$_6$) δ: 3.14~3.55(6H, m), 3.56~3.77(3H, m), 3.84(2H, brs), 3.90~3.97(1H, m), 3.92(3H, s), 4.00(3H, s),4.10~4.20(1H, m),4.43(2H, brs), 4.60(1H, d, J=11 Hz), 4.81(1H, t, J=10 Hz), 5.43(1H, brs), 7.10(1H, d, J=8 Hz), 7.23(1H, t, J=8 Hz), 7.37(1H, d, J=8 Hz), 7.51(1H, d, J=9 Hz), 7.62(1H, dd, J=2 Hz, J=9 Hz), 7.78(1H, s),8.20(1H, s),8.21(1H, brs),10.45(1H, s),10.62(1H, brs),11.67(1H, brs),13. 22(1H, brs)

$[\alpha]_D^{27}$=+25° (c=0.75, methanol)

Methyl (1S)-1-chloromethyl-5-[4-(2-(2-hydroxyethoxy)ethyl)piperazin-1-ylcarbonyl]oxy-3-[5-(8-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate was prepared by using 30.7 mg (44 μmol) of methyl (1S)-1-chloromethyl-5-hydroxy-3-[-5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate and 11.6 mg (67 μmol) of 1-[2-(2-hydroxyethyl)ethyl]piperazine in the same manner as in Example 46 in a yield of 17.6 mg (45%).

NMR (CDCl$_3$) δ: 2.55~2.75(6H, m), 3.31(1H, t, J=10 Hz), 3.50~3.90(10H, m), 3.92~4.02(1H, m), 3.98(3H, s), 4.08(3H, s), 4.40~4.59(2H, m), 4.72(1H, d, J=10 Hz), 6.95 (1H, d, J=8 Hz), 7.06(1H, s), 72.0~7.35(2H, m), 7.40~7.55 (2H, m), 7.61(1H, s), 8.16(1H, s), 8.35(1H, s), 8.50(1H, s), 9.43(1H, brs), 9.95(1H, brs)

$[\alpha]_D^{27}$=+19° (c=1.8, chloroform)

Hydrochloride salt: 13.8 mg (75%)

NMR (DMSOd$_6$) δ: 3.15~3.45(6H, m), 3.50~3.78(7H, m), 3.78~3.90(2H, m), 3.90~3.97(1H, m), 3.92(3H, s), 4.00 (3H, s), 4.17~4.20(1H, m), 4.42(2H, brs), 4.59(1H, d, J=11 Hz), 4.70~4.85(1H, m), 4.81(1H, t, J=10 Hz), 7.11(1H, d, J=8 Hz), 7.23(1H, s), 7.29(1H, t, J=8 Hz), 7.37(1H, d, J=8 Hz), 7.51(1H, d, J=9 Hz), 7.61(1H, dd, J=2 Hz, J=9 Hz), 7.78(1H, s), 8.21(1H, brs), 10.42(1H, s), 10.45(1H, brs), 11. 67(1H, brs), 13.22(1H, brs)

$[\alpha]_D^{27}$=⩽19° (c=0.45, methanol)

EXAMPLE 101

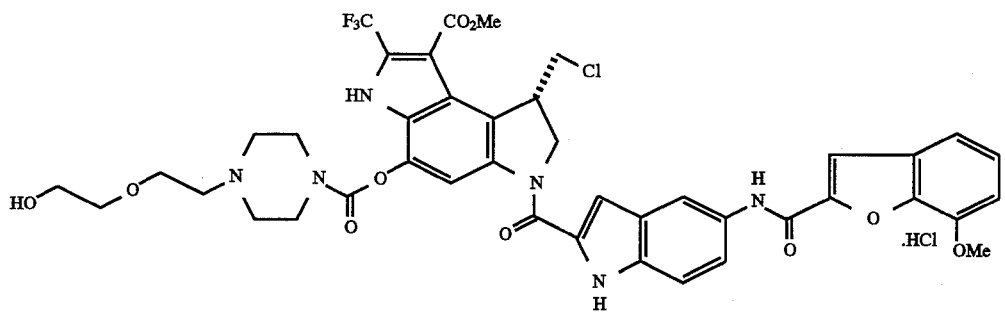

EXAMPLE 102

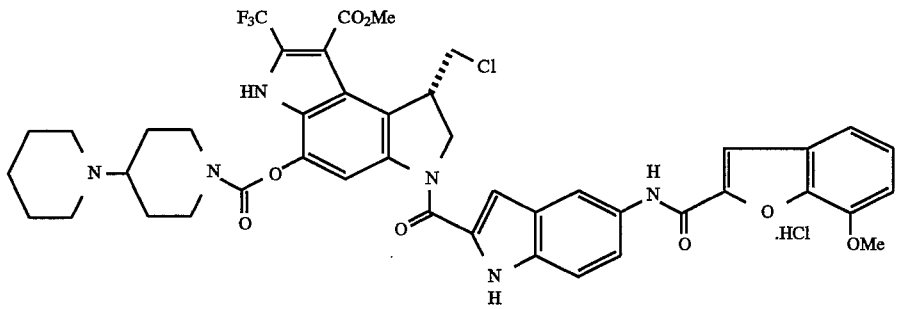

Methyl (1S)-1-chloromethyl-3-[5-(7-methoxybenzofuran-2-ylcarbonyl)amino-1H-indol-2-ylcarbonyl]5-(4-piperidinopiperidin-1ylcarbonyl)oxy-7-trifluoromethyl-1,2,3,6-tetrahydropyrrolo[3,2-e]indole-8-carboxylate hydrochloride was prepared by using 24.mg (35 µmol) of methyl (1S)-1-chloromethyl-5-hydroxy-3-[5-(7-methoxybenzofuran-2-ylcarbonyl)amino-1-H-indol-2-ylcarbonyl]-7-trifluoromethyl-1,2,3,6-tetrahydropyrrolo[3,2-e]indole-8-carboxylate and 10.6 mg (63 µmol) of 4-piperidinopiperidine in the same manner in Example 46 in a yield of 16.5 mg (51%).

NMR (CDCl$_3$) δ: 1.35~1.75(6H, m), 1.80~1.95(2H, m), 2.52(6H, brs), 2.70~2.85(1H, m), 2.95~3.25(3H, m), 3.75 (1H, t, J=10 Hz), 3.96(3H, s), 4.09(3H, s), 4.15~4.30(1H, m), 4.32~4.50(3H, m), 4.55~4.65(1H, m), 6.95~7.00(2H, m), 7.25(1H, d, J=8 Hz), 7.30(1H, t, J=8Hz), 7.36~7.50(2H, m), 7.57(1H, s), 7.92(1H, brs), 8.39(1H, brs), 8.61(1H, brs), 9.63(1H, brs)

$[\alpha]_D^{24}$=+5.0° (c=1.5, chloroform)

Hydrochloride salt:

NMR (DMSOd$_6$) δ: 1.85(6H, brs), 2.20(2H, brs), 2.98 (2H, brs), 3.15(1H, t, J=10 Hz), 3.30~3.54(4H, m), 3.64(1H, t, J=9 Hz), 3.88~3.98(1H, m), 3.91(3H, s), 4.00(3H, s), 4.14~4.26(1H, m), 4.88~4.98(2H, m), 4.60(1H, d, J=11 Hz), 4.80(1H, t, J=10 Hz), 7.10(1H, d, J=8 Hz), 7.22(1H, brs), 7.28(1H, t, J=8 Hz), 7.37(1H, d, J=7 Hz), 7.51(1H, d, J=9 Hz), 7.61(1H, dd, J=2 Hz, J=9 Hz), 7.78(1H, s), 8.15(1H, s), 8.32(1H, s), 10.16(1H, brs), 10.40(1H, s), 11.68(1H, s), 13.20(1H, s)

$[\alpha]_D^{27}$=+2.2° (c=0.47, methanol)

Methyl (1S)-1-chloromethyl-5-[4-(2-dimethylaminoethyl)piperazin-1-ylcarbonyl)oxy-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate hydrochloride was prepared by using 2.52 mg (37 µmol) of methyl (1S)-1-chloromethyl-5-hydroxy-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8 -carboxylate and 8.6 mg (55 µmol) of 4-(2-dimethylaminoethyl)piperazine in the same manner as in Example 46 in a yield of 9.9 mg (28%).

NMR (CDCl$_3$)

NMR (CDCl$_3$) δ: 2.19(3H, s), 2.20(3H, s), 2.30~2.60(8H, m), 3.00~3.16(1H, m), 3.40~3.58(2H, m), 3.58~3.75(3H, m), 3.89(3H, s), 4.03(3H, s), 4.35(2H, brs), 4.56(1H, d, J=8Hz), 6.86~6.94(2H, m), 7.16~7.26(2H, m), 7.29~7.36 (1H, m), 7.38~7.44(1H, m), 7.50(1H, s), 7.86(1H, brs), 8.34(1H, s), 8.55(1H, s), 9.26(1H, brs), 9.50(1H, brs)

$[\alpha]_D^{24}$=+7.2° (c=0.82, chloroform)

Hydrochloride salt:

NMR (DMSOd$_6$) δ: 2.80~2.92(8H, m), 3.20~3.58(8H, m), 3.65(1H, dd, J=7 Hz, J=11 Hz), 3.90~3.98(1H, m), 3.92(3H, s), 4.00(3H, s), 4.08~4.24(1H, m), 4. 40~4.47(.2H, m), 4.60(1H, d, J=11 Hz), 4.81(1H, dd, J=9 Hz, J=11 Hz), 7.10(1H, d, J=8 Hz), 7.22(1H, d, J=2 Hz), 7.32(1H, t, J=8 Hz), 7.37(1H, d, J=8 Hz), 7.51(1H, d, J=9 Hz), 7.62(1H, dd, J=2 Hz, J=9 Hz), 7.78(1H, s), 8.19(1H, s), 8.22(1H, s), 10.45(1H, s), 11.67(1H, s), 13.20(1H, s)

$[\alpha]_D^{27}$=+2.3° (c=0.27, methanol)

EXAMPLE 103

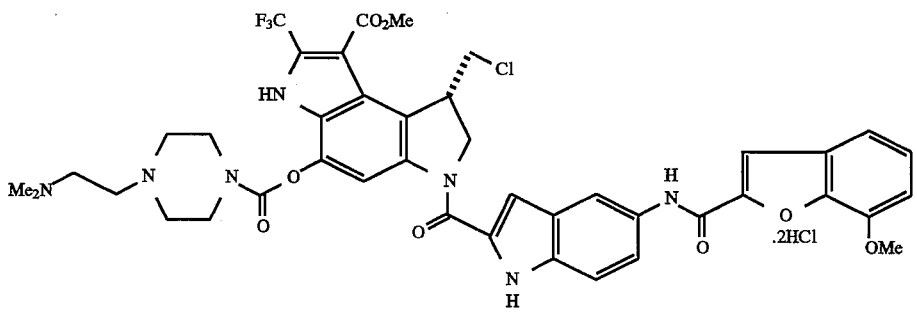

EXAMPLE 104

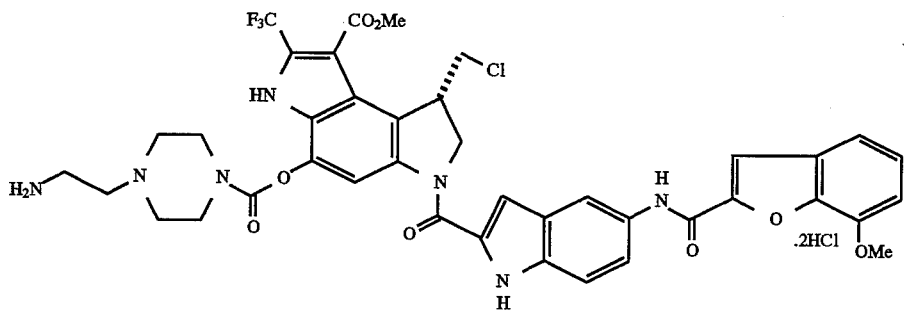

Methyl (1S)-5-[4-(2-aminoethyl)piperazin-1-ylcarbonyl)oxy-1-chloromethyl-3-[5-(8-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate hydrochloride was prepared by using 26.0 mg (38 μmol) of methyl (1S)-1-chloromethyl-5-hydroxy-3-[5-(8-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate and 7.4 μl (56 μmol) of 4-(2-aminoethyl)piperazine in the same manner as in Example 46 in a yield of 9.1 mg (27%).

NMR (CDCl₃) δ: 2.40~2.65(6H, m), 2.80~2.90(2H, m), 3.30~3.42(1H, m), 3.55~3.95(5 H, m), 3.99(3H, s),4.08(3H, s),4.50~4.62(2H, m), 4.75~4.85(1H, m), 6.96(1H, d, J=7 Hz), 7.10(1H, s), 7.26~7.33(2H, m), 7.47(1H, d, J=9 Hz), 7.50~7. 55(1H, m), 7.61(1H, s), 8.19(1H, s), 8.37(1H, s), 8.53(1H, s), 9.10(1H, brs), 9.45(1H, brs)

$[\alpha]_D^{23}$=+25° (c=0.39, tetrahydrofuran)

Hydrochloride salt:

NMR (DMSOd₆) δ: 2.80~3.70(10H, m), 3.64(1H, t, J=8 Hz), 3.87~3.98(1H, m), 3.92(3H, s), 4.00(3H, s), 4.10~4.24 (1H, m), 4.43(2H, brs), 4.60(1H, d, J=12 Hz), 4.82(1H, t, J=10 Hz), 7.11(1H, d, J=8 Hz), 7.23(1H, s), 7.39(1H, t, J=8 Hz), 7.47(1H, d, J=8Hz), 7.61(1H, d, J=9 Hz), 7.71(1H, brd, J=9 Hz), 7.88(1H, s), 8.31(1H, s), 8.41(1H, s), 10.58(1H, s), 11.78(1H, brs), 13.34(1H, brs)

$[\alpha]_D^{27}$=+11° (c=0.21, methanol)

EXAMPLE 105

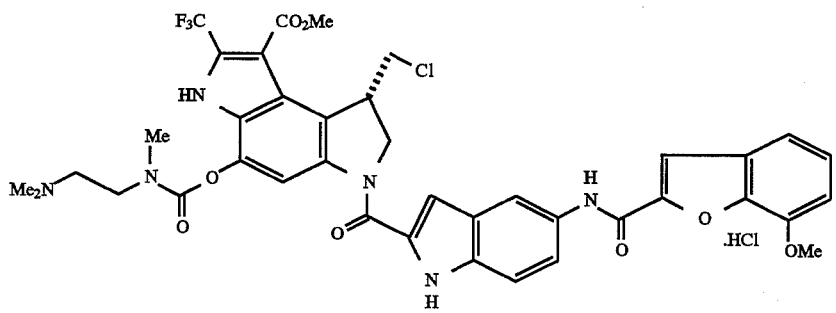

Methyl (1S)-1-chloromethyl-3-(7-methoxybenzofuran-2-ylcarbonyl)amino-1H-indol-2-ylcarbonyl]-7-trifluoromethyl-5-(N, N, N'-trimethylethylenediamine-1-ylcarbonyl)oxy-1,2,3,6-tetrahydropyrrolo[3,2-e]indole-8-carboxylate was prepared by using 23.9 mg (35 μmol) of methyl (1S)-1-chloromethyl-5-hydroxy-3-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate and 6.6 μl (52 μmol) of N, N, N'-trimethylethylenediamine in the same manner as in Example 46 in a yield of 11.9 mg (42%).

NMR (CDCl₃) δ: 2.34(6H, s), 2.45~2.58(2H, m), 2.73~2.58(2H, m), 3.07(3H, s), 3.35(1H, t, J=10 Hz), 3.84 (1H, d, J=11 Hz), 3.96(3H, s), 4.06(3H, s), 4.30~4.50(2H, m), 4.72(1H, t, J=10 Hz), 6.92(1H, d, J=8 Hz), 7.07(1H, s), 7.23(1H, d, J=8 Hz), 7.28(1H, t, J=8 Hz), 7.31~7.45(2H, m), 7.61(1H, s), 8.26(1H, brs), 8.38(1H, brs), 8.47(1H, brs), 9.63(1H, brs), 10.40(1H, brs)

$[\alpha]_D^{27}$=+99° (c=0.60, chloroform)

Hydrochloride salt: 8.4 mg(67%)

$[\alpha]_D^{27}$ =+35° (c=0.11, methanol)

SIMS (positive, glycerol) m/z: 809 [M+H]⁺

EXAMPLE 106

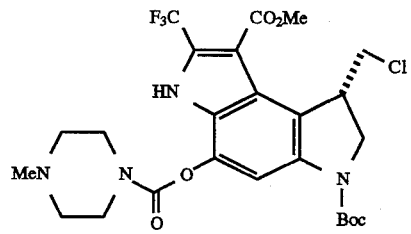

Methyl (1S)-3-(t-butoxycarbonyl)-1-chloromethyl-5-(4-methylpiperazin-1-ylcarbonyl)oxy-7-trifluoromethyl-1,2,3, 6-tetrahydropyrrolo[3,2-e]indole-8-carboxylate was prepared by using 48.9 mg (0.1 mmol) of methyl (1S)-3-(t-butoxycarbonyl)-1-chloromethyl-5-hydroxy-7-trifluoromethyl-1,2,3,6-tetrahydropyrrolo[3,2-e]indole-8-carboxylate in the same manner as in Example 46 in a yield of 52.3 mg (91%).

NMR (CDCl₃) δ: 1.57(9H, s), 2.37(3H, s), 2.50(4H, brs), 3.38(1H, t, J=10 Hz), 3.62(2H, brs), 3.75(2H, brs), 3.80(1H, dd, J=3 Hz, J=11 Hz), 3.96(3H, s), 4.00(1H, dd, J=9 Hz, J=11 Hz), 4.21(1H, d, J=11 Hz), 4.35(1H, m), 7.98(1H, brs), 9.59(1H, br)

$[\alpha]_D^{25}$=–51° (c=0.20, chloroform)

EXAMPLE 107

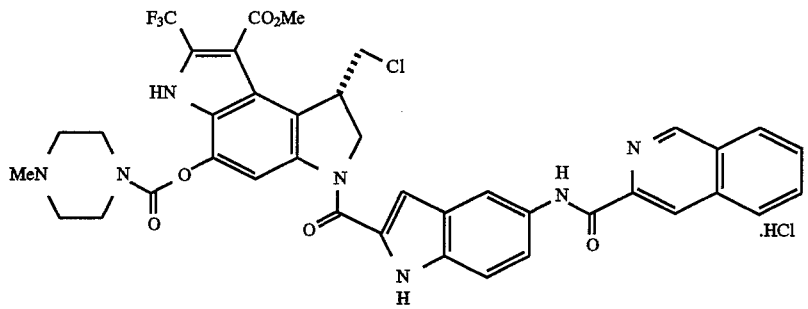

Methyl (1S)-1-chloromethyl-3-[5-[(isoquinolin-3-ylcarbonyl)amino]-1H-indol-2-ylcarbonyl]-5-(4-methylpiperazin-1-ylcarbonyl)oxy-7-trifluoromethyl-1,2,3,6-tetrahydropyrrolo[3,2-e]indole-8-carboxylate was prepared by using 40.2 mg (70 µmol) of methyl (1S)-3-(t-butoxycarbonyl)-1-chloromethyl-5-(4-methylpiperazin-1-ylcarbonyl)oxy-7trifluoromethyl-1,2,3,6-tetrahydropyrrolo[3,2-e]indole-8-carboxylate and 23.2 mg (70 µmol) of 3-(5-isoquinolin-3-ylcarbonyl)amino-1H-indole-2-carboxylic acid in the same manner as in Example 6 in a yield of 40.5 mg (74%).

Hydrochloride salt:

NMR (DMSOd₆) δ: 2.88(3H, s), 3.20~3.38(4H, m), 3.52 (2H, m), 3.65(1H, brs), 3.92(3H, s), 3.95(1H, m), 4.19(1H, d, J=12 Hz), 4.43(2H, brs), 4.61(1H, d, J=11 Hz), 4.82(1H, t, J=10 Hz), 7.23(1H, s), 7.52(1H, d, J=9 Hz), 7.76(1H, d, J=9 Hz), 7.86(1H, dd, J=1 Hz, J=7 Hz), 7.92(1H, dt, J=1 Hz, J=7 Hz), 8.21(1H, s), 8.27(1H, d, J=8 Hz), 8.32(1H, d, J=8 Hz), 8.41(1H, s), 8.73(1H, s), 9.49(1H, s), 10.45(1H, br), 10.71(1H, s), 11.65(1H, s), 13.14(1H, s)

$[\alpha]_D^{25}$=+40° (c=0.20, dimethylformamide)

(S,S)-3-3'-[Carbonylbis(imino-1H-indol-5,2-dicarbonyl)]bis-[1-chloromethyl-5-hydroxy-7-trifluoromethyl-1,2,3,6-tetrahydropyrrolo[3,2-e]indole-8-carboxylic acid methyl ester]was prepared by using 4.4 mg (12 µmol) of 5,5'-(carbonyldiimino)bis-1H-indole-2-carboxylic acid in the same manner as in Example 6 in a yield of 10.2 mg (86%).

NMR (DMSOd₆) δ: 3.51(1H×2, t, J=11 Hz), 3.81(1H×2, m), 3.88(3H×2, s), 4.28(1H×2, m), 4.53(1H×2, d, J=11 Hz), 4.70(1H×2, t, J=11 Hz), 7.09(1H×2, s), 7.28(1H×2, dd, J=2 Hz, J=9 Hz), 7.42(1H×2, d, J=9 Hz), 7.86(1H×2, s), 7.95 (1H×2, brs), 8.47(1H×2,s),10.57(1H×2,s),11.59(1H×2,s), 13.08(1H×2, brs)

$[\alpha]_D^{23}$=+74° (c=0.16, tetrahydrofuran)

EXAMPLE 108

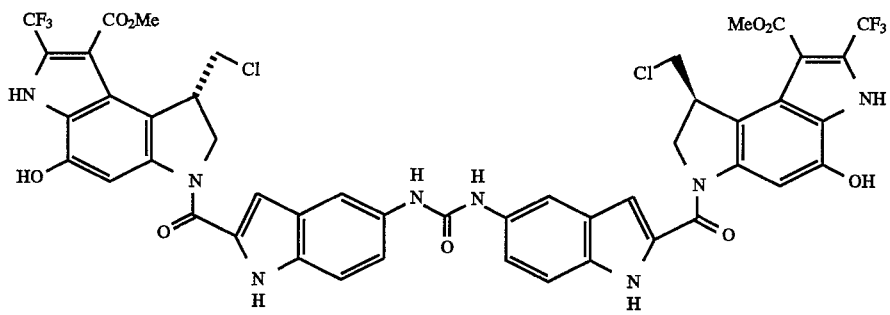

EXAMPLE 109

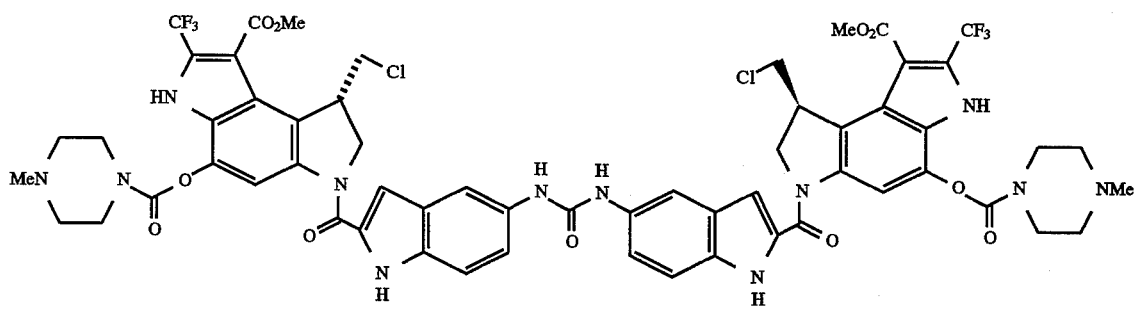

(S,S)-3-3'-[Carbonylbis(imino-1H-indol-5,2-dicarbonyl)]bis-[1-chloromethyl-5-(4-methylpiperazin-1-ylcarbonyl)oxy- 7-trifluoromethyl-1,2,3,6-tetrahydropyrrolo[3,2-e]indole-8-carboxylic acid methyl ester] was prepared by using 11.5 mg (20 μmol) of methyl (1S)-3-(t-butoxycarbonyl)-1-chloromethyl-5-(4-methylpiperazin-1-ylcarbonyl)oxy-7-trifluoromethyl-1,2,3,6-tetrahydropyrrolo[3,2-e]indole-8-carboxylate and 3.8 mg (10 μmol) of 5,5'-(carbonyldiimino)bis-1H-indole-2-carboxylic acid in the same manner as in Example 6 in a yield of 8.4 mg (65%).

NMR (DMSOd$_6$) δ: 2.29(3H×2, s), 2.50(4H×2, br), 3.49 (2H×2, brs), 3.61(1H×2, t, J=9Hz), 3.72(2H×2, brs), 3.90 (3H×2, s), 3.93(1H×2, dd, J=3 Hz, J=11 Hz), 4.42(1H×2, m), 4.59(1H×2, d, J=11 Hz), 4.77(1H×2, t, J=10 Hz), 7.11(1H×2, s), 7.28(1H×2, d, J=9 Hz), 7.43(1H×2, d, J=9 Hz),7.88(1H× 2, s), 8.10(1H×2, br), 8.50(1H×2, s), 11.55(1H×2, s), 13.10 (1H×2, br)

$[\alpha]_D^{25}$=+36° (c=0.62, chloroform:methanol=5:1)

Hydrochloride salt:

$[\alpha]_D^{25}$=+34° (c=0.20, dimethylformamide)

EFFECTS OF INVENTION

Experiment 1
Activity against Tumor Cell Growth

Using a culture medium RPMI1640 supplemented with 10% inactivated bovine fetal serum, 2 mM glutamine, 100 μ/ml kanamycin sulfate, and 5 μM 2-hydroxyethyldisulfide (This culture medium is hereinafter referred to simply as "culture medium"), P388 mouse leukemia cells were diluted to a concentration of 1.5×10$^5$ cells/ml in the culture medium, and were placed in each well of 96-well multiplate in 60 μl portions. Separately, the test compound was dissolved in dimethylsulfoxide and was adequately diluted with the culture medium. The diluted solution containing test compound was added to the wells of the above plate respectively in 60 μl portions. Then the cells were incubated in a CO$_2$-incubator (5% CO$_2$, 37° C.) for 72 hours.

The surviving cell numbers were measured according to the Mosmann's method (J. Immunol. Meth., 65 55–63, 1983) as follows. A 2.5 mg/ml solution of MTT (3-[4,5-dimethylthiazol-2-yl]-2,5-diphenyltetrazolium bromide) in Dulbecco's phosphate buffer solution (PBS) was prepared and added to each of the wells by 20 μl. The cells were further incubated for 3 hours. A 150 μl portion of 0.04N hydrochloric acid-isopropanol solution was added to each of the wells, and MTT-formazane formed was allowed to dissolve by pipetting. The absorbance of the solutions was measured at 540 nm taking the no-cell-containing [solution as the background. The 50% growth inhibition concentration (IC$_{50}$) was calculated from ratio of the absorbances of the treated samples to the absorbance of the no-medicine-treated sample, and from the concentration of the test compound.

The results are shown in Table 1.

TABLE 1

Inhibitory Activity against Tumor Cell Growth

| Example No. | IC$_{50}$ (ng/ml) |
|---|---|
| 6 | 0.24 |
| 8 | 0.21 |
| 9 | 0.76 |
| 10 | 0.52 |
| 11 | 0.67 |
| 13 | 0.21 |
| 14 | 0.10 |
| 15 | 0.83 |
| 16 | 0.16 |
| 17 | 0.09 |
| 18 | 0.09 |
| 19 | 0.11 |
| 20 | 0.24 |
| 22 | 0.23 |
| 23 | 0.86 |
| 24 | 0.53 |
| 25 | 0.63 |
| 27 | 0.17 |
| 28 | 0.11 |
| 29 | 1.2 |
| 30 | 0.22 |
| 31 | 0.10 |
| 32 | 0.09 |
| 33 | 0.17 |
| 34 | 0.15 |
| 36 | 1.3 |
| 37 | 0.61 |
| 39 | 0.20 |
| 40 | 0.08 |
| 41 | 1.6 |
| 42 | 0.13 |
| 43 | 0.10 |
| 44 | 0.07 |
| 45 | 0.12 |
| 46 | 22 |
| 47 | 31 |
| 48 | 80 |
| 49 | 89 |
| 50 | 4.5 |
| 63 | 0.55 |
| 64 | 3.9 |
| 65 | 0.11 |
| 66 | 0.77 |
| 67 | 0.026 |
| 68 | 0.051 |
| 69 | 0.046 |
| 70 | 2.0 |
| 74 | 1.3 |
| 75 | 0.74 |
| 76 | 0.20 |

TABLE 1-continued

Inhibitory Activity against Tumor Cell Growth

| Example No. | IC$_{50}$ (ng/ml) |
| --- | --- |
| 77 | 0.23 |
| 78 | 0.33 |
| 79 | 2.1 |
| 84 | 1.7 |
| 86 | 1.1 |
| 90 | 0.90 |
| 97 | 5.8 |
| 98 | 5.7 |
| 107 | 4.6 |
| 108 | 0.0070 |
| 109 | 53 |

Experiment 2
Antineoplastic Activity

The test compound was dissolved in dimethylsulfoxide, and the solution was adequately diluted with 10% Emulfore EL620(produced by Rhone Poulenc Co.) to prepare the test compound solution. The antineoplastic activity was evaluated as below.

(1) Evaluation with mice having P388 cells transplanted in abdominal cavity:

To the abdominal cavity of a female mouse (CDF$_1$ strain, 8 to 9 week age), 1×10$^6$ P388 cells were transplanted. Next day, the test medicine solution was injected intraperitonealy in a single dose. Five to eight mice were employed for the solvent-dosed control group, and two mice were employed for each of the dosed groups. The antineoplastic effect was evaluated by the ratio (T/C, %) of the average survival days of the dosed group (T) to the average survival days of the solvent-dosed control group(C). The T/C ratio of 130% or more is evaluated to be effective. The results are shown in Table 2.

TABLE 2

Antineoplastic Activity for Mice Having P388 Cells Transplanted in Abdominal Cavity

| Example No. | i.p. Dosage (mg/kg) | T/C (%) |
| --- | --- | --- |
| 6 | 0.5 | 206 |
| 8 | 1.0 | 198 |
| 20 | 0.125 | 194 |
| 22 | 0.125 | 169 |
| 23 | 0.25 | Both cured |
| 24 | 0.125 | Both cured |
| 34 | 0.125 | 189 |
| 36 | 0.125 | 384 |
| 46 | 4 | 221 |
| 47 | 0.5 | Both cured |
| 48 | 0.5 | Both cured |
| 49 | 0.5 | Both cured |

"Cured": Survived for 60 days or longer (2) Evaluation with mice having Sarcoma-180 cells transplanted subcutaneously:

To the lateral region of a female mouse (CDR strain, 5 to 6 week age), 3.6×10$^6$ to 5×10$^6$ Sarcoma-180 cells were transplanted subcutaneously. Next day, the test medicine solution was injected into the tail vein in a single dose. Eight to twelve mice were employed for the solvent-dosed control group, and five mice were employed for the dosed group. Six days after the dosage, the tumor was cut out, and the weight thereof was measured. The antineoplastic effect was evaluated by the ratio (T/C) of the average tumor weight of the dosed group (T) to the average tumor weight of the solvent-dosed control group (C). The results are shown in Table 3.

TABLE 3

Antineoplastic Activity for Mice Having Sarcoma-180 Cells Transplanted subcutaneously

| Example No. | i.v. Dosage (mg/kg) | T/C |
| --- | --- | --- |
| 10 | 0.5 | 0.15 |
| 11 | 1.0 | 0.06 |
| 12 | 1.0 | 0.11 |
| 13 | 0.25 | 0.11 |
| 14 | 0.5 | 0.07 |
| 15 | 0.5 | 0.11 |
| 16 | 0.5 | 0.17 |
| 17 | 0.25 | 0.25 |
| 18 | 0.25 | 0.25 |
| 19 | 0.25 | 0.22 |
| 20 | 0.25 | 0.36* |
| 23 | 0.25 | 0.16 |
| 24 | 0.25 | 0.17 |
| 27 | 0.125 | 0.19 |
| 28 | 0.25 | 0.28 |
| 31 | 0.125 | 0.24 |
| 32 | 0.125 | 0.23 |
| 34 | 0.25 | 0.37 |
| 36 | 0.25 | 0.14 |
| 37 | 0.25 | 0.24 |
| 43 | 0.125 | 0.25 |
| 47 | 1.0 | 0.19 |
| 48 | 1.0 | 0.08 |
| 49 | 0.5 | 0.12 |
| 50 | 4.0 | 0.15 |
| 51 | 4.0 | 0.25 |
| 52 | 1.0 | 0.12 |
| 53 | 4.0 | 0.20 |
| 54 | 0.25 | 0.15 |

*(n = 4)

(3) Evaluation with mice having Colon-26 cells transplanted subcutaneously:

To the lateral region of a female mouse (CDF$_1$ strain, 8 to 12 week age), 1×10$^6$ Colon-26 cells were transplanted subcutaneously. On the sixth day after the transplantation, the test medicine solution-was injected into the tail vein in a single dose. Seven to twelve mice were employed for the solvent-dosed control group, and five mice were employed for the dosed group. One week after the dosage, the tumor was cut out, and the weight thereof was measured. The antineoplastic effect was evaluated by the ratio (T/C) of the average tumor weight of the dosed group (T) to the average tumor weight of the solvent-dosed control group (C). The results are shown in Table 4.

TABLE 4

Antineoplastic Activity for Mice Having Colon-26 Cells Transplanted subcutaneously

| Example No. | i.v. Dosage (mg/kg) | T/C |
| --- | --- | --- |
| 10 | 0.5 | 0.15 |
| 12 | 1.0 | 0.16 |
| 13 | 0.25 | 0.17 |
| 14 | 0.5 | 0.05 |
| 16 | 0.5 | 0.16 |
| 17 | 0.25 | 0.18 |
| 18 | 0.25 | 0.07 |
| 20 | 0.25 | 0.15 |

TABLE 4-continued

Antineoplastic Activity for Mice Having
Colon-26 Cells Transplanted subcutaneously

| Example No. | i.v. Dosage (mg/kg) | T/C |
|---|---|---|
| 23 | 0.25 | 0.12 |
| 24 | 0.25 | 0.11 |
| 47 | 1.0 | 0.07 |
| 48 | 1.0 | 0.06 |
| 49 | 0.5 | 0.09 |
| 63 | 0.5 | 0.04 |
| 75 | 0.5 | 0.17 |
| 76 | 0.5 | 0.06 |
| 77 | 0.5 | 0.06 |
| 78 | 0.125 | 0.26 |
| 79 | 0.5 | 0.09 |
| 86 | 0.5 | 0.4 |
| 90 | 1.0 | 0.31 |
| 97 | 0.5 | 0.11 |
| 98 | 0.5 | 0.29 |
| 99 | 2.0 | 0.05 |
| 107 | 0.5 | 0.07 |
| 108 | 0.0156 | 0.06 |
| 109 | 0.25 | 0.07 |

INDUSTRIAL USEFULNESS

As shown clearly from the above experiments, the compounds of the present invention have antineoplastic activity, and high selectivity to cancer cells, and therefor are useful.

We claim:

1. Trifluoromethylpyrroloindolecarboxylic acid ester derivatives represented by the general formula (1) and (2) below, optical isomers thereof, and pharmaceutically acceptable salts thereof:

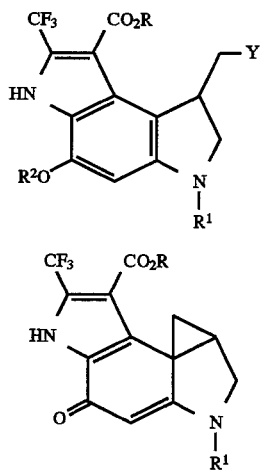

wherein
R is a lower alkyl group of $C_1$-$C_4$;
$R^1$ is selected from the group consisting of α-amino acid residue,

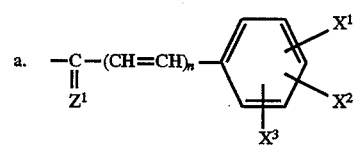

($X^1$, $X^2$, and $X^3$ are independently a hydrogen atom, OH, $OR^3$ ($R^3$ is a linear or branched lower alkyl group of $C_1$-$C_6$, or an aryl group), $OCOR^3$ ($R^3$ is the same as above), CHO, $NO_2$,

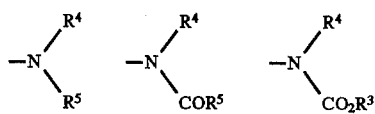

($R^4$ and $R^5$ are independently a hydrogen atom, a linear or branched lower alkyl group of $C_1$-$C_6$, or an aryl group ($R^3$ is the same as above)

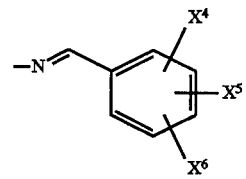

($X^4$, $X^5$, and $X^6$ are independently a hydrogen atom, $OR^3$, or

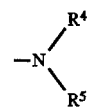

($R^3$, $R^4$, and $R^5$ are the same as above)),

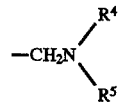

($R^4$, and $R^5$ are the same as above),

($R^4$, and $R^5$ are the same as above), $Z^1$ is O, S, or $NR^4$ ($R^4$ is the same as above), n is 0~2),

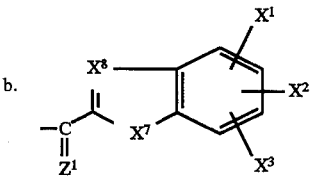

($X^7$ is O, S, or NH, $X^8$ is CH or N ($X^1$, $X^2$, $X^3$, and $Z^1$ are the same as above)),

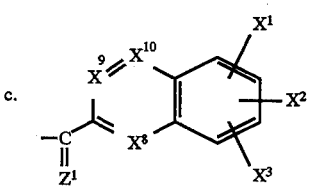

($X^9$, and $X^{10}$ are independently CH or N ($X^1$, $X^2$, $X^3$, $X^8$, and $Z^1$ are the same as above)), d. 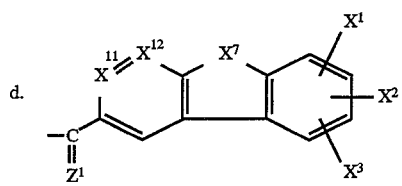

($X^{11}$, and $X^{12}$ are independently CH or N ($X^1$, $X^2$, $X^3$, $X^7$, and $Z^1$ are the same as above)), e. 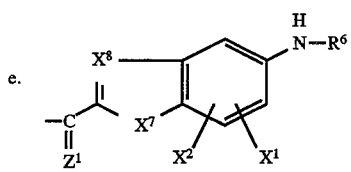

($R^6$ is represented by the above formula a, b, c, or d ($X^1$, $X^2$, $X^7$, $X^8$, and $Z^1$ are the same as above)), f. 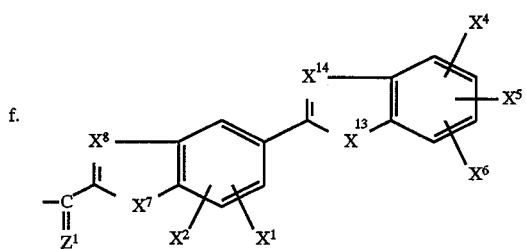

($X^{13}$ is O, S, or NH; $X^{14}$ is CH or N ($X^1$, $X^2$, $X^4$, $X^5$, $X^6$, $X^7$, $X^3$, and $Z^1$ are the same as above)), and g. 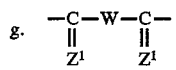

(W is —$(CH_2)_m$—, —$(CH_2)_m$—$Z^2$—$(CH_2)_n$—, or

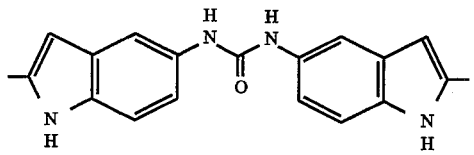

($Z^1$ is the same as above), $Z^2$ is S, O, or NH, and m and n are independently 0~16);

$R^2$ is a hydrogen atom, a protecting group for the hydroxyl group or a biologically decomposable substituent selected from the group consisting of N,N-di (lower alkyl) carbamoyl group, piperidinocarbonyl group which may be substituted with piperidino group, or (4-alkyl-1-piperazinyl) carbonyl group which alkyl may be substituted with hydroxyl group, di(lower alkyl)amino group and hydroxy alkoxy group and Y is a halogen atom, an arylsulfonyloxy group, a lower alkylsulfonyloxy groups, a haloalkylsulfonyloxy group, or an azide.

2. A trifluoromethylpyrroloindolecarboxylic acid ester intermediate represented by general formula (3):

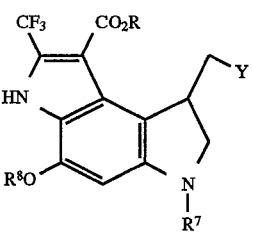

(where R is a lower alkyl group of $C_1$~$C_4$; $R_7$ is a hydrogen atom or a protective group for an amino group; $R_8$ is a hydrogen atom or a protective group for a hydroxyl group; Y is a hydroxyl group, a protective group for a hydroxyl group, a halogen atom, an arylsulfonyloxy group, a lower alkylsulfonyloxy group, a haloalkylsulfonyloxy group, or an azide).

3. A trifluoromethylcyclopropapyrroloindole-carboxylic acid ester intermediate represented by general formula (4):

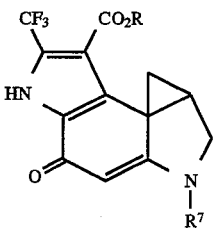

(where R is a lower alkyl group of $C_1$~$C_4$; and $R_7$ is a hydrogen atom or a protective group for an amino group).

4. A process of deprotecting a compound represented by general formula (3a) below:

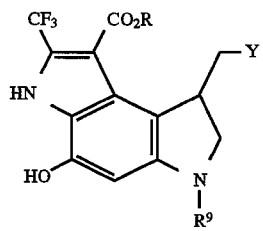

(where R is a lower alkyl group of $C_1$~$C_4$l; $R_9$ is a protective group for an amino group; Y is a halogen atom, an arylsulfonyloxy group, a lower alkylsulfonyloxy group, a haloalkylsulfonyloxy group, or an azide) to form a compound represented by general formula (3b) or a salt thereof:

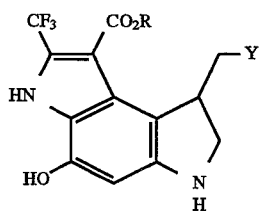

(where R and Y are the same as defined above), and subsequently acylating or imidoylating the compound of formula (3b) to produce a compound represented by general formula (3c) below:

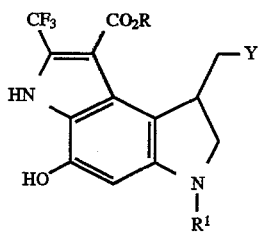 (3c)

(where $R^1$ is selected from the group consisting of α-amino acid residue,

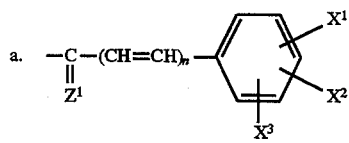

($X^1$, $X^2$ and $X^3$ are independently a hydrogen atom, OH, $OR^3$ ($R^3$ is a linear or branched lower alkyl group of $C_1$~$C_6$, or an aryl group), $OCOR^3$($R^3$ is the same as above), CHO, $NO_2$,

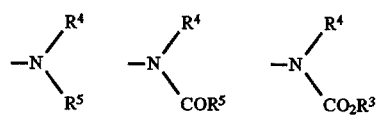

($R^4$ and $R^5$ are independently a hydrogen atom, a linear or branched lower alkyl group of $C_1$~$C_6$, or an aryl group ($R^3$ is the same as above)),

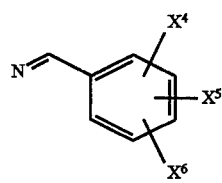

($X^4$, $X^5$, and $X^6$ are independently a hydrogen atom, $OR^3$, or

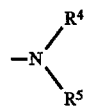

($R^3$, $R^4$, and $R^5$ are the same as above)),

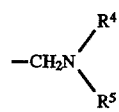

($R^4$, and $R^5$ are the same as above),

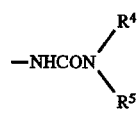

($R^4$, and $R^5$ are the same as above), $Z^1$ is O, S, or $NR^4$($R^4$ is the same as above), n is 0~2),

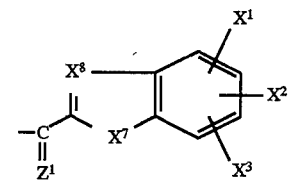

($X^7$ is O, S, or NH, $X^8$ is CH or N ($X^1$, $X^2$, $X^3$, and $Z^1$ are the same as above)),

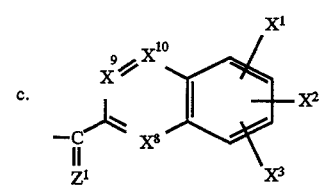

($X^9$, and $X^{10}$ are independently CH or N ($X^1$, $X^2$, $X^3$, $X^8$, and $Z^1$ are the same as above)),

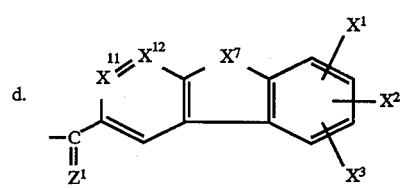

($X^{11}$, and $X^{12}$ are independently CH or N ($X^1$, $X^2$, $X^3$, $X^7$, and $Z^1$ are the same as above)),

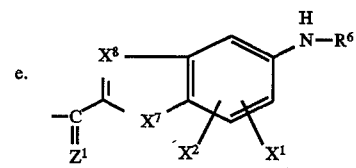

($R^6$ is represented by the above formula a, b, c, or d ($X^1$, $X^2$, $X^7$, $X^8$, and $Z^1$ are the same as above)),

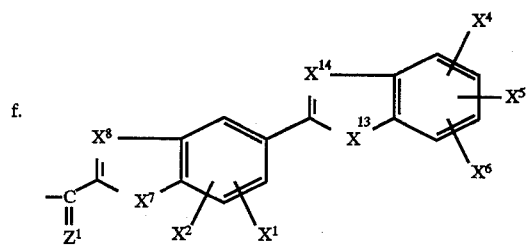

($X^{13}$ is O, S, or NH; $X^{14}$ is CH or N ($X^1$, $X^2$, $X^4$, $X^5$, $X^6$, $X^7$, $X^8$, and $Z^1$ are the same as above)), and g. 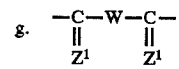

(W is —(CH$_2$)$_m$—, —(CH$_2$)$_m$—Z$^2$—(CH$_2$)$_n$—, or

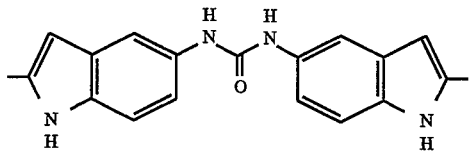

(Z$^1$ is the same as above), Z$^2$ is S, O, or NH, and m and n are independently 0~16); and R and Y are as defined above).

5. A process of protecting the hydroxyl group of a compound represented by general formula (3c) with a biologically decomposable substituent

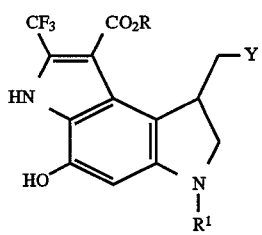      (3c)

(where R is a lower alkyl group of C$_1$~C$_4$;

R$^1$ is selected from the group consisting of α-amino acid residue, a. 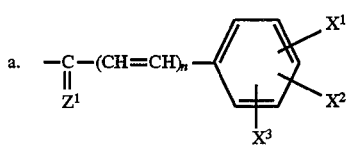

(X$^1$, X$^2$, and X$^3$ are independently a hydrogen atom, OH, OR$^3$ (R$^3$ is a linear or branched lower alkyl group of C$_1$~C$_6$, or an aryl group), OCOR$^3$(R$^3$ is the same as above), CHO, NO$_2$,

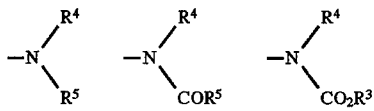

(R$^4$ and R$^5$ are independently a hydrogen atom, a linear or branched lower alkyl group of C$_1$~C$_6$, or an aryl group (R$^3$ is the same as above),

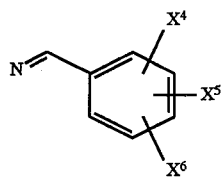

(X$^4$, X$^5$, and X$^6$ are independently a hydrogen atom, OR$^3$, or

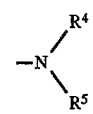

(R$^3$, R$^4$, and R$^5$ are the same as above)),

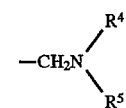

(R$^4$, and R$^5$ are the same as above),

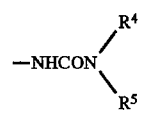

(R$^4$, and R$^5$ are the same as above), Z$^1$ is O, S, or NR$^4$(R$^4$ is the same as above), n is 0~2), b. 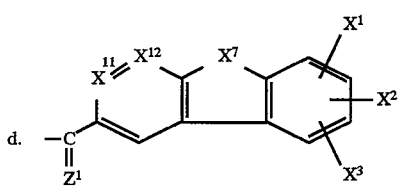

(X$^7$ is O, S, or NH, X$^8$ is CH or N (X$^1$, X$^2$, X$^3$, and Z$^1$ are the same as above)), c. (X$^9$, and X$^{10}$ are independently CH or N (X$^1$, X$^2$, X$^3$, X$^8$, and Z$^1$ are the same as above)), d. (X$^{11}$, and X$^{12}$ are independently CH or N (X$^1$, X$^2$, X$^3$, X$^7$, and Z$^1$ are the same as above)), e. 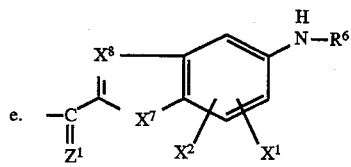

(R⁶ is represented by the above formula a, b, c, or d ($X^1$, $X^2$, $X^7$, $X^8$, and $Z^1$ are the same as above)), f. 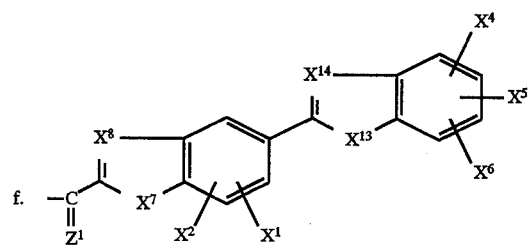

($X^{13}$ is O, S, or NH; $X^{14}$ is CH or N ($X^1$, $X^2$, $X^4$, $X^5$, $X^6$, $X^7$, $X^8$, and $Z^1$ are the same as above)), and g. 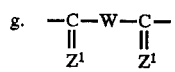

(W is —$(CH_2)_m$—, —$(CH_2)_m$—$Z^2$—$(CH_2)_n$—, or

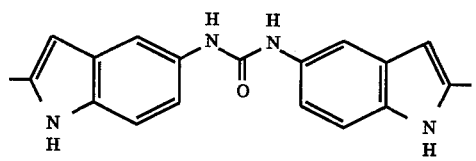

($Z^1$ is the same as above), $Z^2$ is S, O, or NH, and m and n are independently 0~16);

and Y is a halogen atom, an arylsulfonyloxy group, a lower alkylsulfonyloxy group, a haloalkylsulfonyloxy group, or an azide to produce a compound of general formula (3d):

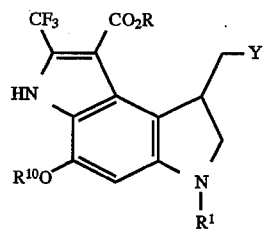 (3d)

(where $R^{10}$ is a biologically decomposable substituent selected from the group consisting of N,N-di(lower alkyl) carbamoyl group, piperidinocarbonyl group which may be substituted with piperidino group, or (4-alkyl-1-piperazinyl) carbonyl group which alkyl may be substituted with hydroxyl group, di(lower alkyl)amino group and hydroxy alkoxy group, and R, $R^1$ and Y are as defined above.

6. A process of ring closure of a compound represented by general formula (3c) in the presence of a basic catalyst:

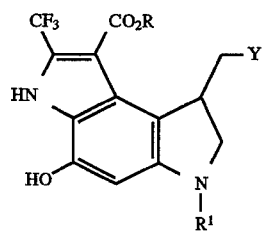 (3c)

(where R is a lower alkyl group of $C_{1\sim4}$;
$R^1$ is selected from the group consisting of α-amino acid residue, a. 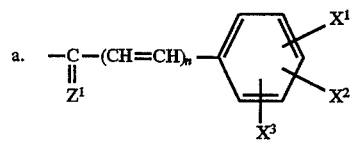

($X^1$, $X^2$ and $X^3$ are independently a hydrogen atom, OH, $OR^3$ ($R^3$ is a linear or branched lower alkyl group of $C_1$-$C_6$, or an aryl group), $OCOR^3$($R^3$ is the same as above), CHO, $NO_2$,

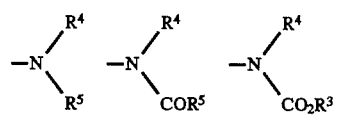

($R^4$ and $R^5$ are independently a hydrogen atom, a linear or branched lower alkyl group of $C_1$-$C_6$, or an aryl group ($R^3$ is the same as above)),

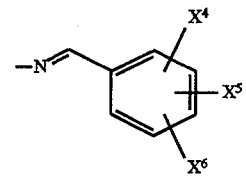

($X^4$, $X^5$, and $X^6$ are independently a hydrogen atom, $OR^3$, or

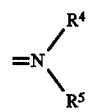

($R^3$, $R^4$, and $R^5$ are the same as above),

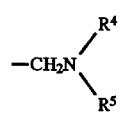

($R^4$, and $R^5$ are the same as above)),

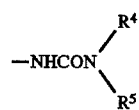

($R^4$, and $R^5$ are the same as above), $Z^1$ is O, S, or $NR^4$($R^4$ is the same as above), n is 0~2), b. 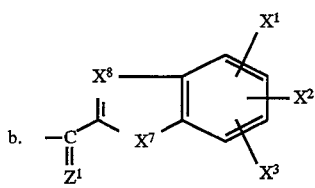

($X^7$ is O, S, or NH, $X^8$ is CH or N ($X^1$, $X^2$, $X^3$, and $Z^1$ are the same as above)), c. 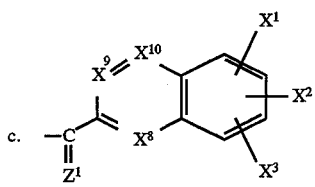

($X^9$, and $X^{10}$ are independently CH or N ($X^1$, $X^2$, $X^3$, $X^8$, and $Z^1$ are the same as above)), d. 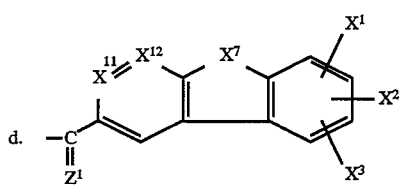

($X^{11}$, and $X^{12}$ are independently CH or N ($X^1$, $X^2$, $X^3$, $X^7$, and $Z^1$ are the same as above)), e. 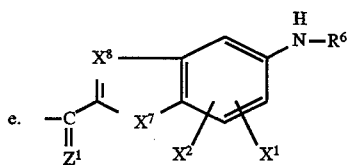

($R^6$ is represented by the above formula a, b, c, or d ($X^1$, $X^2$, $X^7$, $X^8$, and $Z^1$ are the same as above)), f. 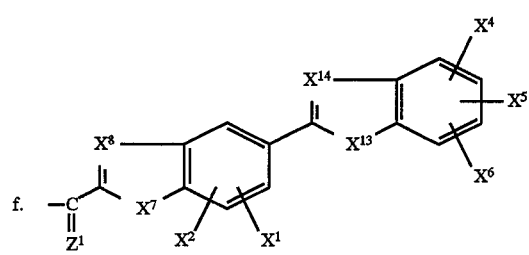

($X^{13}$ is O, S, or NH; $X^{14}$ is CH or N ($X^1$, $X^2$, $X^4$, $X^5$, $X^6$, $X^7$, $X^8$, and $Z^1$ are the same as above)), and g. 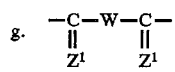

(W is $-(CH_2)_m-$, $-(CH_2)_m-Z^2-(CH_2)_n-$, or

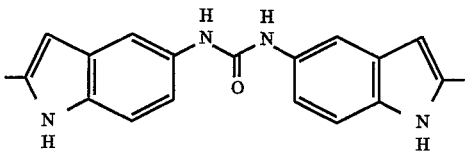

($Z^1$ is the same as above), $Z^2$ is S, O, or NH, and m and n are independently 0~16);

and Y is a halogen atom, an arylsulfonyloxy group, a lower alkylsulfonyloxy group, a haloalkylsulfonyloxy group, or an azide to produce a compound of general formula (4a):

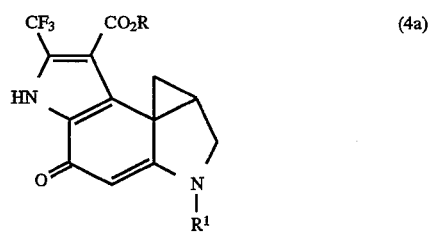 (4a)

(where R and $R^1$ are as defined above).

7. A process of addition of an acid to a compound represented by general formula (4a):

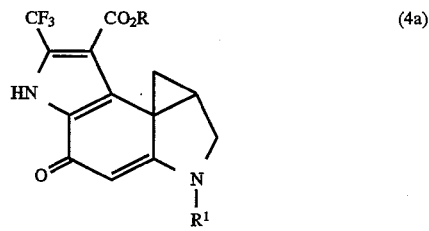 (4a)

(where R is a lower alkyl group of $C_1$~$C_4$;

$R^1$ is selected from the group consisting of α-amino acid residue, a. 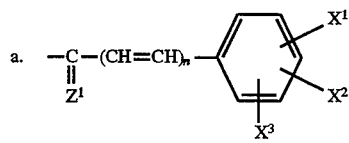

($X^1$, $X^2$ and $X^3$ are independently a hydrogen atom, OH, $OR^3$ ($R^3$ is a linear or branched lower alkyl group of $C_1$~$C_6$, or an aryl group), $OCOR^3$($R^3$ is the same as above), CHO, $NO_2$,

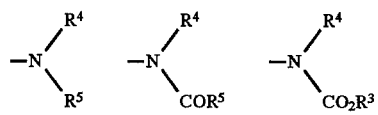

($R^4$ and $R^5$ are independently a hydrogen atom, a linear or branched lower alkyl group of $C_1$~$C_6$, or an aryl group ($R^3$ is the same as above)),

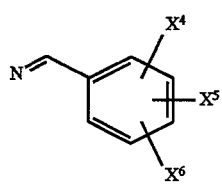

($X^4$, $X^5$, $X^6$ are independently a hydrogen atom, $OR^3$, or

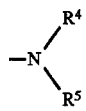

($R^3$, $R^4$, and $R^5$ are the same as above)),

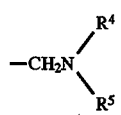

($R^4$, and $R^5$ are the same as above)),

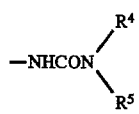

($R^4$, and $R^5$ are the same as above), $Z^1$ is O, S, or $NR^4$ ($R^4$ is the same as above), n is 0~2), b. 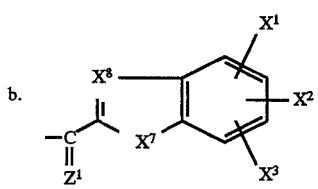

($X^7$ is O, S, or NH, $X^8$ is CH or N ($X^1$, $X^2$, $X^3$, and $Z^1$ are the same as above)), c. 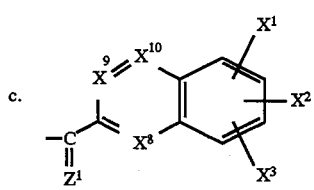

($X^9$, and $X^{10}$ are independently CH or N ($X^1$, $X^2$, $X^3$, $X^8$, and $Z^1$ are the same as above)), d. 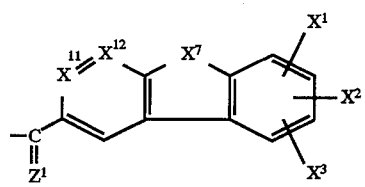

($X^{11}$, and $X^{12}$ are independently CH or N ($X^1$, $X^2$, $X^3$, $X^7$, and $Z^1$ are the same as above)), e. 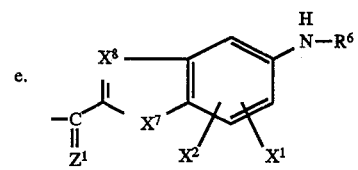

($R^6$ is represented by the above formula a, b, c, or d ($X^1$, $X^2$, $X^7$, $X^8$, and $Z^1$ are the same as above)), f. 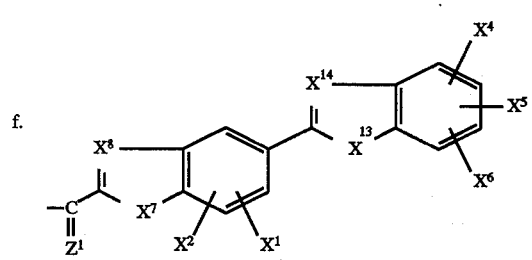

($X^{13}$ is O, S, or NH; $X^{14}$ is CH or N ($X^1$, $X^2$, $X^4$, $X^5$, $X^6$, $X^7$, $X^8$, $Z^1$ are the same as above)), and g. 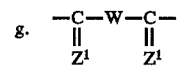

(W is $-(CH_2)_m-$, $-(CH_2)_m-Z^2-(CH_2)_n-$, or

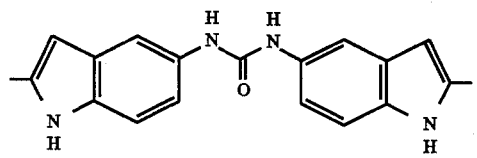

($Z^1$ is the same as above), $Z^2$ is S, O, or NH, and m and n are independently 0~16) to produce a compound of general formula (3c):

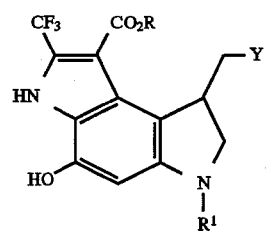

(3c)

(where Y is a halogen atom, an arylsulfonyloxy group, a lower alkylsulfonyloxy group, a haloalkylsulfonyloxy group, or an azide; and R and $R^1$ are as defined above).

* * * * *

UNITED STATES PATENT AND TRADEMARK OFFICE
CERTIFICATE OF CORRECTION

PATENT NO. : 5,629,430

ISSUED : May 13, 1997

INVENTOR(S) : Shiro Terashima, et al

It is certified that error appears in the above-identified patent and that said Letters Patent is hereby corrected as shown below:

Column 4, line 62, change "(hydroxyethyl)-1-piperazinyl]carbonyl"

to --hydroxyethyl)-1-piperazinyl]carbonyl--.

Signed and Sealed this

Twenty-eighth Day of April, 1998

*Attest:*

BRUCE LEHMAN

*Attesting Officer*  *Commissioner of Patents and Trademarks*